US009517315B2

(12) United States Patent
Meyer et al.

(10) Patent No.: US 9,517,315 B2
(45) Date of Patent: Dec. 13, 2016

(54) OSCILLATING POSITIVE EXPIRATORY PRESSURE DEVICE

(71) Applicant: Trudell Medical International, London (CA)

(72) Inventors: Adam Meyer, London (CA); Raphael Kopala, London (CA); Chris Dobson, London (CA); James Schmidt, London (CA); Neritan Alizoti, London (CA)

(73) Assignee: Trudell Medical International, London, Ontario (CA)

( * ) Notice: Subject to any disclaimer, the term of this patent is extended or adjusted under 35 U.S.C. 154(b) by 369 days.

(21) Appl. No.: 14/092,091

(22) Filed: Nov. 27, 2013

(65) Prior Publication Data
US 2014/0150790 A1 Jun. 5, 2014

Related U.S. Application Data

(60) Provisional application No. 61/781,533, filed on Mar. 14, 2013, provisional application No. 61/733,791,
(Continued)

(51) Int. Cl.
*A61M 16/00* (2006.01)
*A61M 16/20* (2006.01)
*A61M 16/08* (2006.01)

(52) U.S. Cl.
CPC ..... *A61M 16/0006* (2014.02); *A61M 16/0057* (2013.01); *A61M 16/208* (2013.01);
(Continued)

(58) Field of Classification Search
CPC ............ A61M 16/0006; A61M 16/208; A61M 16/0057; A61M 16/0866; A61M 16/20; A61M 2205/3365
(Continued)

(56) References Cited

U.S. PATENT DOCUMENTS 393,869 A  12/1888  Warren
938,808 A  11/1909  Yount
(Continued)

FOREIGN PATENT DOCUMENTS

CA  2563723  10/2006
CA  2563723  4/2007
(Continued)

OTHER PUBLICATIONS

International Search Report from PCT/IB2013/002681 dated Mar. 7, 2014.
(Continued)

*Primary Examiner* — Jackie T Ho
*Assistant Examiner* — Margaret Luarca
(74) *Attorney, Agent, or Firm* — Brinks Gilson & Lione

(57) ABSTRACT

A respiratory treatment device comprising at least one chamber, a chamber inlet configured to receive air into the at least one chamber, at least one chamber outlet configured to permit air to exit the at least one chamber, and a flow path defined between the chamber inlet and the at least one chamber outlet. A restrictor member positioned in the flow path is moveable between a closed position, where a flow of air along the flow path is restricted, and an open position, where the flow of air along the flow path is less restricted. A vane in fluid communication with the flow path is operatively connected to the restrictor member and is configured to reciprocate between a first position and a second position in response to the flow of air along the flow path.

17 Claims, 69 Drawing Sheets

Related U.S. Application Data filed on Dec. 5, 2012, provisional application No. 61/731,861, filed on Nov. 30, 2012.

(52) U.S. Cl.
CPC ......... *A61M 16/0866* (2014.02); *A61M 16/20* (2013.01); *A61M 16/205* (2014.02); *A61M 2205/3365* (2013.01)

(58) Field of Classification Search
USPC .................................................. 128/204.18
See application file for complete search history.

(56) References Cited

U.S. PATENT DOCUMENTS

| | | | |
|---|---|---|---|
| 2,670,739 | A | 3/1954 | NcNeill |
| 2,918,917 | A | 12/1959 | Emerson |
| 3,710,780 | A | 1/1973 | Milch |
| 3,908,987 | A | 9/1975 | Boehringer |
| 4,054,134 | A | 10/1977 | Kritzer |
| 4,062,358 | A | 12/1977 | Kritzer |
| 4,182,366 | A | 1/1980 | Boehringer |
| 4,198,969 | A | 4/1980 | Virag |
| 4,221,381 | A | 9/1980 | Ericson |
| 4,226,233 | A | 10/1980 | Kritzer |
| 4,231,375 | A | 11/1980 | Boehringer et al. |
| 4,267,832 | A | 5/1981 | Hakkinen |
| 4,275,722 | A | 6/1981 | Sorensen |
| 4,298,023 | A | 11/1981 | McGinnis |
| 4,327,740 | A | 5/1982 | Shuman |
| 4,403,616 | A | 9/1983 | King |
| 4,436,090 | A | 3/1984 | Darling |
| 4,470,412 | A | 9/1984 | Nowacki et al. |
| 4,601,465 | A | 7/1986 | Roy |
| 4,611,591 | A | 9/1986 | Inui et al. |
| 4,635,631 | A | 1/1987 | Izumi |
| 4,651,731 | A | 3/1987 | Vicenzi et al. |
| 4,739,987 | A | 4/1988 | Nicholson |
| 4,770,413 | A | 9/1988 | Green |
| 4,973,047 | A | 11/1990 | Norell |
| 4,981,295 | A | 1/1991 | Belman et al. |
| 5,018,517 | A | 5/1991 | Liardet |
| 5,042,467 | A | 8/1991 | Foley |
| 5,065,746 | A | 11/1991 | Steen |
| 5,193,529 | A | 3/1993 | Labaere |
| 5,345,930 | A | 9/1994 | Cardinal et al. |
| 5,381,789 | A | 1/1995 | Marquardt |
| 5,451,190 | A | 9/1995 | Liardet |
| 5,479,920 | A | 1/1996 | Piper et al. |
| 5,540,220 | A | 7/1996 | Gropper et al. |
| 5,569,122 | A | 10/1996 | Cegla |
| 5,570,682 | A | 11/1996 | Johnson |
| 5,598,839 | A | 2/1997 | Niles et al. |
| 5,613,489 | A | 3/1997 | Miller |
| 5,645,049 | A | 7/1997 | Foley et al. |
| 5,647,345 | A | 7/1997 | Saul |
| 5,655,520 | A | 8/1997 | Howe |
| 5,658,221 | A | 8/1997 | Hougen |
| 5,791,339 | A | 8/1998 | Winter |
| 5,829,429 | A | 11/1998 | Hughes |
| 5,848,588 | A | 12/1998 | Foley et al. |
| 5,862,802 | A | 1/1999 | Bird |
| 5,890,998 | A | 4/1999 | Hougen |
| 5,893,361 | A | 4/1999 | Hughes |
| 5,899,832 | A | 5/1999 | Hougen |
| 5,910,071 | A | 6/1999 | Hougen |
| 5,925,831 | A | 7/1999 | Storsved |
| 6,026,807 | A | 2/2000 | Puderbaugh et al. |
| 6,044,841 | A | 4/2000 | Verdun et al. |
| 6,058,932 | A | 5/2000 | Hughes |
| 6,066,101 | A | 5/2000 | Johnson |
| 6,083,141 | A | 7/2000 | Hougen |
| 6,089,105 | A | 7/2000 | Ricciardelli |
| 6,102,038 | A | 8/2000 | DeVries |
| 6,167,881 | B1 | 1/2001 | Hughes |
| 6,176,235 | B1 | 1/2001 | Benarrouch et al. |
| D440,651 | S | 4/2001 | Foran |
| 6,217,284 | B1* | 4/2001 | Lawrence ............ F03B 17/062 415/3.1 |
| 6,240,917 | B1 | 6/2001 | Andrade |
| 6,253,766 | B1 | 7/2001 | Niles |
| 6,293,279 | B1 | 9/2001 | Schmidt et al. |
| 6,340,025 | B1 | 1/2002 | Van Brunt |
| 6,345,617 | B1 | 2/2002 | Engelbreth et al. |
| 6,412,481 | B1 | 7/2002 | Bienvenu et al. |
| 6,500,095 | B1 | 12/2002 | Hougen |
| 6,557,549 | B2 | 5/2003 | Schmidt et al. |
| 6,581,595 | B1 | 6/2003 | Murdock et al. |
| 6,581,596 | B1 | 6/2003 | Truitt |
| 6,581,598 | B1 | 6/2003 | Foran et al. |
| 6,581,600 | B2 | 6/2003 | Bird |
| 6,595,203 | B1 | 7/2003 | Bird |
| 6,606,989 | B1 | 8/2003 | Brand |
| 6,615,831 | B1 | 9/2003 | Tuitt |
| 6,631,721 | B1 | 10/2003 | Salter et al. |
| 6,659,100 | B2 | 12/2003 | O'Rourke |
| 6,702,769 | B1 | 3/2004 | Fowler-Hawkins |
| 6,708,690 | B1 | 3/2004 | Hete et al. |
| 6,708,691 | B1 | 3/2004 | Hayek |
| 6,726,598 | B1 | 4/2004 | Jarvis |
| D490,519 | S | 5/2004 | Pelerossi et al. |
| 6,776,159 | B2 | 8/2004 | Pelerossi et al. |
| 6,848,443 | B2 | 2/2005 | Schmidt et al. |
| 6,851,425 | B2 | 2/2005 | Jaffre |
| 6,904,906 | B2 | 6/2005 | Salter |
| 6,923,181 | B2 | 8/2005 | Tuck |
| 6,929,007 | B2 | 8/2005 | Emerson |
| 6,984,214 | B2 | 1/2006 | Fowler-Hawkins |
| 7,059,324 | B2 | 6/2006 | Pelerossi et al. |
| 7,096,866 | B2 | 8/2006 | Be'eri et al. |
| 7,134,434 | B2 | 11/2006 | Truitt et al. |
| 7,165,547 | B2 | 1/2007 | Truitt et al. |
| 7,188,621 | B2 | 3/2007 | DeVries |
| 7,191,776 | B2 | 3/2007 | Niles |
| 7,191,780 | B2 | 3/2007 | Faram |
| 7,214,170 | B2 | 5/2007 | Sumners et al. |
| 7,617,821 | B2 | 11/2009 | Hughes |
| 7,699,054 | B2 | 4/2010 | Pelerossi et al. |
| 7,717,847 | B2 | 5/2010 | Smith |
| 7,771,472 | B2 | 8/2010 | Hendricksen |
| 7,779,841 | B2 | 8/2010 | Dunsmore et al. |
| 7,798,148 | B2 | 9/2010 | Doshi |
| 7,856,979 | B2 | 12/2010 | Doshi |
| 7,909,033 | B2 | 3/2011 | Faram |
| 8,006,922 | B2 | 8/2011 | Katzer |
| 8,025,051 | B2 | 9/2011 | Dagsland |
| 8,025,054 | B2 | 9/2011 | Dunsmore et al. |
| 8,043,236 | B2 | 10/2011 | Goldshtein et al. |
| 8,051,854 | B2 | 11/2011 | Faram |
| RE43,174 | E | 2/2012 | Schmidt et al. |
| 8,118,024 | B2 | 2/2012 | DeVries et al. |
| 8,225,785 | B2 | 7/2012 | Richards et al. |
| 8,327,849 | B2 | 12/2012 | Grychowski et al. |
| 8,460,223 | B2 | 6/2013 | Huster et al. |
| 8,469,029 | B2 | 6/2013 | Brown et al. |
| 8,485,179 | B1 | 7/2013 | Meyer |
| 8,539,951 | B1* | 9/2013 | Meyer ............... A61M 16/0096 128/200.24 |
| 2007/0259759 | A1 | 11/2007 | Sumners et al. |
| 2008/0053456 | A1 | 3/2008 | Brown et al. |
| 2008/0110451 | A1* | 5/2008 | Dunsmore ............ A61M 16/00 128/200.14 |
| 2010/0139655 | A1 | 6/2010 | Genosar |
| 2010/0307487 | A1 | 12/2010 | Dunsmore et al. |
| 2011/0290240 | A1 | 12/2011 | Meyer et al. |
| 2012/0012112 | A1 | 1/2012 | Dunsmore et al. |
| 2012/0097164 | A1 | 4/2012 | Rozario et al. |
| 2012/0304988 | A1* | 12/2012 | Meyer .................... A63B 23/18 128/203.12 |

(56) References Cited

U.S. PATENT DOCUMENTS

| | | | |
|---|---|---|---|
| 2013/0133649 A1 | 5/2013 | Grychowski et al. | |
| 2013/0284171 A1 | 10/2013 | Adam et al. | |
| 2013/0312746 A1 | 11/2013 | Grychowski | |

FOREIGN PATENT DOCUMENTS

| | | |
|---|---|---|
| EP | 0 372 148 A1 | 6/1990 |
| EP | 0 678 306 A2 | 10/1995 |
| EP | 1435251 | 12/2003 |
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 89/03707 A1 | 5/1989 |
| WO | WO 96/40376 | 12/1996 |
| WO | WO 99/16490 | 4/1999 |
| WO | WO 00/27455 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO 2014/202923 | 12/2014 |
| WO | WO 2014/202924 | 12/2014 |
| WO | WO 2014/203115 | 12/2014 |

OTHER PUBLICATIONS

U.S. Appl. No. 29/438,878, filed Dec. 4, 2012, Meyer.
U.S. Appl. No. 13/966,759, filed Aug. 14, 2013, Meyer.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
Human growth hormone, cortisol, and acid-base balance changes after hyperventilation and breath-holding; PubMed—indexed for MEDLINE; Int J Sports Med., Dec. 1986; 7(6):311-5, Djarova T.
Bosco C, Cardinale M. & Tsarpela O (1999). Influence of vibration on mechanical power and electromyogram activity in human arm flexor muscles. Eur J Appl Physiol 79, 306-311.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
PCT International Search Report for PCT/IB2012/001089, Oct. 5, 2012.
PCT International Written Opinion for PCT/IB2012/001089, Oct. 5, 2012.
PCT International Search Report from PCT/IB2013/002681 dated Mar. 7, 2014.
PCT Written Opinion from PCT/IB2013/002681 dated Mar. 7, 2014.

* cited by examiner

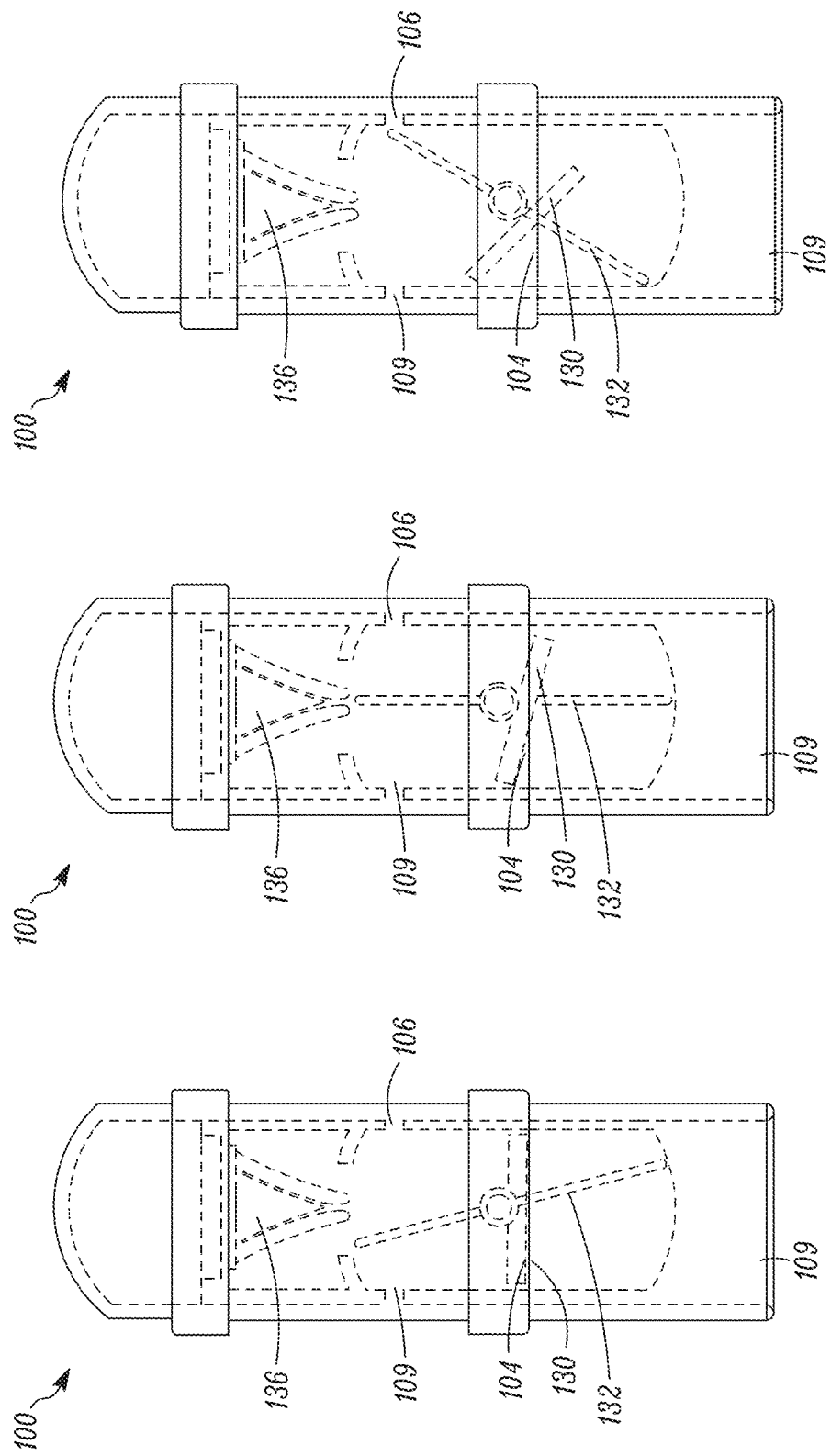

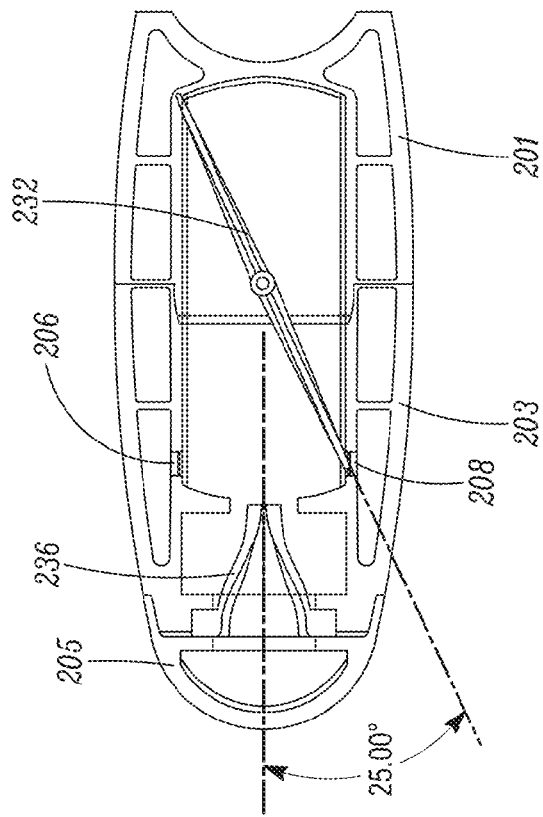
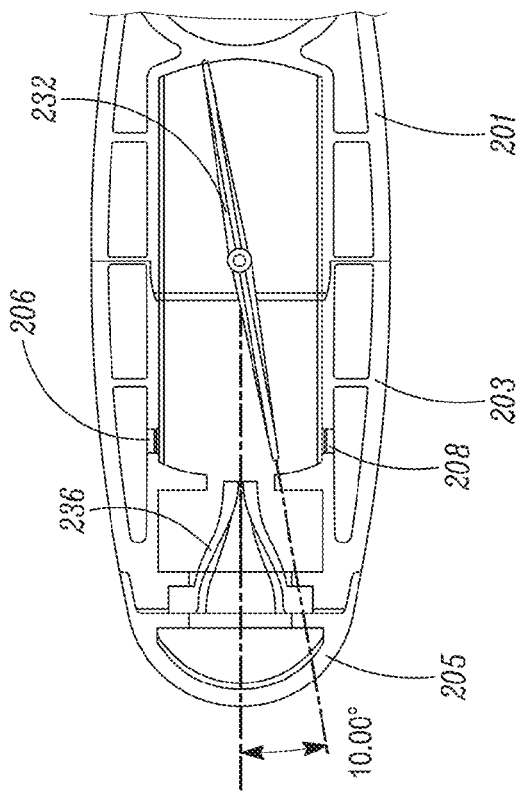
FIG. 32B
FIG. 32A

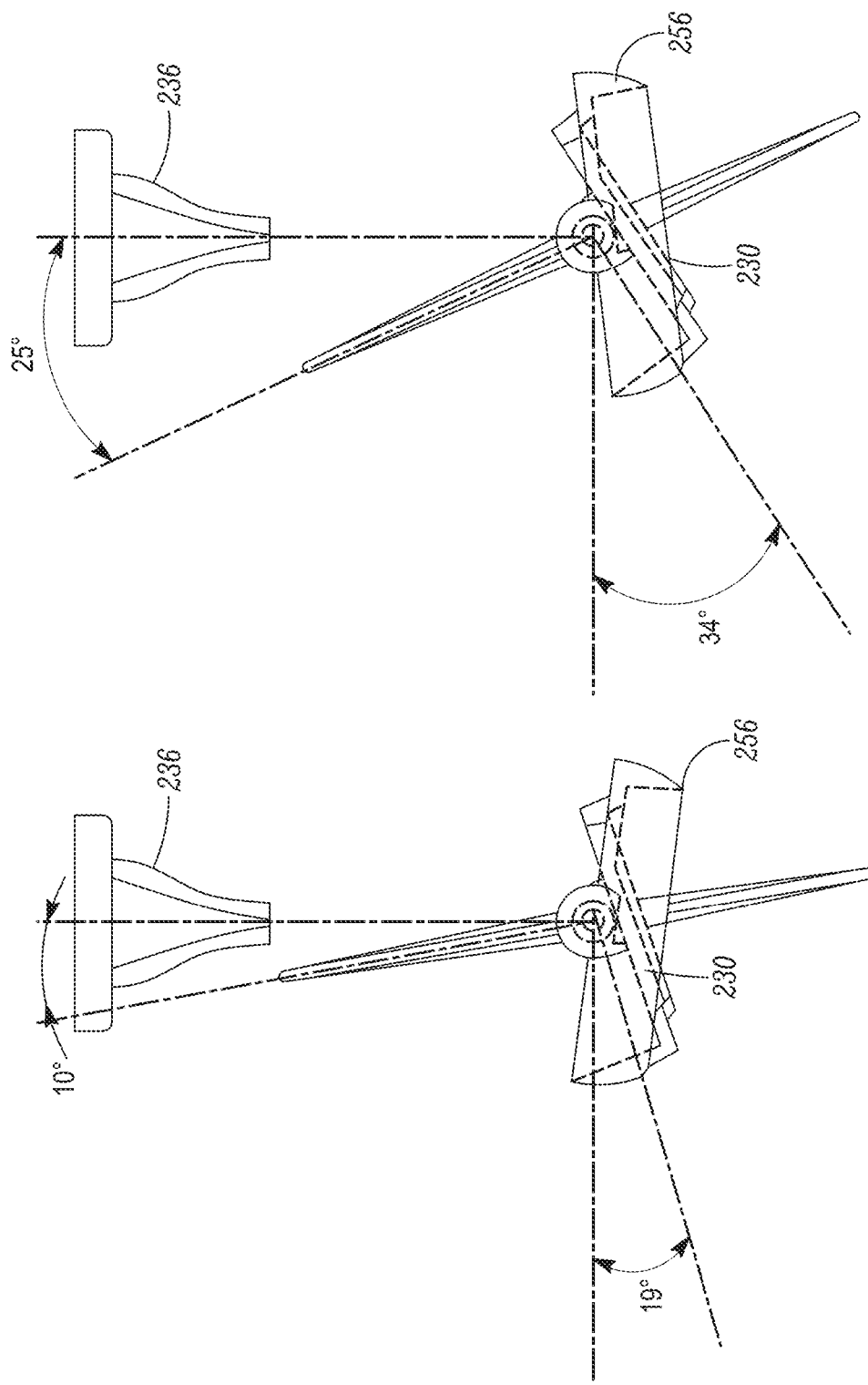

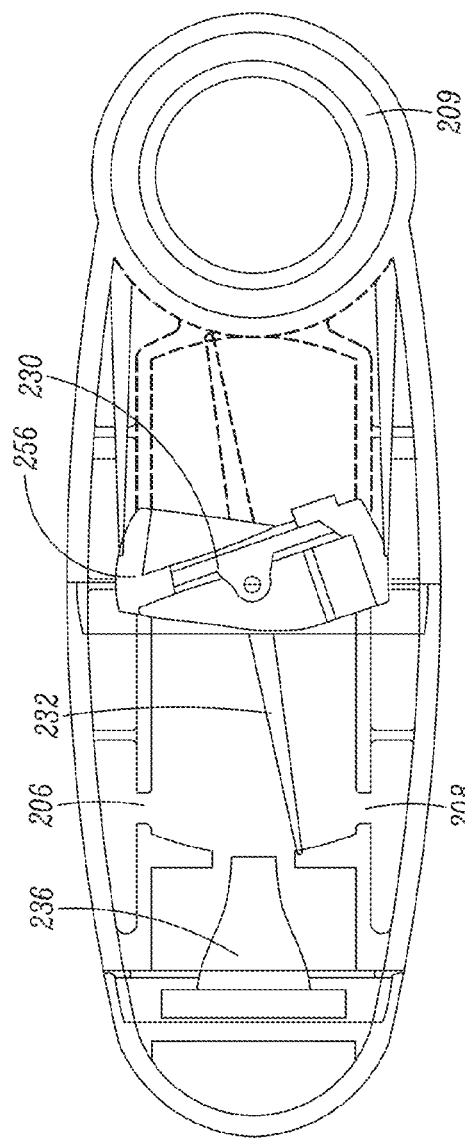
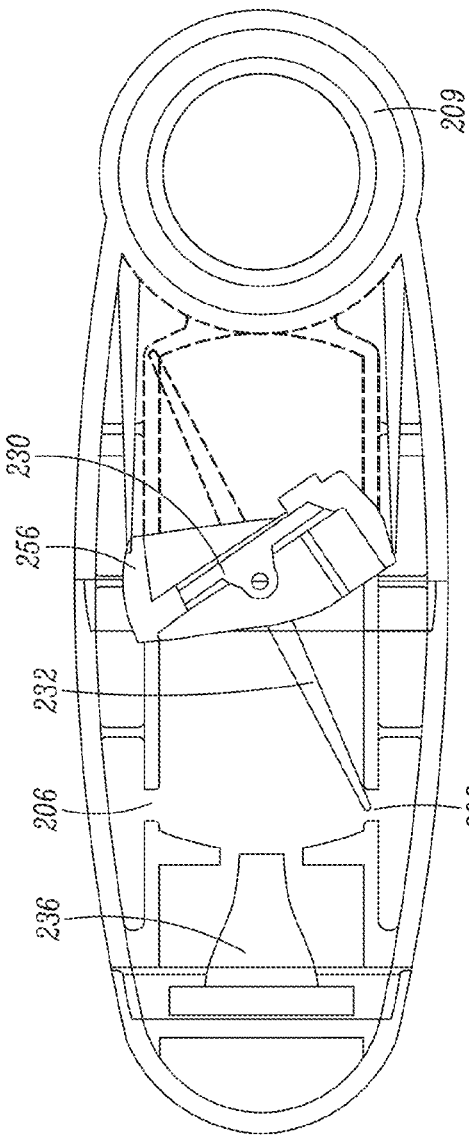
FIG. 34A
FIG. 34B

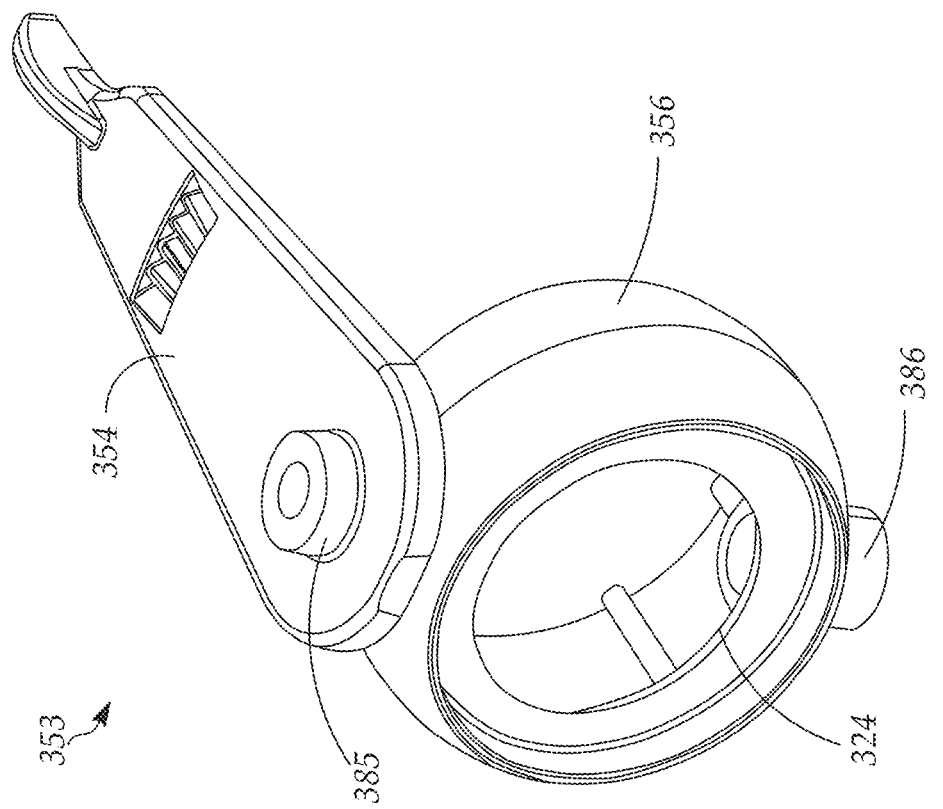

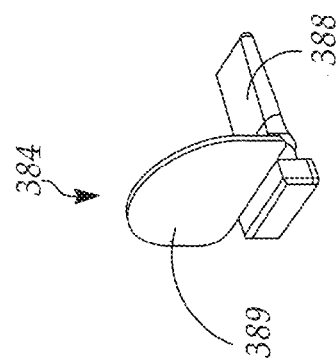
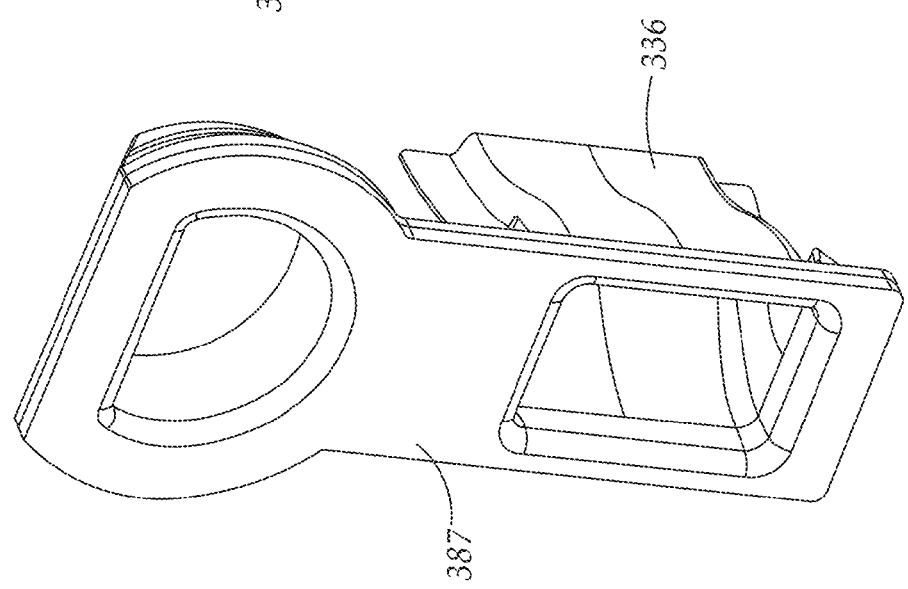
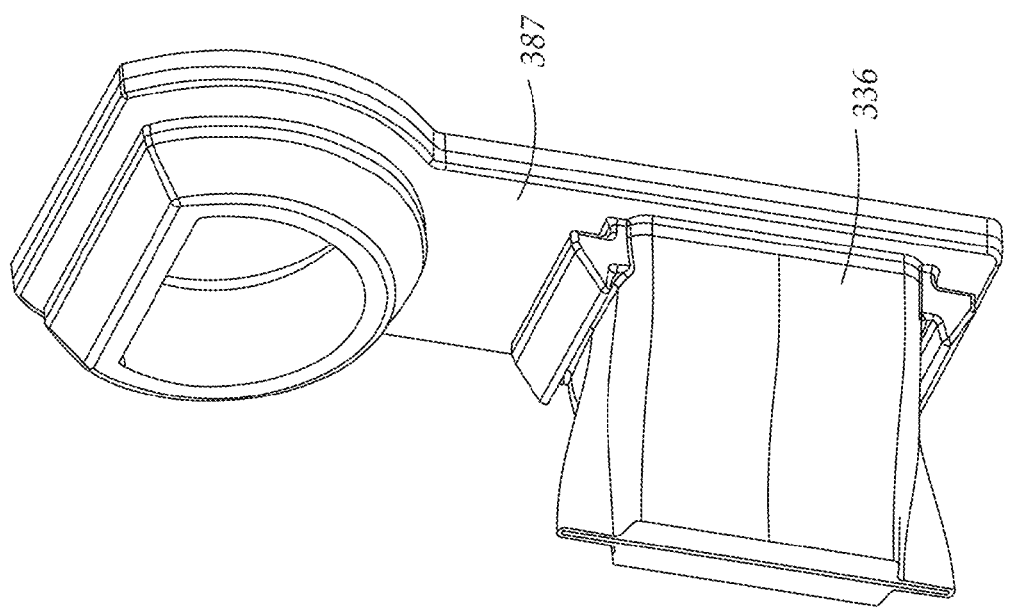

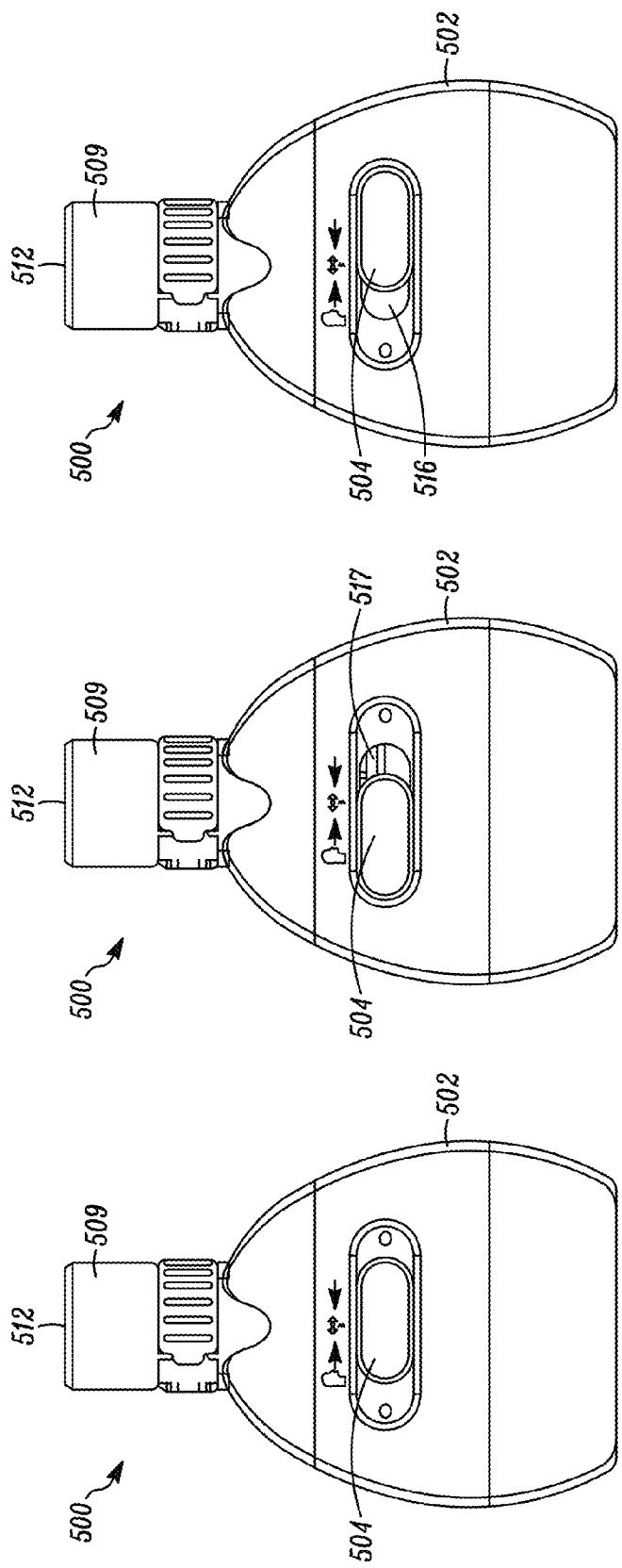

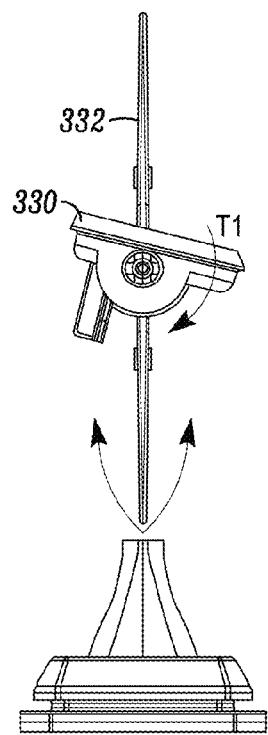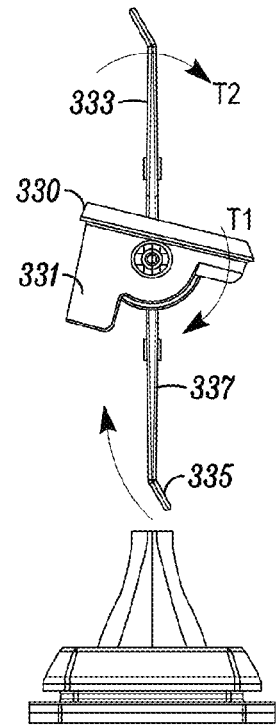
FIG. 80A	FIG. 80B
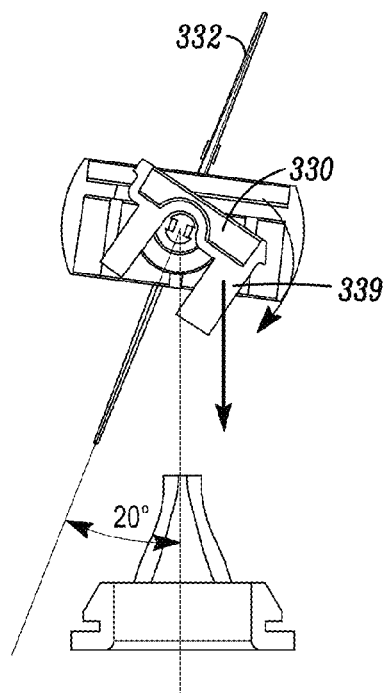
FIG. 81

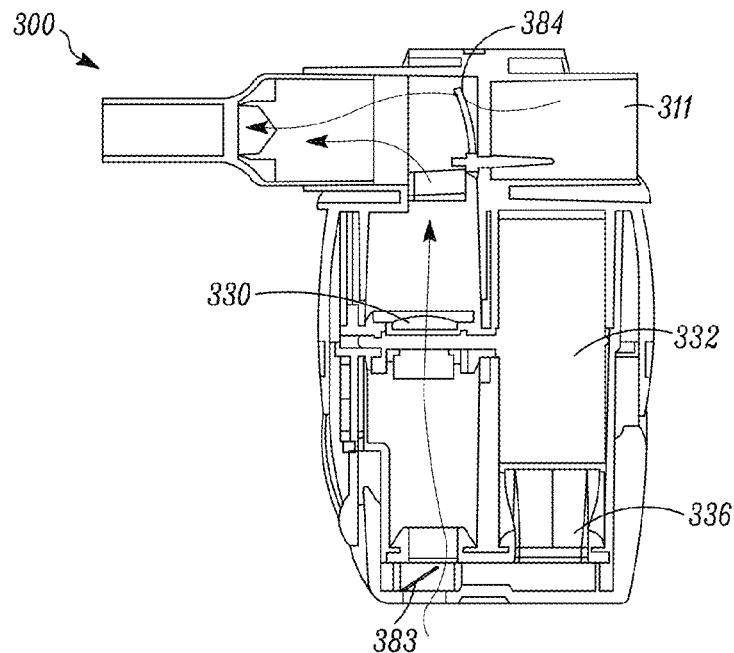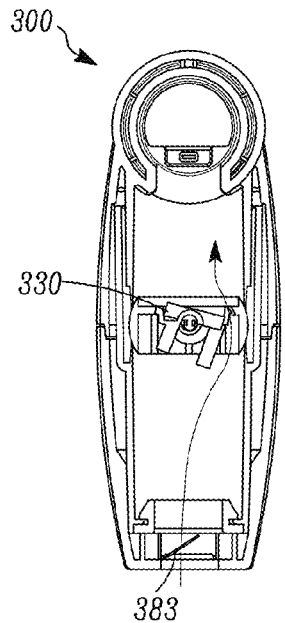
FIG. 85A    FIG. 85B
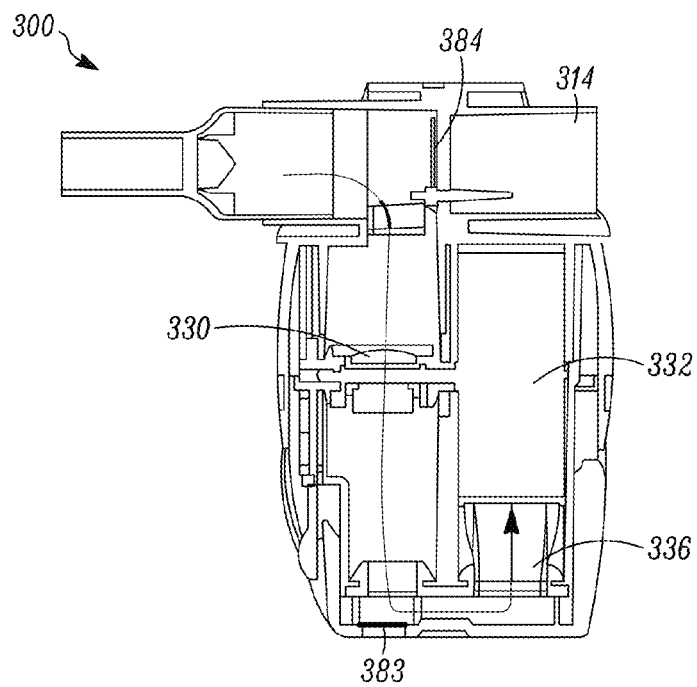
FIG. 85C

OSCILLATING POSITIVE EXPIRATORY PRESSURE DEVICE

RELATED APPLICATIONS

This application claims the benefit of U.S. Provisional Application No. 61/731,861, filed on Nov. 30, 2012, U.S. Provisional Application No. 61/733,791, filed on Dec. 5, 2012, and U.S. Provisional Application No. 61/781,533, filed on Mar. 14, 2013, all of which are incorporated herein by reference.

TECHNICAL FIELD

The present disclosure relates to a respiratory treatment device, and in particular, to an oscillating positive expiratory pressure ("OPEP") device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most patients, and such patients can assume responsibility for the administration of OPEP therapy throughout a hospitalization and also from home. To that end, a number of portable OPEP devices have been developed.

BRIEF SUMMARY

In one aspect, a respiratory treatment device includes a housing enclosing at least one chamber, a chamber inlet configured to receive air into the at least one chamber, at least one chamber outlet configured to permit air to exit the at least one chamber, and a flow path defined between the chamber inlet and the at least one chamber outlet. An orifice is positioned in the at least one chamber along the flow path such that the flow path passes through the orifice. A vane is positioned adjacent the orifice and is configured to rotate in response to the flow of air through the orifice. A peripheral portion of the vane is angled relative to a central portion of the vane to direct substantially all the flow of air through the orifice to a side of the vane when the central portion of the vane is substantially aligned with the orifice. The central portion of the vane may be substantially planar.

In another aspect, a restrictor member is operatively connected to the vane and is configured to rotate between a closed position, where the flow of air along the flow path is restricted, and an open position, where the flow of air along the flow path is less restricted. The restrictor member and the vane may be operatively connected by a shaft. The restrictor member may have a center of mass offset from an axis of rotation of the shaft. A force of gravity may bias the restrictor member and the vane toward a position where the central portion of the vane is not aligned with the orifice.

In another aspect, a respiratory treatment device includes a housing enclosing at least one chamber, a chamber inlet configured to receive air into the at least one chamber, at least one chamber outlet configured to permit air to exit the at least one chamber, and a flow path defined between the chamber inlet and the at least one chamber outlet. An orifice is positioned in the at least one chamber along the flow path such that the flow path passes through the orifice. A vane is positioned adjacent the orifice and is configured to rotate in response to the flow of air through the orifice. A peripheral portion of the vane is configured to flex relative to a central portion of the vane in response to the flow of air through the orifice. The vane may be substantially planar.

In another aspect, a flexibility of the peripheral portion of the vane may be greater than a flexibility of the central portion of the vane. The peripheral portion of the vane and the central portion of the vane may be separated by at least one hinge point. The at least one hinge point may include a channel.

In another aspect, a restrictor member is operatively connected to the vane, the restrictor member being configured to rotate between a closed position, where the flow of air along the flow path is restricted, and an open position, where the flow of air along the flow path is less restricted.

In another aspect, a respiratory treatment device includes a housing enclosing at least one chamber, a chamber inlet configured to receive air into the at least one chamber, at least one chamber outlet configured to permit air to exit the at least one chamber, and a flow path defined between the chamber inlet and the at least one chamber outlet. An orifice is positioned in the at least one chamber along the flow path such that the flow path passes through the orifice. A vane is positioned adjacent the orifice and is configured to rotate in response to the flow of air through the orifice. The vane is biased toward a position where a central portion of the vane is not aligned with the orifice. The vane may be substantially planar.

In yet another aspect, the vane is biased by an elastic band. An end of the elastic band may be attached to a side of the vane opposite the side of the vane adjacent the orifice.

In another aspect, a restrictor member is operatively connected to the vane, the restrictor member being configured to rotate between a closed position, where the flow of air along the flow path is restricted, and an open position, where the flow of air along the flow path is less restricted. The restrictor member and the vane may be operatively connected by a shaft. The restrictor member may have a center of mass offset from an axis of rotation of the shaft. A force of gravity may bias the restrictor member and the vane toward the position where the central portion of the vane is not aligned with the orifice.

BRIEF DESCRIPTION OF THE DRAWINGS

FIGS. 15A-C are top phantom views of the OPEP device of FIG. 1 showing an exemplary illustration of the operation of the OPEP device of FIG. 1;

FIGS. 32A-B are partial cross-sectional views taken along line III in FIG. 18 of the OPEP device, illustrating possible configurations of the OPEP device;

FIGS. 33A-B are top phantom views illustrating the adjustability of the OPEP device of FIG. 18;

FIGS. 34A-B are top phantom views of the OPEP device of FIG. 18, illustrating the adjustability of the OPEP device;

FIG. 47 is a front perspective view of an adjustment mechanism of the OPEP device of FIG. 35;

FIG. 50 is a front perspective view of a variable nozzle of the OPEP device of FIG. 35;

FIG. 51 is a rear perspective view of the variable nozzle of FIG. 50;

FIG. 52 is a front perspective view of the one-way valve of the OPEP device of FIG. 35.

FIG. 64A-C are front views of the respiratory treatment device of FIG. 61, illustrating the positioning of a switch relative to the openings to selectively control administration of OPEP therapy upon exhalation, inhalation, or both exhalation and inhalation;

FIGS. 80A-B are top views illustrating the torques applied to the restrictor member and the vane of the OPEP device of FIG. 35 during a period of exhalation, and modifications thereto;

FIG. 81 is a top view of another modified restrictor member;

FIGS. 85A-C are cross-sectional views of the OPEP device of FIG. 35, adapted to rotate the restrictor member and the vane during a period of inhalation; and, FIGS. 86A-C are partial top views of a modified vane.

DETAILED DESCRIPTION

Figure 1:
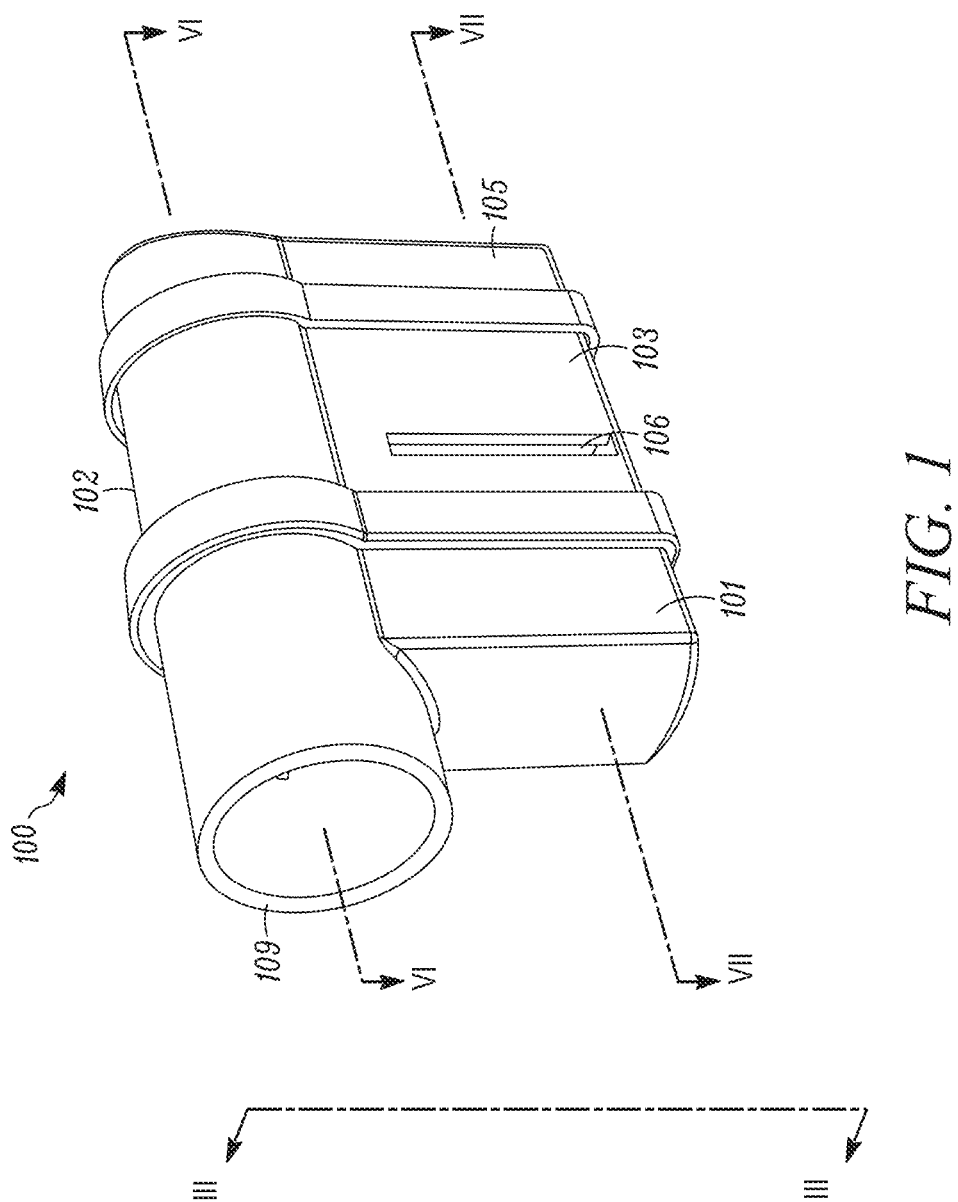
FIG. 1 is a front perspective view of an OPEP device.
Figure 2:
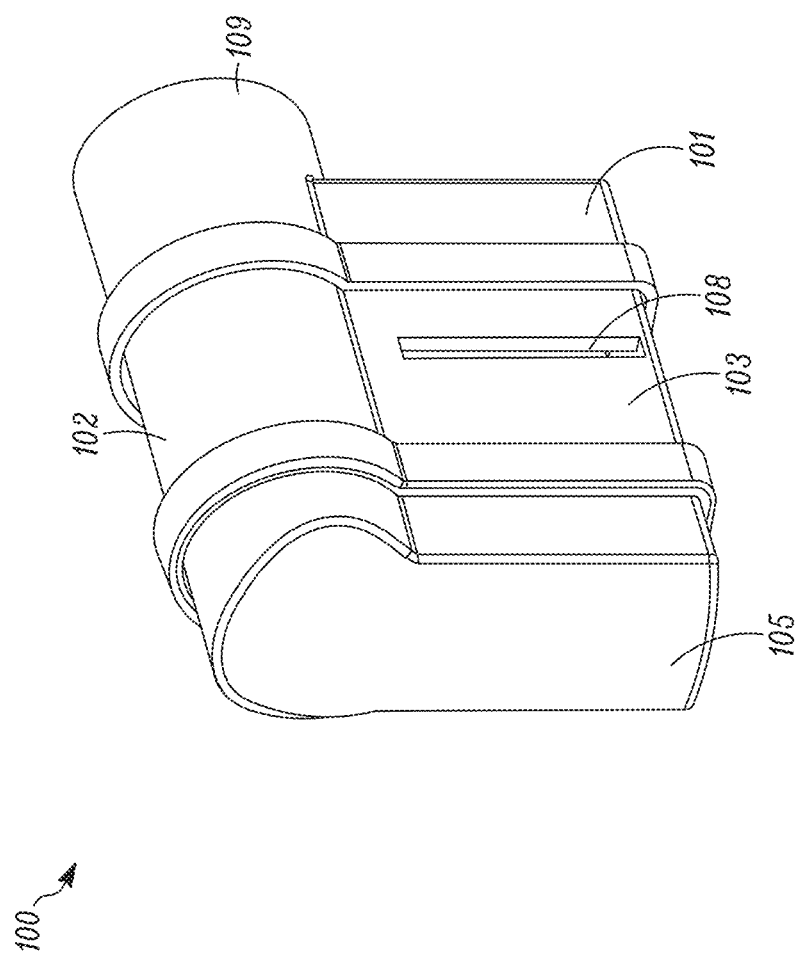
FIG. 2 is a rear perspective view of the OPEP device of FIG. 1.

OPEP therapy is effective within a range of operating conditions. For example, an adult human may have an exhalation flow rate ranging from 10 to 60 liters per minute, and may maintain a static exhalation pressure in the range of 8 to 18 cm $H_2O$. Within these parameters, OPEP therapy is believed to be most effective when changes in the exhalation pressure (i.e., the amplitude) range from 5 to 20 cm $H_2O$ oscillating at a frequency of 10 to 40 Hz. In contrast, an adolescent may have a much lower exhalation flow rate, and may maintain a lower static exhalation pressure, thereby altering the operating conditions most effective for the administration of OPEP therapy. Likewise, the ideal operating conditions for someone suffering from a respiratory illness, or in contrast, a healthy athlete, may differ from those of an average adult. As described below, the components of the disclosed OPEP devices are selectable and/or adjustable so that ideal operating conditions (e.g., amplitude and frequency of oscillating pressure) may be identified and maintained. Each of the various embodiments described herein achieve frequency and amplitude ranges that fall within the desired ranges set forth above. Each of the various embodiments described herein may also be configured to achieve frequencies and amplitudes that fall outside the ranges set forth above.

First Embodiment

Referring first to FIGS. 1-4, a front perspective view, a rear perspective view, a cross-sectional front perspective view, and an exploded view of an OPEP device 100 are shown. For purposes of illustration, the internal components of the OPEP device 100 are omitted in FIG. 3. The OPEP device 100 generally comprises a housing 102, a chamber inlet 104, a first chamber outlet 106, a second chamber outlet 108 (best seen in FIGS. 2 and 7), and a mouthpiece 109 in fluid communication with the chamber inlet 104. While the mouthpiece 109 is shown in FIGS. 1-4 as being integrally formed with the housing 102, it is envisioned that the mouthpiece 109 may be removable and replaceable with a mouthpiece 109 of a different size or shape, as required to maintain ideal operating conditions. In general, the housing 102 and the mouthpiece 109 may be constructed of any durable material, such as a polymer. One such material is Polypropylene. Alternatively, acrylonitrile butadiene styrene (ABS) may be used.

Alternatively, other or additional interfaces, such as breathing tubes or gas masks (not shown) may be attached in fluid communication with the mouthpiece 109 and/or associated with the housing 102. For example, the housing 102 may include an inhalation port (not shown) having a separate one-way inhalation valve (not shown) in fluid communication with the mouthpiece 109 to permit a user of the OPEP device 100 both to inhale the surrounding air through the one-way valve, and to exhale through the chamber inlet 104 without withdrawing the mouthpiece 109 of the OPEP device 100 between periods of inhalation and exhalation. In addition, any number of aerosol delivery devices may be connected to the OPEP device 100, for example, through the inhalation port mentioned above, for the simultaneous administration of aerosol and OPEP therapies. As such, the inhalation port may include, for example, an elastomeric adapter, or other flexible adapter, capable of accommodating the different mouthpieces or outlets of the particular aerosol delivery device that a user intends to use with the OPEP device 100. As used herein, the term aerosol delivery devices should be understood to include, for example, without limitation, any nebulizer, soft mist inhaler, pressurized metered dose inhaler, dry powder inhaler, combination of a holding chamber a pressurized metered dose inhaler, or the like. Suitable commercially available aerosol delivery devices include, without limitation, the AEROECLIPSE nebulizer, RESPIMAT soft mist inhaler, LC Sprint nebulizer, AEROCHAMBER PLUS holding chambers, MICRO MIST nebulizer, SIDESTREAM nebulizers, Inspiration Elite nebulizers, FLOVENT pMDI, VENTOLIN pMDI, AZMACORT pMDI, BECLOVENT pMDI, QVAR pMDI and AEROBID PMDI, XOPENEX pMDI, PROAIR pMDI, PROVENT pMDI, SYMBICORT pMDI, TURBOHALER DPI, and DISKHALER DPI. Descriptions of suitable aerosol delivery devices may be found in U.S. Pat. Nos. 4,566,452; 5,012,803; 5,012,804; 5,312,046; 5,497,944; 5,622,162; 5,823,179; 6,293,279; 6,435,177; 6,484,717; 6,848,443; 7,360,537; 7,568,480; and, 7,905,228, the entireties of which are herein incorporated by reference.

In FIGS. 1-4, the housing 102 is generally box-shaped. However, a housing 102 of any shape may be used. Furthermore, the chamber inlet 104, the first chamber outlet 106, and the second chamber outlet 108 could be any shape or series of shapes, such as a plurality (i.e., more than one) of circular passages or linear slots. More importantly, it should be appreciated that the cross-sectional area of the chamber inlet 104, the first chamber outlet 106, and the second chamber outlet 108 are only a few of the factors influencing the ideal operating conditions described above.

Preferably, the housing 102 is openable so that the components contained therein can be periodically accessed, cleaned, replaced, or reconfigured, as required to maintain the ideal operating conditions. As such, the housing 102 is shown in FIGS. 1-4 as comprising a front section 101, a middle section 103, and a rear section 105. The front section 101, the middle section 103, and the rear section 105 may be removably connected to one another by any suitable means, such as a snap-fit, a compression fit, etc., such that a seal forms between the relative sections sufficient to permit the OPEP device 100 to properly administer OPEP therapy.

Figure 3:
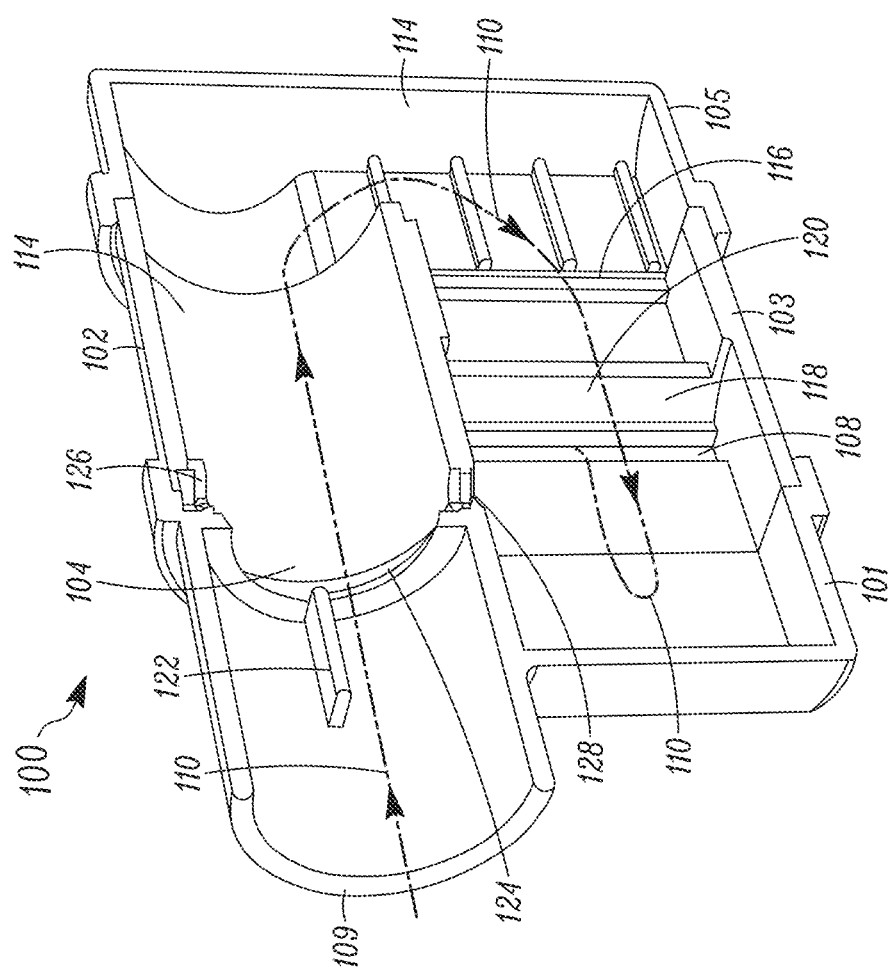
FIG. 3 is a cross-sectional perspective view taken along line III in FIG. 1 of the OPEP device shown without the internal components of the OPEP device.
Figure 7:
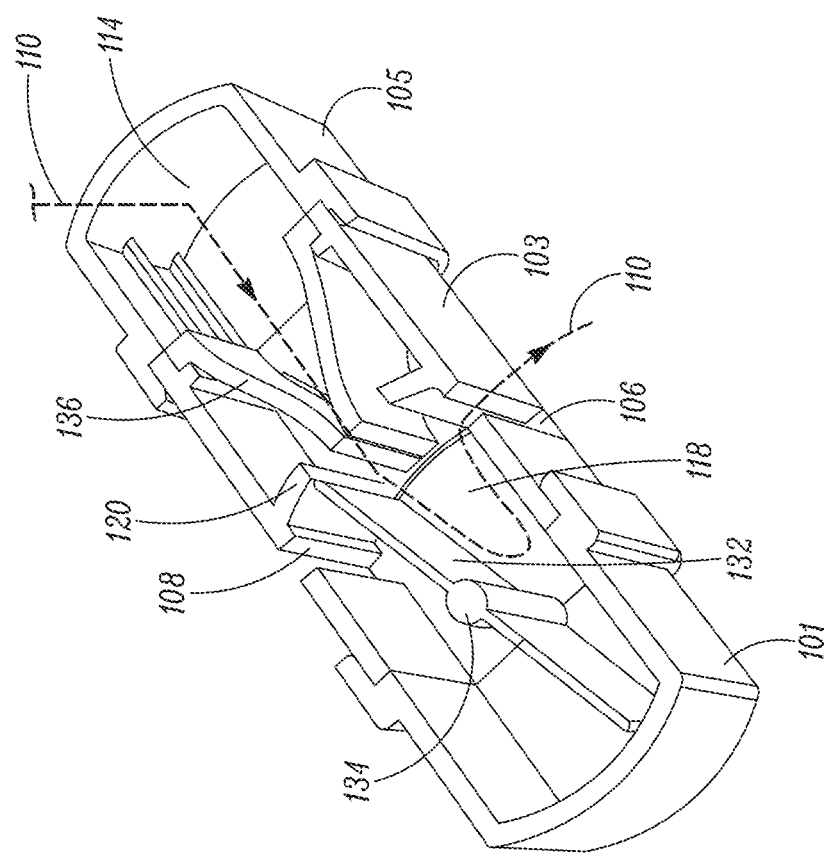
FIG. 7 is a different cross-sectional perspective view taken along line VII in FIG. 1 of the OPEP device shown with the internal components of the OPEP device.

As shown in FIG. 3, an exhalation flow path 110, identified by a dashed line, is defined between the mouthpiece 109 and at least one of the first chamber outlet 106 and the second chamber outlet 108 (best seen in FIG. 7). More specifically, the exhalation flow path 110 begins at the mouthpiece 109, passes through the chamber inlet 104, and enters into a first chamber 114, or an entry chamber. In the first chamber 114, the exhalation flow path makes a 180-degree turn, passes through a chamber passage 116, and enters into a second chamber 118, or an exit chamber. In the second chamber 118, the exhalation flow path 110 may exit the OPEP device 100 through at least one of the first chamber outlet 106 and the second chamber outlet 108. In this way, the exhalation flow path 110 is "folded" upon itself, i.e., it reverses longitudinal directions between the chamber inlet 104 and one of the first chamber outlet 106 or the second chamber outlet 108. However, those skilled in the art will appreciate that the exhalation flow path 110 identified by the dashed line is exemplary, and that air exhaled into the OPEP device 100 may flow in any number of directions or paths as it traverses from the mouthpiece 109 or chamber inlet 104 and the first chamber outlet 106 or the second chamber outlet 108.

FIG. 3 also shows various other features of the OPEP device 100 associated with the housing 102. For example, a stop 122 prevents a restrictor member 130 (see FIG. 5), described below, from opening in a wrong direction; a seat 124 shaped to accommodate the restrictor member 130 is formed about the chamber inlet 104; and, an upper bearing 126 and a lower bearing 128 are formed within the housing 102 and configured to accommodate a shaft rotatably mounted therebetween. One or more guide walls 120 are positioned in the second chamber 118 to direct exhaled air along the exhalation flow path 110.

Figure 5:
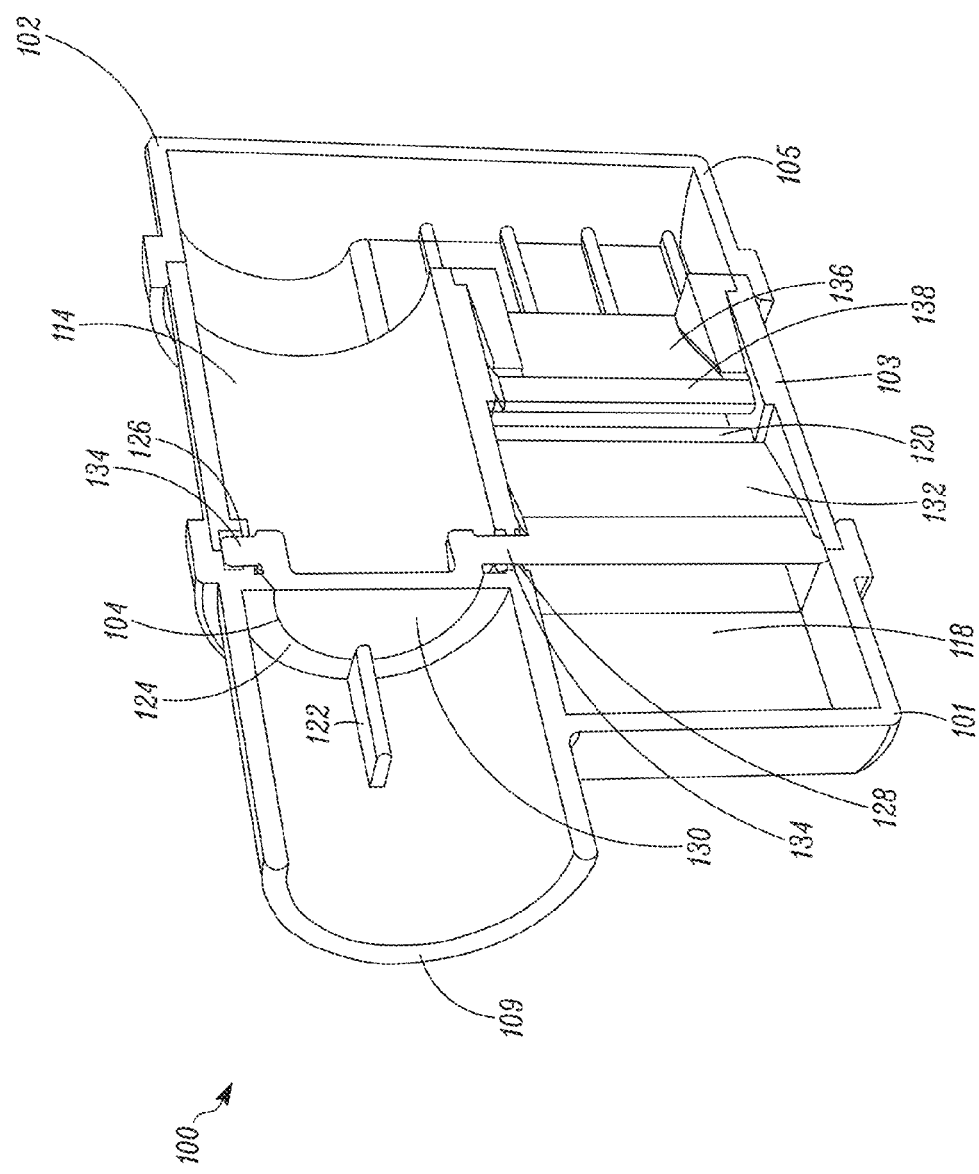
FIG. 5 is a cross-sectional perspective view taken along line III in FIG. 1 of the OPEP device shown with the internal components of the OPEP device.
Figure 6:
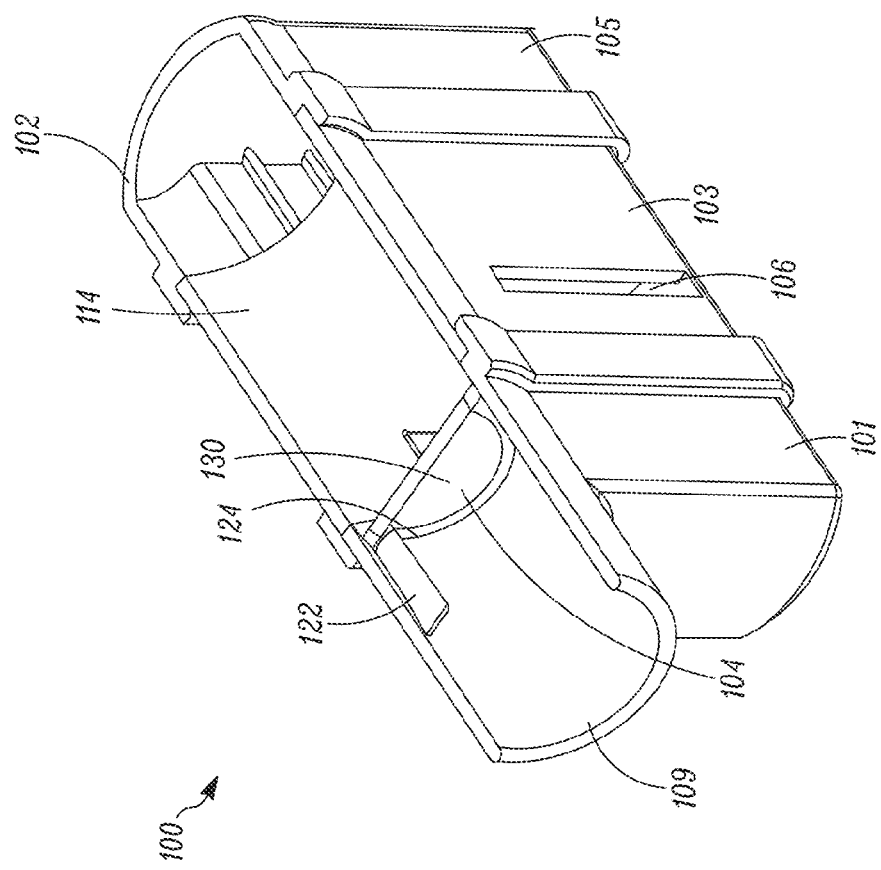
FIG. 6 is a different cross-sectional perspective view taken along line VI in FIG. 1 of the OPEP device shown with the internal components of the OPEP device.

Turning to FIGS. 5-7, various cross-sectional perspective views of the OPEP device 100 are shown with its internal components. The internal components of the OPEP device 100 comprise a restrictor member 130, a vane 132, and an optional variable nozzle 136. As shown, the restrictor member 130 and the vane 132 are operatively connected by means of a shaft 134 rotatably mounted between the upper bearing 126 and the lower bearing 128, such that the restrictor member 130 and the vane 132 are rotatable in unison about the shaft 134. As described below in further detail, the variable nozzle 136 includes an orifice 138 configured to increase in size in response to the flow of exhaled air therethrough.

Figure 4:
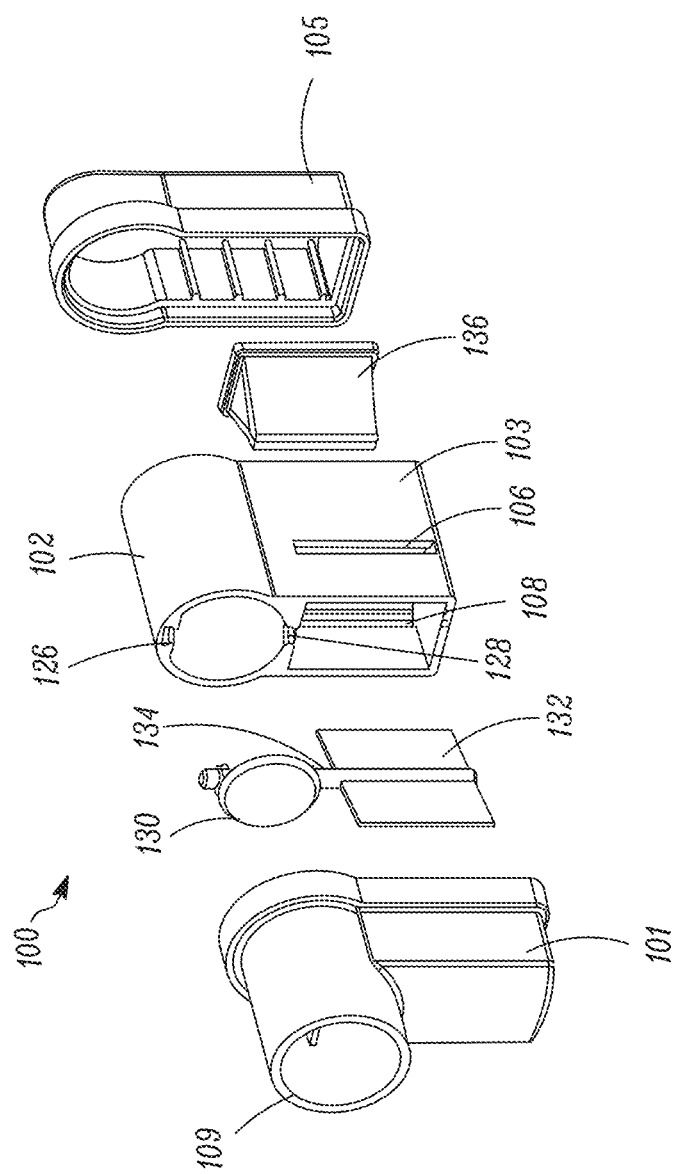
FIG. 4 is an exploded view of the OPEP device of FIG. 1, shown with the internal components of the OPEP device.

FIGS. 4-6 further illustrate the division of the first chamber 114 and the second chamber 118 within the housing 102. As previously described, the chamber inlet 104 defines an entrance to the first chamber 114. The restrictor member 130 is positioned in the first chamber 114 relative to a seat 124 about the chamber inlet 104 such that it is moveable between a closed position, where a flow of exhaled air along the exhalation flow path 110 through the chamber inlet 104 is restricted, and an open position, where the flow of exhaled air through the chamber inlet 104 is less restricted. Likewise, the variable nozzle 136, which is optional, is mounted about or positioned in the chamber passage 116, such that the flow of exhaled air entering the first chamber 114 exits the first chamber 114 through the orifice 138 of the variable nozzle 136. Exhaled air exiting the first chamber 114 through the orifice 138 of the variable nozzle 136 enters the second chamber, which is defined by the space within the housing 102 occupied by the vane 132 and the guide walls 120. Depending on the position of the vane 132, the exhaled air is then able to exit the second chamber 118 through at least one of the first chamber outlet 106 and the second chamber outlet 108.

Figure 9:
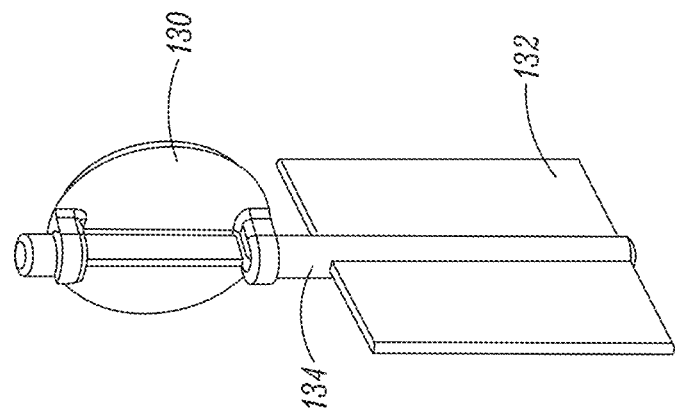
FIG. 9 is a rear perspective view of the restrictor member operatively connected to the vane shown in FIG. 8.
Figure 8:
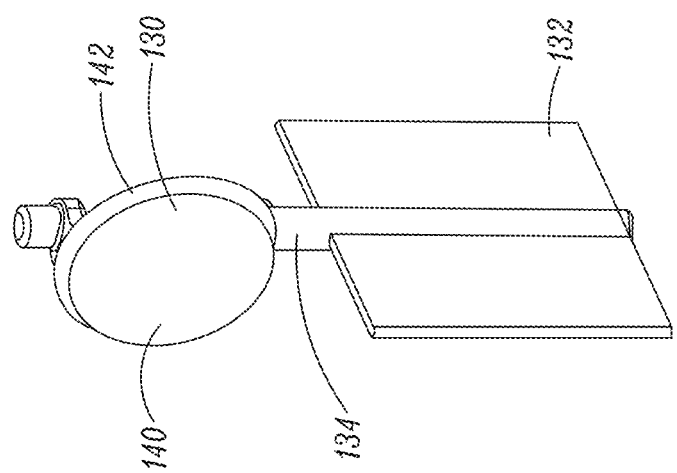
FIG. 8 is a front perspective view of a restrictor member operatively connected to a vane.

FIGS. 8-14 show the internal components of the OPEP device 100 in greater detail. Turning first to FIGS. 8-9, a front perspective view and a rear perspective view shows the restrictor member 130 operatively connected to the vane 132 by the shaft 134. As such, the restrictor member 130 and the vane 132 are rotatable about the shaft 134 such that rotation of the restrictor member 130 results in a corresponding rotation of the vane 132, and vice-versa. Like the housing 102, the restrictor member 130 and the vane 132 may be made of constructed of any durable material, such as a polymer. Preferably, they are constructed of a low shrink, low friction plastic. One such material is acetal.

As shown, the restrictor member 130, the vane 132, and the shaft 134 are formed as a unitary component. The restrictor member 130 is generally disk-shaped, and the vane 132 is planar. The restrictor member 130 includes a generally circular face 140 axially offset from the shaft 134 and a beveled or chamfered edge 142 shaped to engage the seat 124 formed about the chamber inlet 104. In this way, the restrictor member 130 is adapted to move relative to the chamber inlet 104 about an axis of rotation defined by the shaft 134 such that the restrictor member 130 may engage the seat 124 in a closed position to substantially seal and restrict the flow of exhaled air through the chamber inlet 104. However, it is envisioned that the restrictor member 130 and the vane 132 may be formed as separate components connectable by any suitable means such that they remain independently replaceable with a restrictor member 130 or a vane 132 of a different shape, size, or weight, as selected to maintain ideal operating conditions. For example, the restrictor member 130 and/or the vane 132 may include one or more contoured surfaces. Alternatively, the restrictor member 130 may be configured as a butterfly valve.

Figure 10:
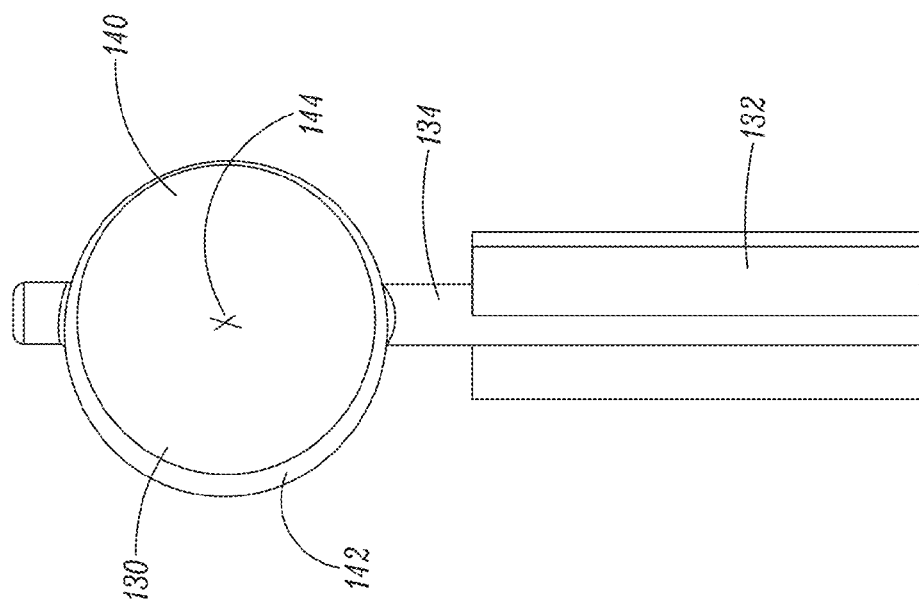
FIG. 10 is a front view of the restrictor member operatively connected to the vane shown in FIG. 8.

Turning to FIG. 10, a front view of the restrictor member 130 and the vane 132 is shown. As previously described, the restrictor member 130 comprises a generally circular face 140 axially offset from the shaft 134. The restrictor member 130 further comprises a second offset designed to facilitate movement of the restrictor member 130 between a closed position and an open position. More specifically, a center 144 of the face 140 of the restrictor member 130 is offset from the plane defined by the radial offset and the shaft 134, or the axis of rotation. In other words, a greater surface area of the face 140 of the restrictor member 130 is positioned on one side of the shaft 134 than on the other side of the shaft 134. Pressure at the chamber inlet 104 derived from exhaled air produces a force acting on the face 140 of the restrictor member 130. Because the center 144 of the face 140 of the restrictor member 130 is offset as described above, a resulting force differential creates a torque about the shaft 134. As further explained below, this torque facilitates movement of the restrictor member 130 between a closed position and an open position.

Figure 11:
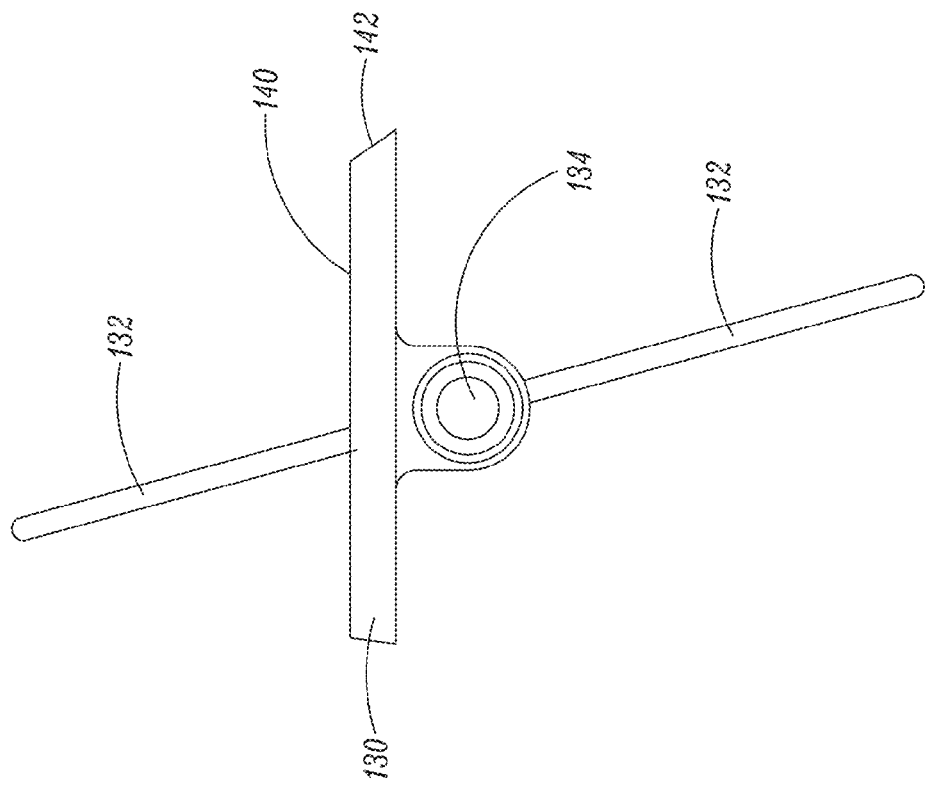
FIG. 11 is a top view of the restrictor member operatively connected to the vane shown in FIG. 8.

Turning to FIG. 11, a top view of the restrictor member 130 and the vane 132 is shown. As illustrated, the vane 132 is connected to the shaft 134 at a 75° angle relative to the face 140 of restrictor member 130. Preferably, the angle will remain between 60° and 80°, although it is envisioned that the angle of the vane 132 may be selectively adjusted to maintain the ideal operating conditions, as previously discussed. It is also preferable that the vane 132 and the restrictor member 130 are configured such that when the OPEP device 100 is fully assembled, the angle between a centerline of the variable nozzle 136 and the vane 132 is between 10° and 25° when the restrictor member 130 is in a closed position. Moreover, regardless of the configuration, it is preferable that the combination of the restrictor member 130 and the vane 132 have a center of gravity aligned with the shaft 134, or the axis of rotation. In full view of the present disclosure, it should be apparent to those skilled in the art that the angle of the vane 132 may be limited by the size or shape of the housing 102, and will generally be less than half the total rotation of the vane 132 and the restrictor member 130.

Figure 13:
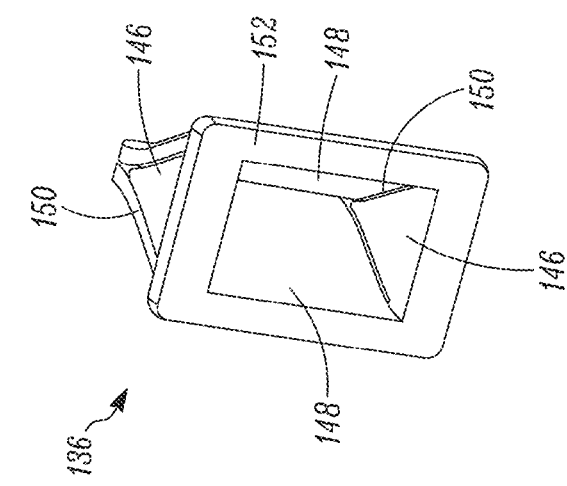
FIG. 13 is a rear perspective view of the variable nozzle of FIG. 12 shown without the flow of exhaled air therethrough.
Figure 12:
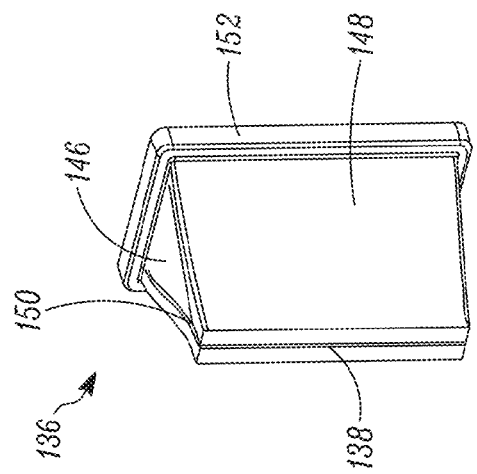
FIG. 12 is a front perspective view of a variable nozzle shown without the flow of exhaled air therethrough.

Turning to FIGS. 12 and 13, a front perspective view and a rear perspective view of the variable nozzle 136 is shown without the flow of exhaled air therethrough. In general, the variable nozzle 136 includes top and bottom walls 146, side walls 148, and V-shaped slits 150 formed therebetween. As shown, the variable nozzle is generally shaped like a duckbill type valve. However, it should be appreciated that nozzles or valves of other shapes and sizes may also be used. The variable nozzle 136 may also include a lip 152 configured to mount the variable nozzle 136 within the housing 102 between the first chamber 114 and the second chamber 118. The variable nozzle 136 may be constructed or molded of any material having a suitable flexibility, such as silicone, and preferably with a wall thickness of between 0.50 and 2.00 millimeters, and an orifice width between 0.25 to 1.00 millimeters, or smaller depending on manufacturing capabilities.

As previously described, the variable nozzle 136 is optional in the operation of the OPEP device 100. It should also be appreciated that the OPEP device 100 could alternatively omit both the chamber passage 116 and the variable nozzle 136, and thus comprise a single-chamber embodiment. Although functional without the variable nozzle 136, the performance of the OPEP device 100 over a wider range of exhalation flow rates is improved when the OPEP device 100 is operated with the variable nozzle 136. The chamber passage 116, when used without the variable nozzle 136, or the orifice 138 of the variable nozzle 136, when the variable nozzle 136 is included, serves to create a jet of exhaled air having an increased velocity. As explained in more detail below, the increased velocity of the exhaled air entering the second chamber 118 results in a proportional increase in the force applied by the exhaled air to the vane 132, and in turn, an increased torque about the shaft 134, all of which affect the ideal operating conditions.

Without the variable nozzle 136, the orifice between the first chamber 114 and the second chamber 118 is fixed according to the size, shape, and cross-sectional area of the chamber passage 116, which may be selectively adjusted by any suitable means, such as replacement of the middle section 103 or the rear section 105 of the housing. On the other hand, when the variable nozzle 136 is included in the OPEP device 100, the orifice between the first chamber 114 and the second chamber 118 is defined by the size, shape, and cross-sectional area of the orifice 138 of the variable nozzle 136, which may vary according to the flow rate of exhaled air and/or the pressure in the first chamber 114.

Figure 14:
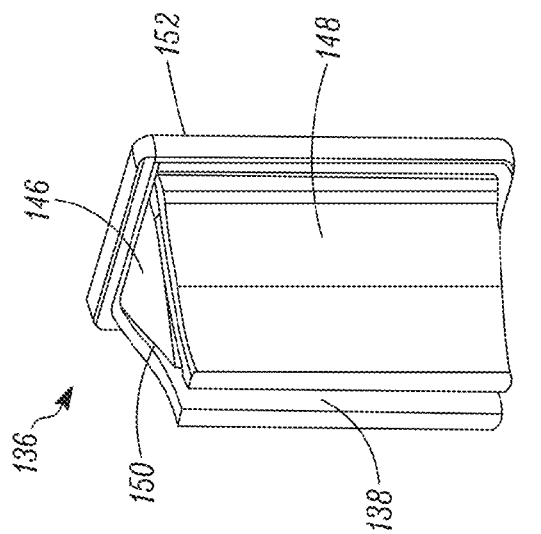
FIG. 14 is a front perspective view of the variable nozzle of FIG. 12 shown with a high flow of exhaled air therethrough.

Turning to FIG. 14, a front perspective view of the variable nozzle 136 is shown with a flow of exhaled air therethrough. One aspect of the variable nozzle 136 shown in FIG. 14 is that, as the orifice 138 opens in response to the flow of exhaled air therethrough, the cross-sectional shape of the orifice 138 remains generally rectangular, which during the administration of OPEP therapy results in a lower drop in pressure through the variable nozzle 136 from the first chamber 114 (See FIGS. 3 and 5) to the second chamber 118. The generally consistent rectangular shape of the orifice 138 of the variable nozzle 136 during increased flow rates is achieved by the V-shaped slits 150 formed between the top and bottom walls 146 and the side walls 148, which serve to permit the side walls 148 to flex without restriction. Preferably, the V-shaped slits 150 are as thin as possible to minimize the leakage of exhaled air therethrough. For example, the V-shaped slits 150 may be approximately 0.25 millimeters wide, but depending on manufacturing capabilities, could range between 0.10 and 0.50 millimeters. Exhaled air that does leak through the V-shaped slits 150 is ultimately directed along the exhalation flow path by the guide walls 120 in the second chamber 118 protruding from the housing 102.

It should be appreciated that numerous factors contribute to the impact the variable nozzle 136 has on the performance of the OPEP device 100, including the geometry and material of the variable nozzle 136. By way of example only, in order to attain a target oscillating pressure frequency of between 10 to 13 Hz at an exhalation flow rate of 15 liters per minute, in one embodiment, a 1.0 by 20.0 millimeter passage or orifice may be utilized. However, as the exhalation flow rate increases, the frequency of the oscillating pressure in that embodiment also increases, though at a rate too quickly in comparison to the target frequency. In order to attain a target oscillating pressure frequency of between 18 to 20 Hz at an exhalation flow rate of 45 liters per minute, the same embodiment may utilize a 3.0 by 20.0 millimeter passage or orifice. Such a relationship demonstrates the desirability of a passage or orifice that expands in cross-sectional area as the exhalation flow rate increases in order to limit the drop in pressure across the variable nozzle 136.

Turning to FIGS. 15A-C, top phantom views of the OPEP device 100 show an exemplary illustration of the operation of the OPEP device 100. Specifically, FIG. 15A shows the restrictor member 130 in an initial, or closed position, where the flow of exhaled air through the chamber inlet 104 is restricted, and the vane 132 is in a first position, directing the flow of exhaled air toward the first chamber outlet 106. FIG. 15B shows this restrictor member 130 in a partially open position, where the flow of exhaled air through the chamber inlet 104 is less restricted, and the vane 132 is directly aligned with the jet of exhaled air exiting the variable nozzle 136. FIG. 15C shows the restrictor member 130 in an open position, where the flow of exhaled air through the chamber inlet 104 is even less restricted, and the vane 132 is in a second position, directing the flow of exhaled air toward the second chamber outlet 108. It should be appreciated that the cycle described below is merely exemplary of the operation of the OPEP device 100, and that numerous factors may affect operation of the OPEP device 100 in a manner that results in a deviation from the described cycle. However, during the operation of the OPEP device 100, the restrictor member 130 and the vane 132 will generally reciprocate between the positions shown in FIGS. 15A and 15C.

During the administration of OPEP therapy, the restrictor member 130 and the vane 132 may be initially positioned as shown in FIG. 15A. In this position, the restrictor member 130 is in a closed position, where the flow of exhaled air along the exhalation path through the chamber inlet 104 is substantially restricted. As such, an exhalation pressure at the chamber inlet 104 begins to increase when a user exhales into the mouthpiece 108. As the exhalation pressure at the chamber inlet 104 increases, a corresponding force acting on the face 140 of the restrictor member 130 increases. As previously explained, because the center 144 of the face 140 is offset from the plane defined by the radial offset and the shaft 134, a resulting net force creates a negative or opening torque about the shaft. In turn, the opening torque biases the restrictor member 130 to rotate open, letting exhaled air enter the first chamber 114, and biases the vane 132 away from its first position. As the restrictor member 130 opens and exhaled air is let into the first chamber 114, the pressure at the chamber inlet 104 begins to decrease, the force acting on the face 140 of the restrictor member begins to decrease, and the torque biasing the restrictor member 130 open begins to decrease.

As exhaled air continues to enter the first chamber 114 through the chamber inlet 104, it is directed along the exhalation flow path 110 by the housing 102 until it reaches the chamber passage 116 disposed between the first chamber 114 and the second chamber 118. If the OPEP device 100 is being operated without the variable nozzle 136, the exhaled air accelerates through the chamber passage 116 due to the decrease in cross-sectional area to form a jet of exhaled air. Likewise, if the OPEP device 100 is being operated with the variable nozzle 136, the exhaled air accelerates through the orifice 138 of the variable nozzle 136, where the pressure through the orifice 138 causes the side walls 148 of the variable nozzle 136 to flex outward, thereby increasing the size of the orifice 138, as well as the resulting flow of exhaled air therethrough. To the extent some exhaled air leaks out of the V-shaped slits 150 of the variable nozzle 136, it is directed back toward the jet of exhaled air and along the exhalation flow path by the guide walls 120 protruding into the housing 102.

Then, as the exhaled air exits the first chamber 114 through the variable nozzle 136 and/or chamber passage 116 and enters the second chamber 118, it is directed by the vane 132 toward the front section 101 of the housing 102, where it is forced to reverse directions before exiting the OPEP device 100 through the open first chamber exit 106. As a result of the change in direction of the exhaled air toward the front section 101 of the housing 102, a pressure accumulates in the second chamber 118 near the front section 101 of the housing 102, thereby resulting in a force on the adjacent vane 132, and creating an additional negative or opening torque about the shaft 134. The combined opening torques created about the shaft 134 from the forces acting on the face 140 of the restrictor member 130 and the vane 132 cause the restrictor member 130 and the vane 132 to rotate about the shaft 134 from the position shown in FIG. 15A toward the position shown in FIG. 15B.

When the restrictor member 130 and the vane 132 rotate to the position shown in FIG. 15B, the vane 132 crosses the jet of exhaled air exiting the variable nozzle 136 or the chamber passage 116. Initially, the jet of exhaled air exiting the variable nozzle 136 or chamber passage 116 provides a force on the vane 132 that, along with the momentum of the vane 132, the shaft 134, and the restrictor member 130, propels the vane 132 and the restrictor member 130 to the position shown in FIG. 15C. However, around the position shown in FIG. 15B, the force acting on the vane 132 from the exhaled air exiting the variable nozzle 136 also switches from a negative or opening torque to a positive or closing torque. More specifically, as the exhaled air exits the first chamber 114 through the variable nozzle 136 and enters the second chamber 118, it is directed by the vane 132 toward the front section 101 of the housing 102, where it is forced to reverse directions before exiting the OPEP device 100 through the open second chamber exit 108. As a result of the change in direction of the exhaled air toward the front section 101 of the housing 102, a pressure accumulates in the second chamber 118 near the front section 101 of the housing 102, thereby resulting in a force on the adjacent vane 132, and creating a positive or closing torque about the shaft 134. As the vane 132 and the restrictor member 130 continue to move closer to the position shown in FIG. 15C, the pressure accumulating in the section chamber 118 near the front section 101 of the housing 102, and in turn, the positive or closing torque about the shaft 134, continues to increase, as the flow of exhaled air along the exhalation flow path 110 and through the chamber inlet 104 is even less restricted. Meanwhile, although the torque about the shaft 134 from the force acting on the restrictor member 130 also switches from a negative or opening torque to a positive or closing torque around the position shown in FIG. 15B, its magnitude is essentially negligible as the restrictor member 130 and the vane 132 rotate from the position shown in FIG. 15B to the position shown in FIG. 15C.

After reaching the position shown in FIG. 15C, and due to the increased positive or closing torque about the shaft 134, the vane 132 and the restrictor member 130 reverse directions and begin to rotate back toward the position shown in FIG. 15B. As the vane 132 and the restrictor member 130 approach the position shown in FIG. 15B, and the flow of exhaled through the chamber inlet 104 is increasingly restricted, the positive or closing torque about the shaft 134 begins to decrease. When the restrictor member 130 and the vane 132 reach the position 130 shown in FIG. 15B, the vane 132 crosses the jet of exhaled air exiting the variable nozzle 136 or the chamber passage 116, thereby creating a force on the vane 132 that, along with the momentum of the vane 132, the shaft 134, and the restrictor member 130, propels the vane 132 and the restrictor member 130 back to the position shown in FIG. 15A. After the restrictor member 130 and the vane 132 return to the position shown in FIG. 15A, the flow of exhaled air through the chamber inlet 104 is restricted, and the cycle described above repeats itself.

It should be appreciated that, during a single period of exhalation, the cycle described above will repeat numerous times. Thus, by repeatedly moving the restrictor member 130 between a closed position, where the flow of exhaled air through the chamber inlet 104 is restricted, and an open position, where the flow of exhaled air through the chamber inlet 104 is less restricted, an oscillating back pressure is transmitted to the user of the OPEP device 100 and OPEP therapy is administered.

Figure 17:
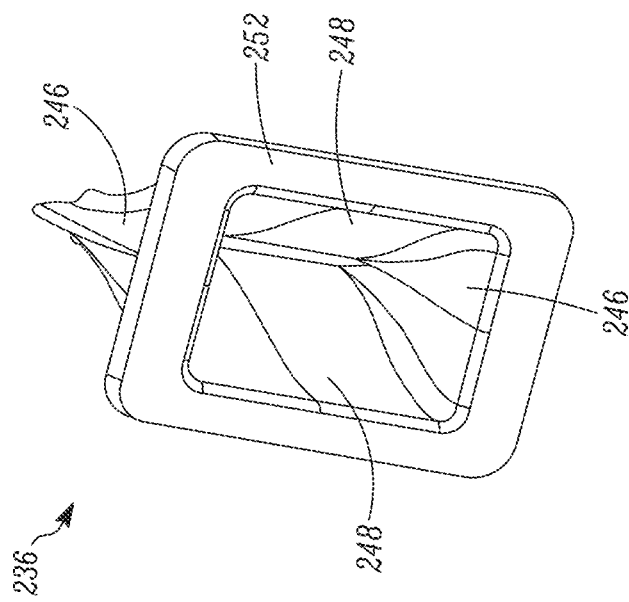
FIG. 17 is a rear perspective view of the variable nozzle of FIG. 16 shown without the flow of exhaled air therethrough.
Figure 16:
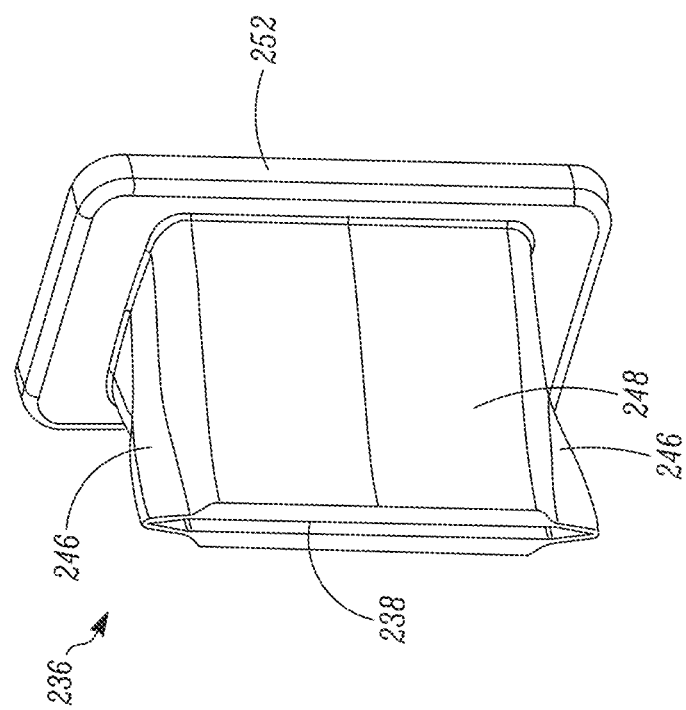
FIG. 16 is a front perspective view of a different embodiment of a variable nozzle shown without the flow of exhaled air therethrough.

Turning now to FIGS. 16-17, an alternative embodiment of a variable nozzle 236 is shown. The variable nozzle 236 may be used in the OPEP device 100 as an alternative to the variable nozzle 136 described above. As shown in FIGS. 16-17, the variable nozzle 236 includes an orifice 238, top and bottom walls 246, side walls 248, and a lip 252 configured to mount the variable nozzle 236 within the housing of the OPEP device 100 between the first chamber 114 and the second chamber 118 in the same manner as the variable nozzle 136. Similar to the variable nozzle 136 shown in FIGS. 12-13, the variable nozzle 236 may be constructed or molded of any material having a suitable flexibility, such as silicone.

During the administration of OPEP therapy, as the orifice 238 of the variable nozzle 236 opens in response to the flow of exhaled air therethrough, the cross-sectional shape of the orifice 238 remains generally rectangular, which results in a lower drop in pressure through the variable nozzle 236 from the first chamber 114 to the second chamber 118. The generally consistent rectangular shape of the orifice 238 of the variable nozzle 236 during increased flow rates is achieved by thin, creased walls formed in the top and bottom walls 246, which allow the side walls 248 to flex easier and with less resistance. A further advantage of this embodiment is that there is no leakage out of the top and bottom walls 246 while exhaled air flows through the orifice 238 of the variable nozzle 236, such as for example, through the V-shaped slits 150 of the variable nozzle 136 shown in FIGS. 12-13.

Those skilled in the art will also appreciate that, in some applications, only positive expiratory pressure (without oscillation) may be desired, in which case the OPEP device 100 may be operated without the restrictor member 130, but with a fixed orifice or manually adjustable orifice instead. The positive expiratory pressure embodiment may also comprise the variable nozzle 136, or the variable nozzle 236, in order to maintain a relatively consistent back pressure within a desired range.

Second Embodiment

Figure 18:
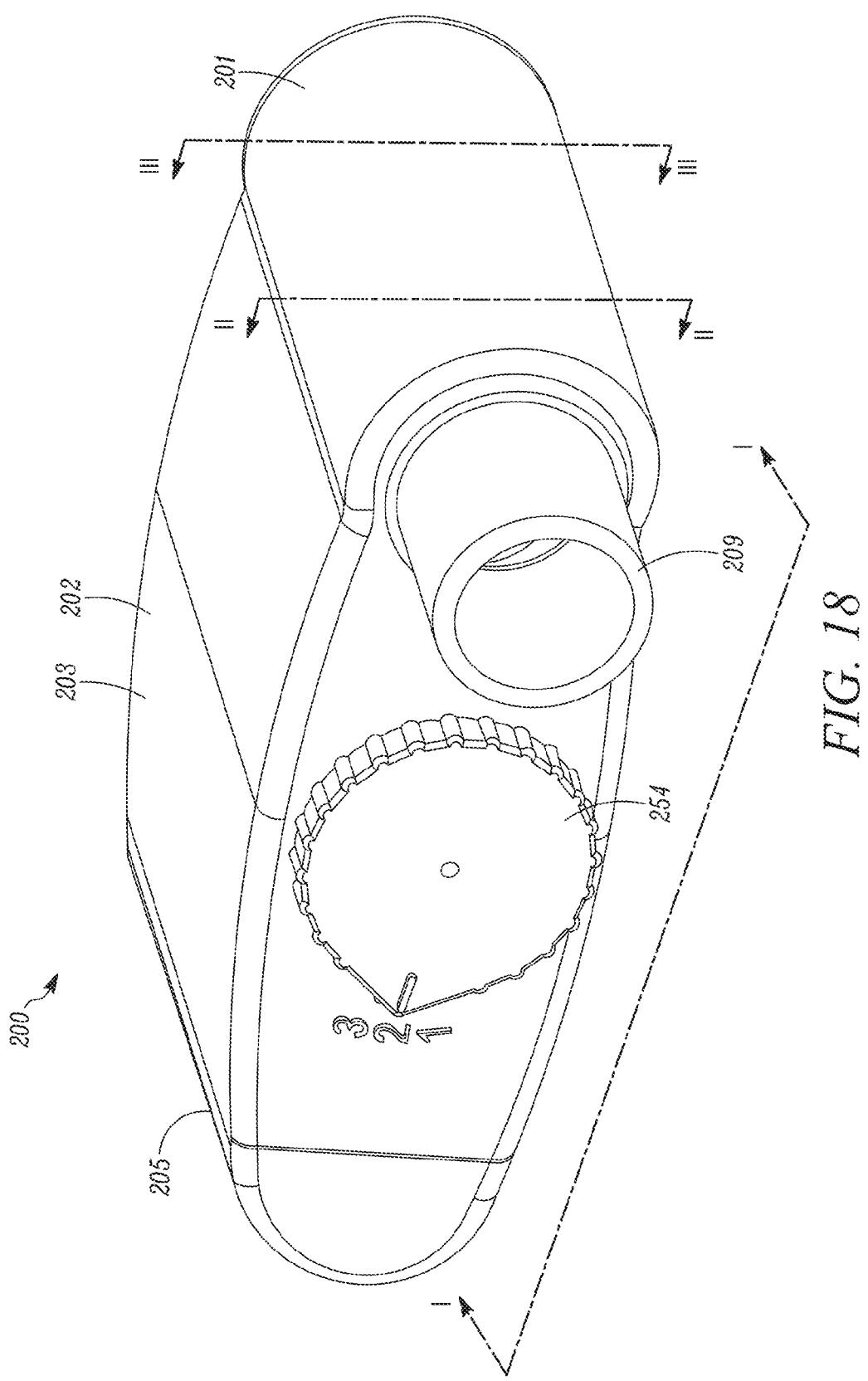
FIG. 18 is a front perspective view of a second embodiment of an OPEP device.
Figure 19:
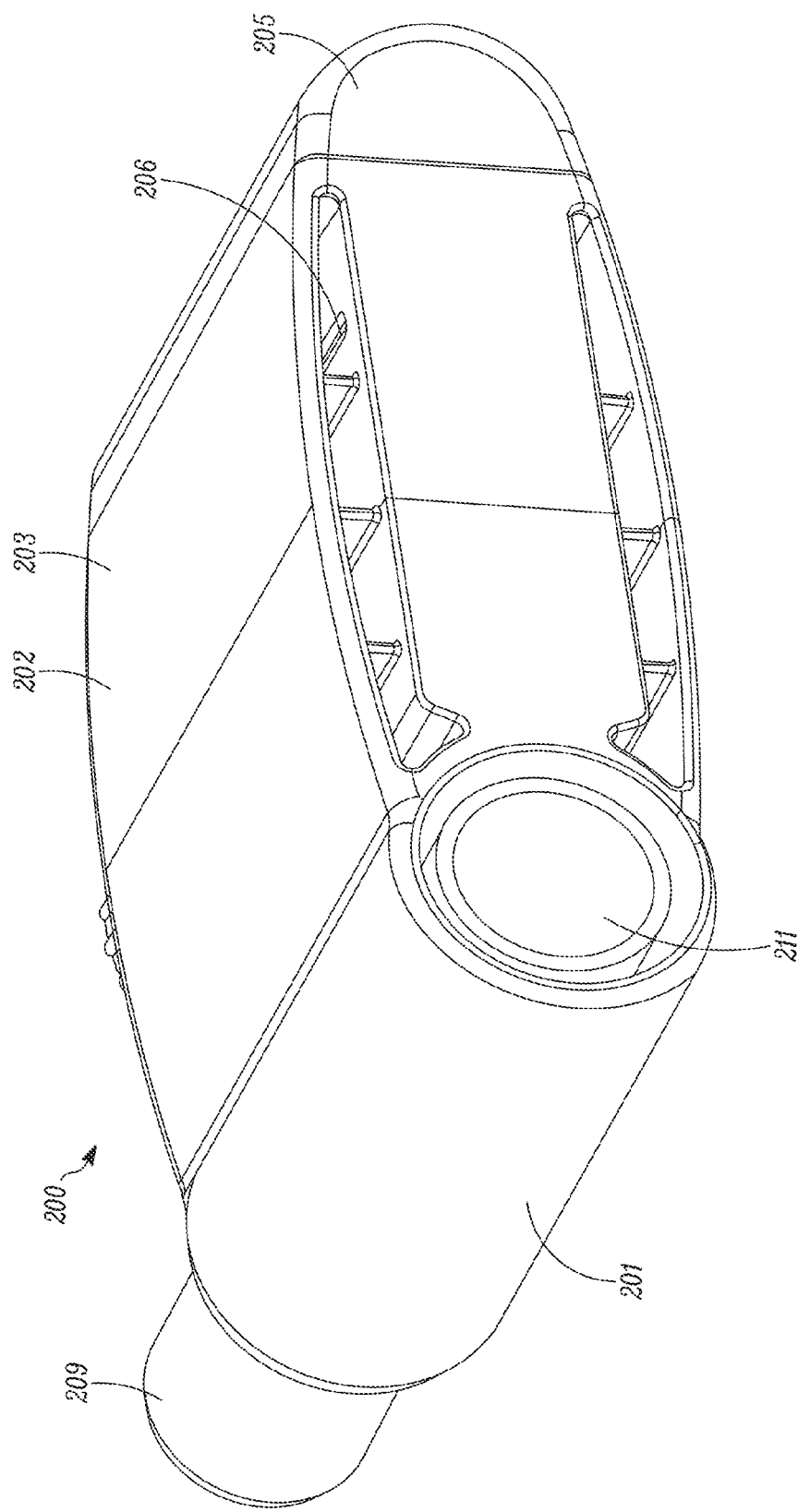
FIG. 19 is a rear perspective view of the OPEP device of FIG. 18.

Turning now to FIGS. 18-19, a front perspective view and a rear perspective view of a second embodiment of an OPEP device 200 is shown. The configuration and operation of the OPEP device 200 is similar to that of the OPEP device 100. However, as best shown in FIGS. 20-24, the OPEP device 200 further includes an adjustment mechanism 253 adapted to change the relative position of the chamber inlet 204 with respect to the housing 202 and the restrictor member 230, which in turn changes the range of rotation of the vane 232 operatively connected thereto. As explained below, a user is therefore able to conveniently adjust both the frequency and the amplitude of the OPEP therapy administered by the OPEP device 200 without opening the housing 202 and disassembling the components of the OPEP device 200.

The OPEP device 200 generally comprises a housing 202, a chamber inlet 204, a first chamber outlet 206 (best seen in FIGS. 23 and 32), a second chamber outlet 208 (best seen in FIGS. 23 and 32), and a mouthpiece 209 in fluid communication with the chamber inlet 204. As with the OPEP device 100, a front section 201, a middle section 203, and a rear section 205 of the housing 202 are separable so that the components contained therein can be periodically accessed, cleaned, replaced, or reconfigured, as required to maintain the ideal operating conditions. The OPEP device also includes an adjustment dial 254, as described below.

As discussed above in relation to the OPEP device 100, the OPEP device 200 may be adapted for use with other or additional interfaces, such as an aerosol delivery device. In this regard, the OPEP device 200 is equipped with an inhalation port 211 (best seen in FIGS. 19, 21, and 23) in fluid communication with the mouthpiece 209 and the chamber inlet 204. As noted above, the inhalation port may include a separate one-way valve (not shown) to permit a user of the OPEP device 200 both to inhale the surrounding air through the one-way valve and to exhale through the chamber inlet 204 without withdrawing the mouthpiece 209 of the OPEP device 200 between periods of inhalation and exhalation. In addition, the aforementioned aerosol delivery devices may be connected to the inhalation port 211 for the simultaneous administration of aerosol and OPEP therapies.

Figure 20:
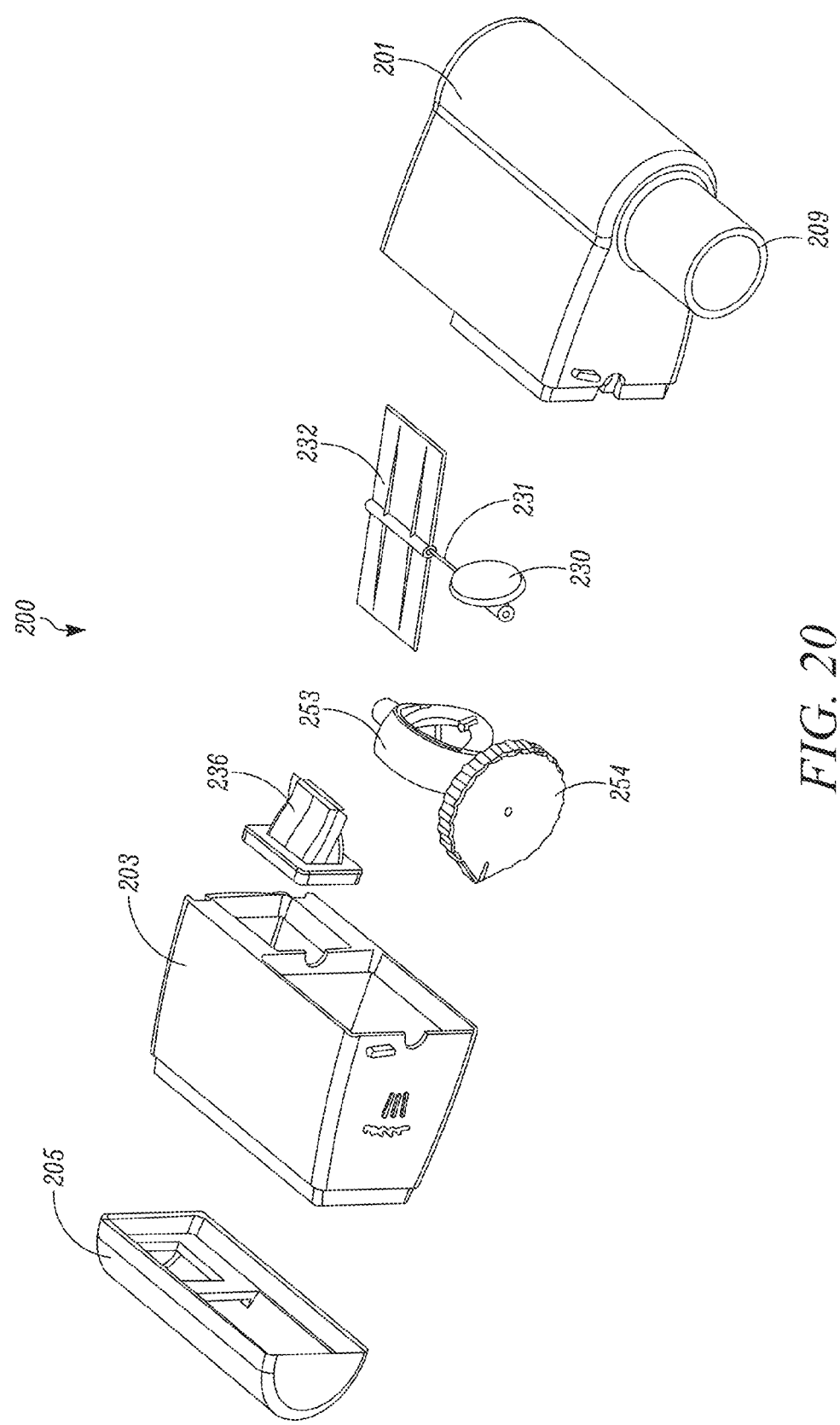
FIG. 20 is an exploded view of the OPEP device of FIG. 18, shown with the internal components of the OPEP device.

An exploded view of the OPEP device 200 is shown in FIG. 20. In addition to the components of the housing described above, the OPEP device 200 includes a restrictor member 230 operatively connected to a vane 232 by a pin 231, an adjustment mechanism 253, and a variable nozzle 236. As shown in the cross-sectional view of FIG. 21, when the OPEP device 200 is in use, the variable nozzle 236 is positioned between the middle section 203 and the rear section 205 of the housing 202, and the adjustment mechanism 253, the restrictor member 230, and the vane 232 form an assembly.

Figure 21:
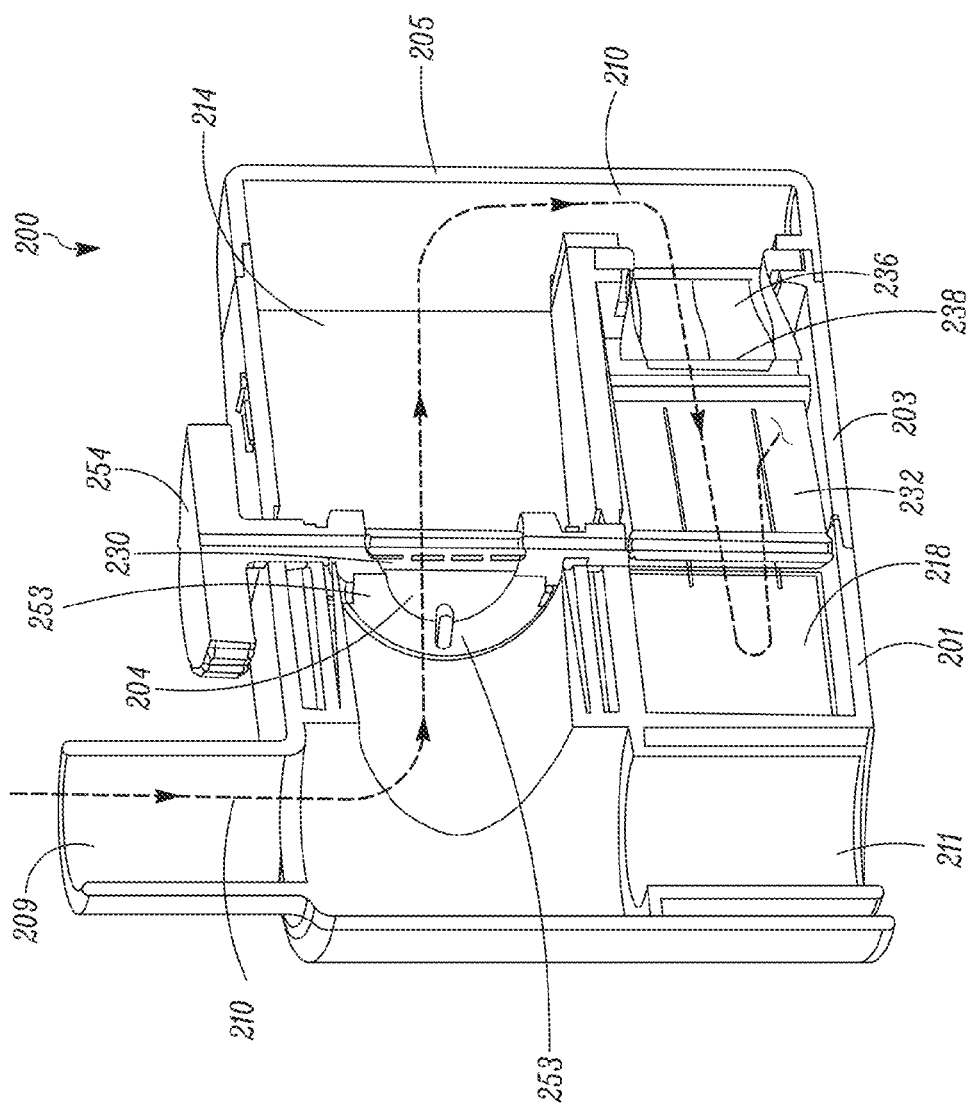
FIG. 21 is a cross-sectional view taken along line I in FIG. 18 of the OPEP device, shown with the internal components of the OPEP device.
Figure 22:
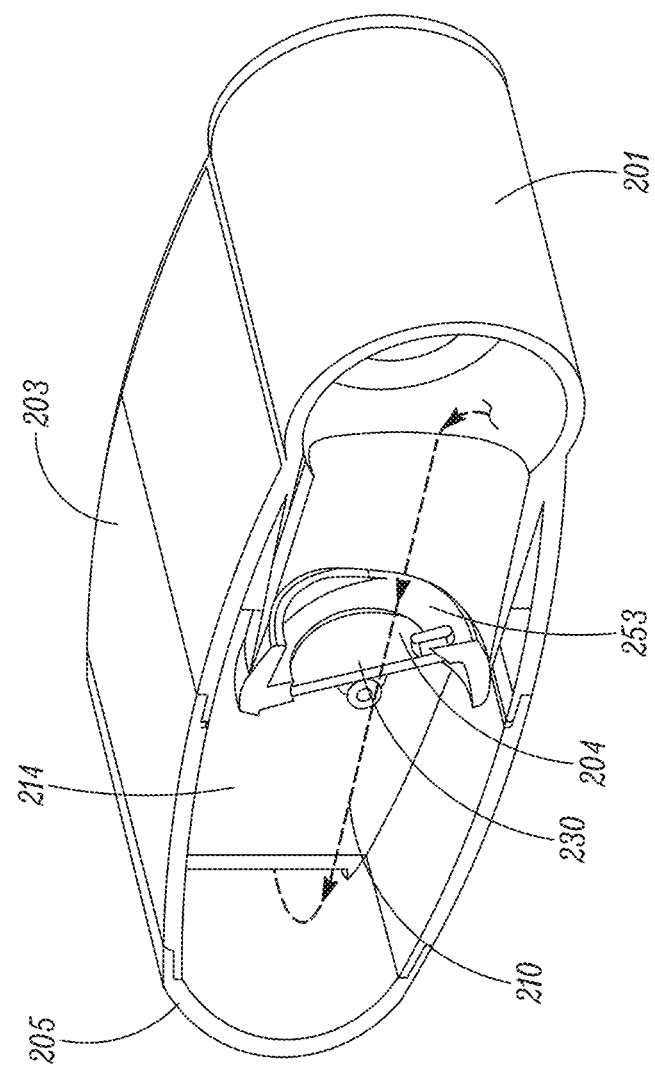
FIG. 22 is a cross-sectional view taken along line II in FIG. 18 of the OPEP device, shown with the internal components of the OPEP device.
Figure 23:
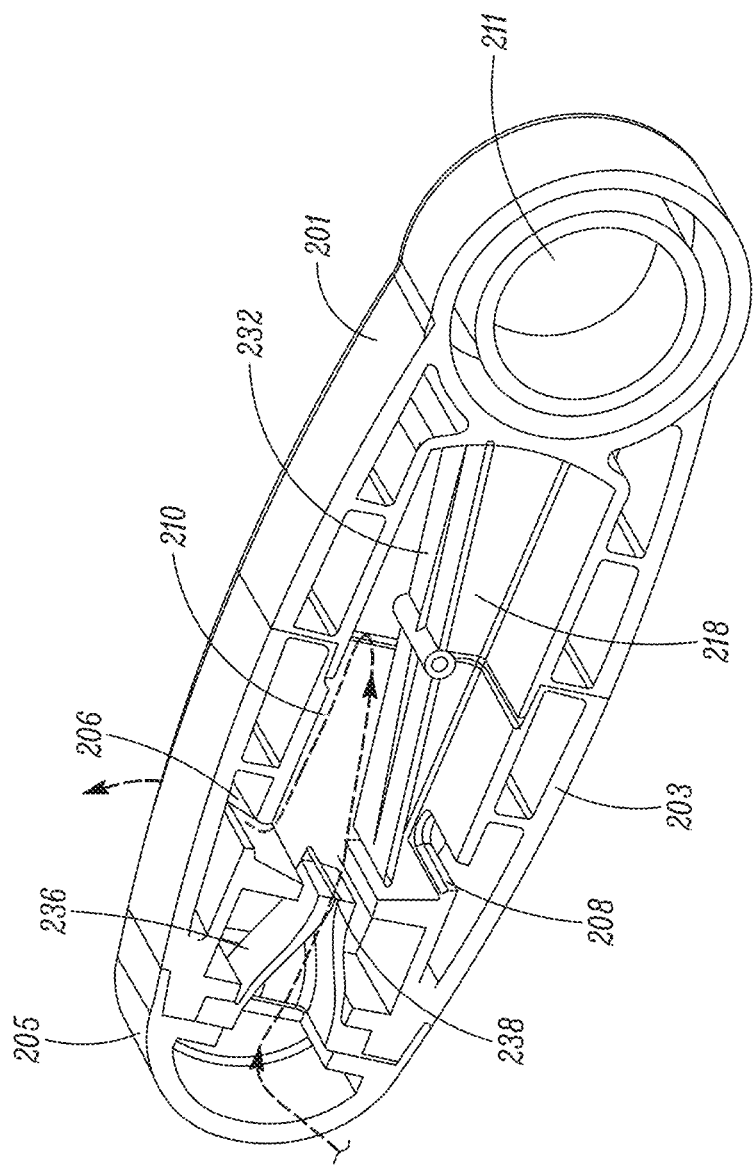
FIG. 23 is a cross-sectional view taken along line III in FIG. 18 of the OPEP device, shown with the internal components of the OPEP device.

Turning to FIGS. 21-23, various cross-sectional perspective views of the OPEP device 200 are shown. As with the OPEP device 100, an exhalation flow path 210, identified by a dashed line, is defined between the mouthpiece 209 and at least one of the first chamber outlet 206 and the second chamber outlet 208 (best seen in FIGS. 23 and 32). As a result of a one-way valve (not-shown) and/or an aerosol delivery device (not shown) attached to the inhalation port 211, the exhalation flow path 210 begins at the mouthpiece 209 and is directed toward the chamber inlet 204, which in operation may or may not be blocked by the restrictor member 230. After passing through the chamber inlet 204, the exhalation flow path 210 enters a first chamber 214 and makes a 180° turn toward the variable nozzle 236. After passing through the orifice 238 of the variable nozzle 236, the exhalation flow path 210 enters a second chamber 218. In the second chamber 218, the exhalation flow path 210 may exit the OPEP device 200 through at least one of the first chamber outlet 206 or the second chamber outlet 208. Those skilled in the art will appreciate that the exhalation flow path 210 identified by the dashed line is exemplary, and that air exhaled into the OPEP device 200 may flow in any number of directions or paths as it traverses from the mouthpiece 209 or chamber inlet 204 to the first chamber outlet 206 or the second chamber outlet 208.

Figure 25:
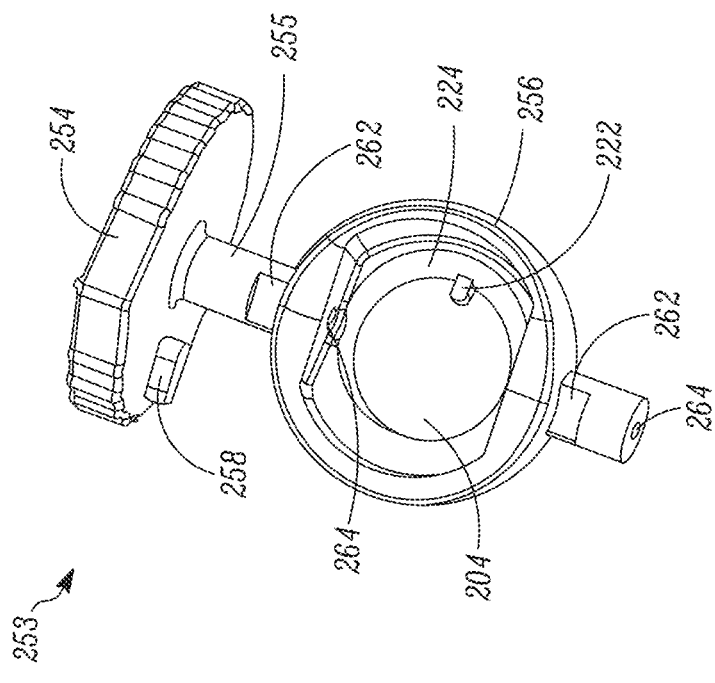
FIG. 25 is a rear perspective view of the adjustment mechanism of FIG. 24.
Figure 24:
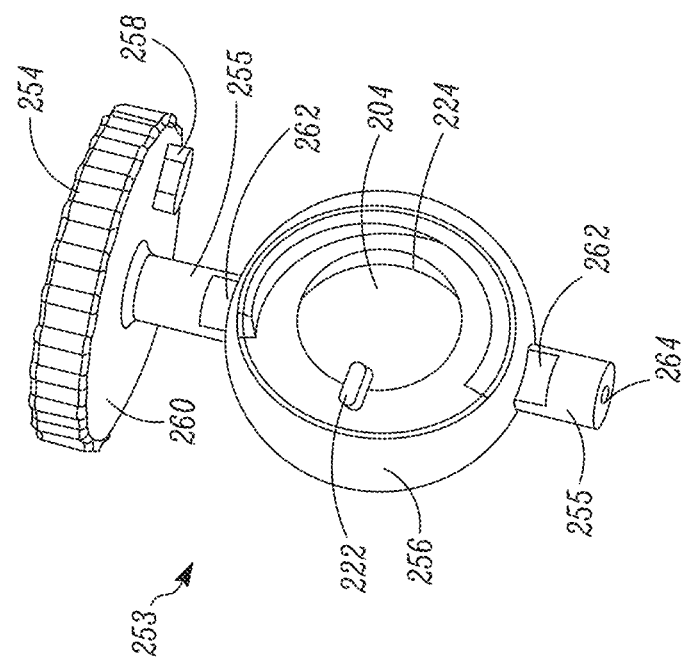
FIG. 24 is a front perspective view of an adjustment mechanism of the OPEP device of FIG. 18.

Referring to FIGS. 24-25, front and rear perspective views of the adjustment mechanism 253 of the OPEP device 200 are shown. In general, the adjustment mechanism 253 includes an adjustment dial 254, a shaft 255, and a frame 256. A protrusion 258 is positioned on a rear face 260 of the adjustment dial, and is adapted to limit the selective rotation of the adjustment mechanism 253 by a user, as further described below. The shaft 255 includes keyed portions 262 adapted to fit within upper and lower bearings 226, 228 formed in the housing 200 (see FIGS. 21 and 28-29). The shaft further includes an axial bore 264 configured to receive the pin 231 operatively connecting the restrictor member 230 and the vane 232. As shown, the frame 256 is spherical, and as explained below, is configured to rotate relative to the housing 202, while forming a seal between the housing 202 and the frame 256 sufficient to permit the administration of OPEP therapy. The frame 256 includes a circular opening defined by a seat 224 adapted to accommodate the restrictor member 230. In use, the circular opening functions as the chamber inlet 204. The frame 256 also includes a stop 222 for preventing the restrictor member 230 from opening in a wrong direction.

Figure 26:
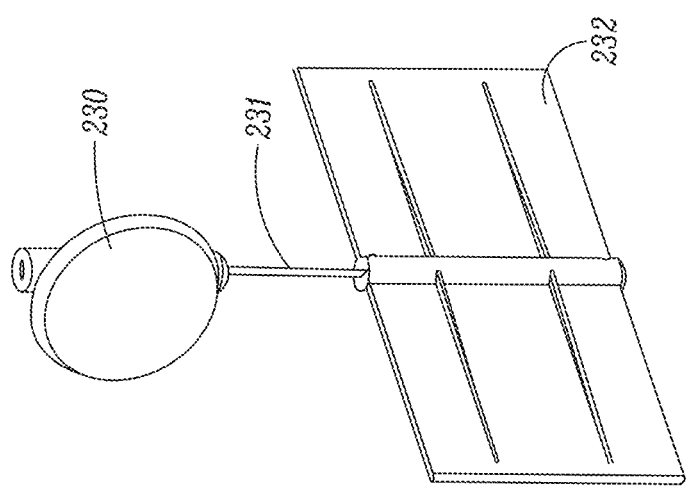
FIG. 26 is a front perspective view of a restrictor member operatively connected to a vane for use in the OPEP device of FIG. 18.

Turning to FIG. 26, a front perspective view of the restrictor member 230 and the vane 232 is shown. The design, materials, and configuration of the restrictor member 230 and the vane 232 may be the same as described above in regards to the OPEP device 100. However, the restrictor member 230 and the vane 232 in the OPEP device 200 are operatively connected by a pin 231 adapted for insertion through the axial bore 264 in the shaft 255 of the adjustment mechanism 253. The pin 231 may be constructed, for example, by stainless steel. In this way, rotation of the restrictor member 230 results in a corresponding rotation of the vane 232, and vice versa.

Figure 27:
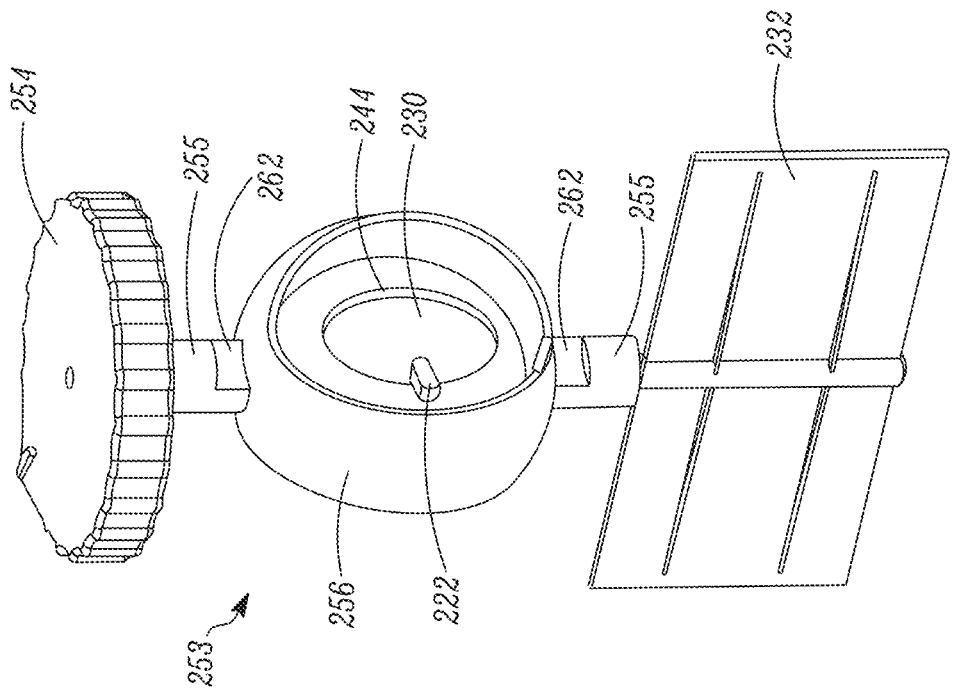
FIG. 27 is a front perspective view of the adjustment mechanism of FIG. 24 assembled with the restrictor member and the vane of FIG. 26.

Turning to FIG. 27, a front perspective view of the adjustment mechanism 253 assembled with the restrictor member 230 and the vane 232 is shown. In this configuration, it can be seen that the restrictor member 230 is positioned such that it is rotatable relative to the frame 256 and the seat 224 between a closed position (as shown), where a flow of exhaled air along the exhalation flow path 210 through the chamber inlet 204 is restricted, and an open position (not shown), where the flow of exhaled air through the chamber inlet 204 is less restricted. As previously mentioned the vane 232 is operatively connected to the restrictor member 230 by the pin 231 extending through shaft 255, and is adapted to move in unison with the restrictor member 230. It can further be seen that the restrictor member 230 and the vane 232 are supported by the adjustment mechanism 253, which itself is rotatable within the housing 202 of the OPEP device 200, as explained below.

Figure 28:
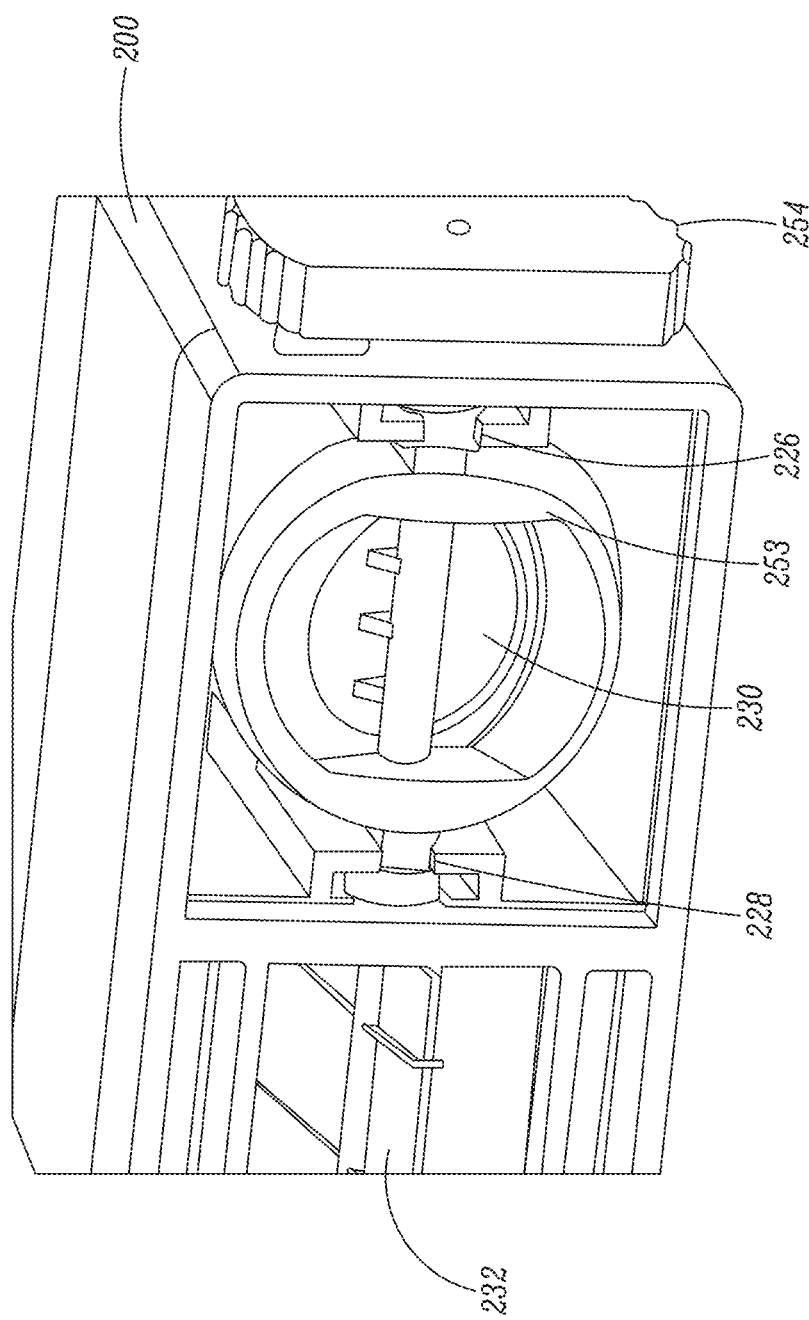
FIG. 28 is a partial cross-sectional view of the assembly of FIG. 27 within the OPEP device of FIG. 18.
Figure 29B:
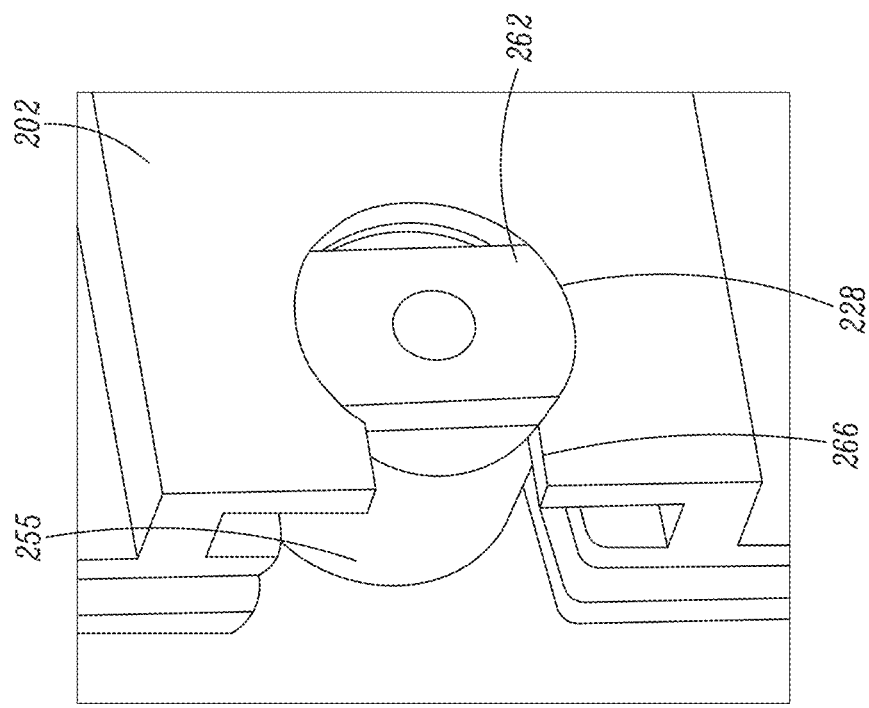
FIGS. 29A-B are partial cross-sectional views illustrating installation of the assembly of FIG. 27 within the OPEP device of FIG. 18.
Figure 29A:
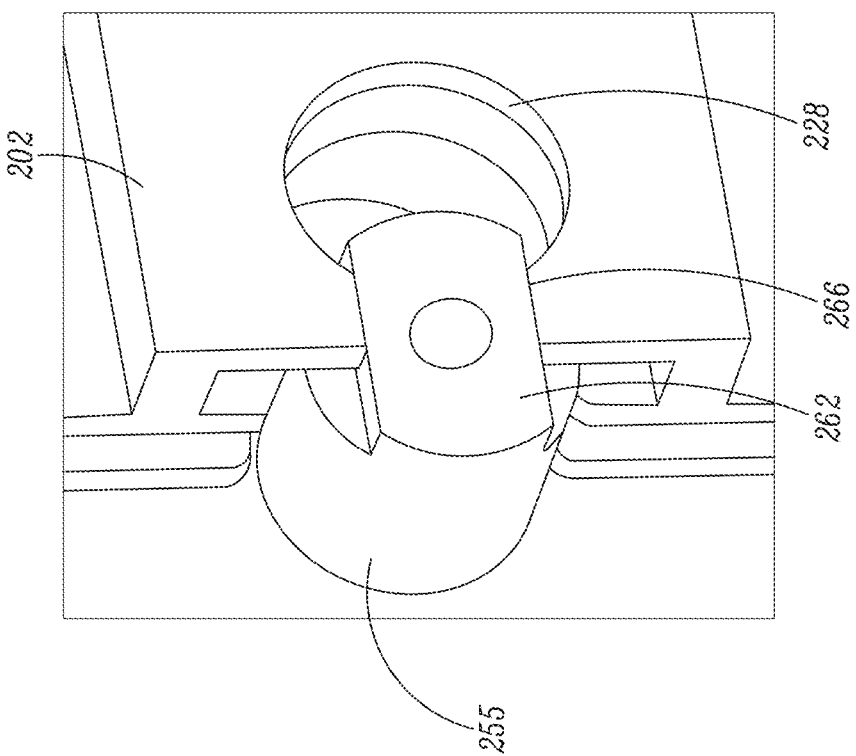

FIGS. 28 and 29A-B are partial cross-sectional views illustrating the adjustment mechanism 253 mounted within the housing 202 of the OPEP device 200. As shown in FIG. 28, the adjustment mechanism 253, as well as the restrictor member 230 and the vane 232, are rotatably mounted within the housing 200 about an upper and lower bearing 226, 228, such that a user is able to rotate the adjustment mechanism 253 using the adjustment dial 254. FIGS. 29A-29B further illustrates the process of mounting and locking the adjustment mechanism 253 within the lower bearing 228 of the housing 202. More specifically, the keyed portion 262 of the shaft 255 is aligned with and inserted through a rotational lock 166 formed in the housing 202, as shown in FIG. 29A. Once the keyed portion 262 of the shaft 255 is inserted through the rotational lock 266, the shaft 255 is rotated 90° to a locked position, but remains free to rotate. The adjustment mechanism 253 is mounted and locked within the upper bearing 226 in the same manner.

Figure 30:
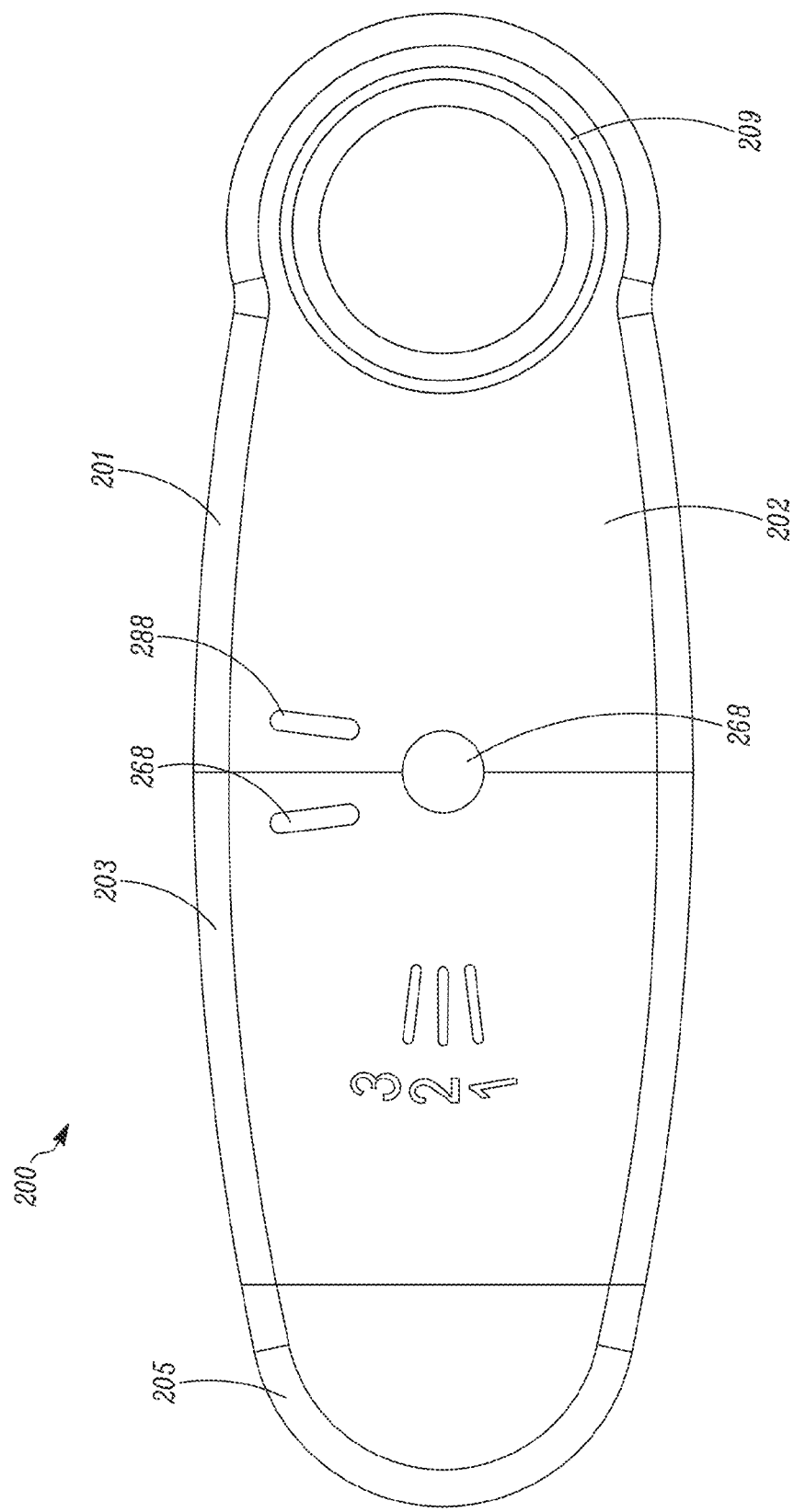
FIG. 30 is a front view of the OPEP device of FIG. 18 illustrating an aspect of the adjustability of the OPEP device.

Once the housing 200 and the internal components of the OPEP device 200 are assembled, the rotation of the shaft 255 is restricted to keep it within a locked position in the rotational lock 166. As shown in a front view of the OPEP device 200 in FIG. 30, two stops 268, 288 are positioned on the housing 202 such that they engage the protrusion 258 formed on the rear face 260 of the adjustment dial 254 when a user rotates the adjustment dial 254 to a predetermined position. For purposes of illustration, the OPEP device 200 is shown in FIG. 30 without the adjustment dial 254 or the adjustment mechanism 253, which would extend from the housing 202 through an opening 269. In this way, rotation of the adjustment dial 254, the adjustment mechanism 253, and the keyed portion 262 of the shaft 255 can be appropriately restricted.

Figure 31:
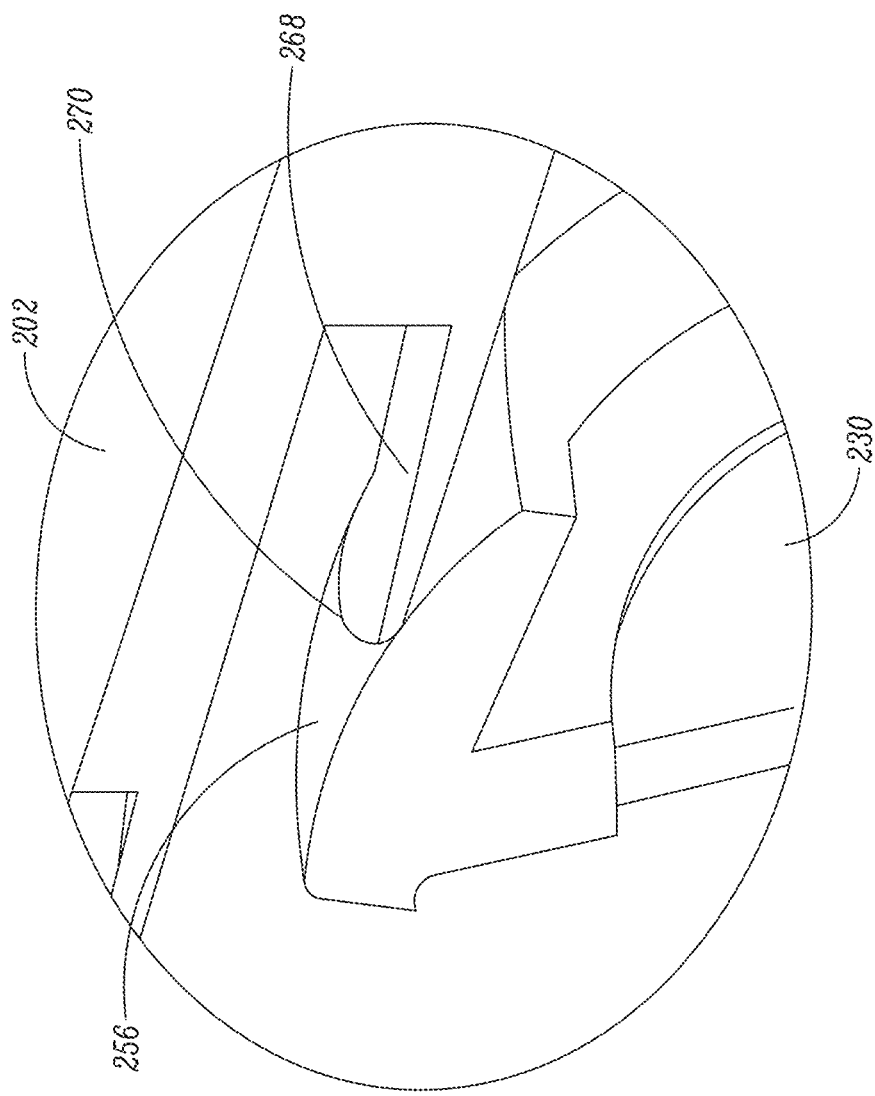
FIG. 31 is a partial cross-sectional view of the assembly of FIG. 27 within the OPEP device of FIG. 18.

Turning to FIG. 31, a partial cross-sectional view of the adjustment mechanism 253 mounted within the housing 200 is shown. As previously mentioned, the frame 256 of the adjustment mechanism 253 is spherical, and is configured to rotate relative to the housing 202, while forming a seal between the housing 202 and the frame 256 sufficient to permit the administration of OPEP therapy. As shown in FIG. 31, a flexible cylinder 271 extending from the housing 202 completely surrounds a portion of the frame 256 to form a sealing edge 270. Like the housing 202 and the restrictor member 230, the flexible cylinder 271 and the frame 256 may be constructed of a low shrink, low friction plastic. One such material is acetal. In this way, the sealing edge 270 contacts the frame 256 for a full 360° and forms a seal throughout the permissible rotation of the adjustment member 253.

The selective adjustment of the OPEP device 200 will now be described with reference to FIGS. 32A-B, 33A-B, and 34A-B. FIGS. 32A-B are partial cross-sectional views of the OPEP device 200; FIGS. 33A-B are illustrations of the adjustability of the OPEP device 200; and, FIGS. 34A-B are top phantom views of the OPEP device 200. As previously mentioned with regards to the OPEP device 100, it is preferable that the vane 232 and the restrictor member 230 are configured such that when the OPEP device 200 is fully assembled, the angle between a centerline of the variable nozzle 236 and the vane 232 is between 10° and 25° when the restrictor member 230 is in a closed position. However, it should be appreciated that the adjustability of the OPEP device 200 is not limited to the parameters described herein, and that any number of configurations may be selected for purposes of administering OPEP therapy within the ideal operating conditions.

FIG. 32A shows the vane 232 at an angle of 10° from the centerline of the variable nozzle 236, whereas FIG. 32B shows the vane 232 at an angle of 25° from the centerline of the variable nozzle 236. FIG. 33A illustrates the necessary position of the frame 256 (shown in phantom) relative to the variable nozzle 236 such that the angle between a centerline of the variable nozzle 236 and the vane 232 is 10° when the restrictor member 230 is in the closed position. FIG. 33B, on the other hand, illustrates the necessary position of the frame 256 (shown in phantom) relative to the variable nozzle 236 such that the angle between a centerline of the variable nozzle 236 and the vane 232 is 25° when the restrictor member 230 is in the closed position.

Referring to FIGS. 34A-B, side phantom views of the OPEP device 200 are shown. The configuration shown in FIG. 34A corresponds to the illustrations shown in FIGS. 32A and 33A, wherein the angle between a centerline of the variable nozzle 236 and the vane 232 is 10° when the restrictor member 230 is in the closed position. FIG. 34B, on the other hand, corresponds to the illustrations shown in FIGS. 32B and 33B, wherein the angle between a centerline of the variable nozzle 236 and the vane 232 is 25° when the restrictor member 230 is in the closed position. In other words, the frame 256 of the adjustment member 253 has been rotated counter-clockwise 15°, from the position shown in FIG. 34A, to the position shown in FIG. 34B, thereby also increasing the permissible rotation of the vane 232.

In this way, a user is able to rotate the adjustment dial 254 to selectively adjust the orientation of the chamber inlet 204 relative to the restrictor member 230 and the housing 202. For example, a user may increase the frequency and amplitude of the OPEP therapy administered by the OPEP device 200 by rotating the adjustment dial 254, and therefore the frame 256, toward the position shown in FIG. 34A. Alternatively, a user may decrease the frequency and amplitude of the OPEP therapy administered by the OPEP device 200 by rotating the adjustment dial 254, and therefore the frame 256, toward the position shown in FIG. 34B. Furthermore, as shown for example in FIGS. 18 and 30, indicia may be provided to aid the user in the setting of the appropriate configuration of the OPEP device 200.

Operating conditions similar to those described below with reference to the OPEP device 800 may also be achievable for an OPEP device according to the OPEP device 200.

Third Embodiment

Figure 35:
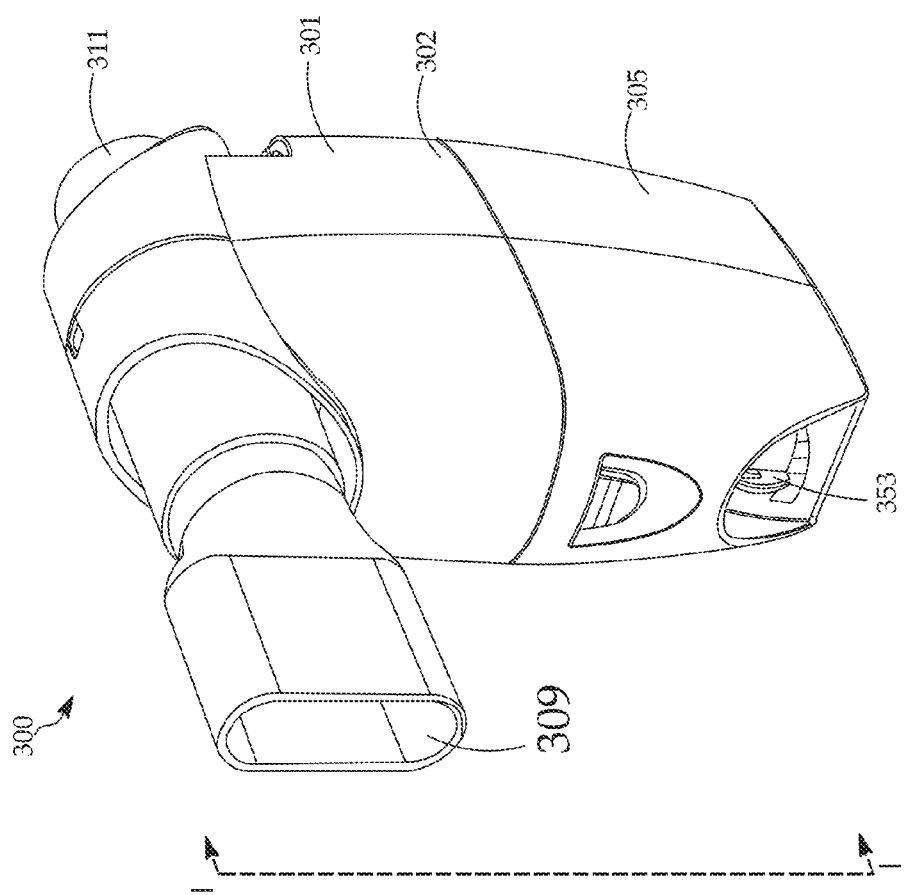
FIG. 35 is a front perspective view of another embodiment of an OPEP device.
Figure 36:
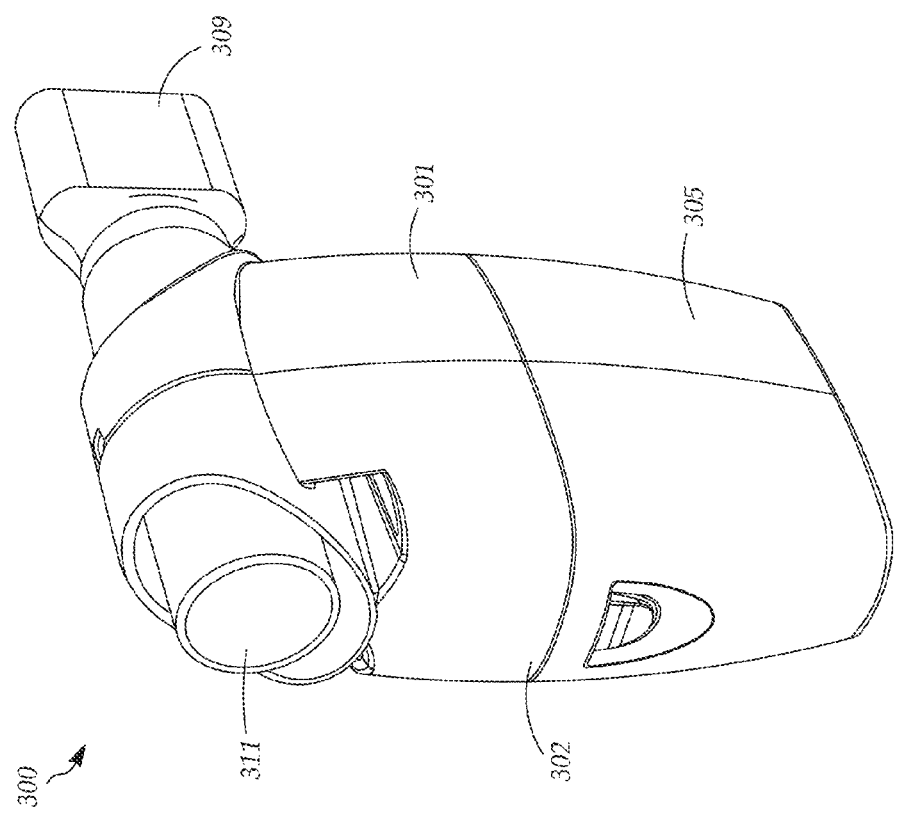
FIG. 36 is a rear perspective view of the OPEP device of FIG. 35.
Figure 37:
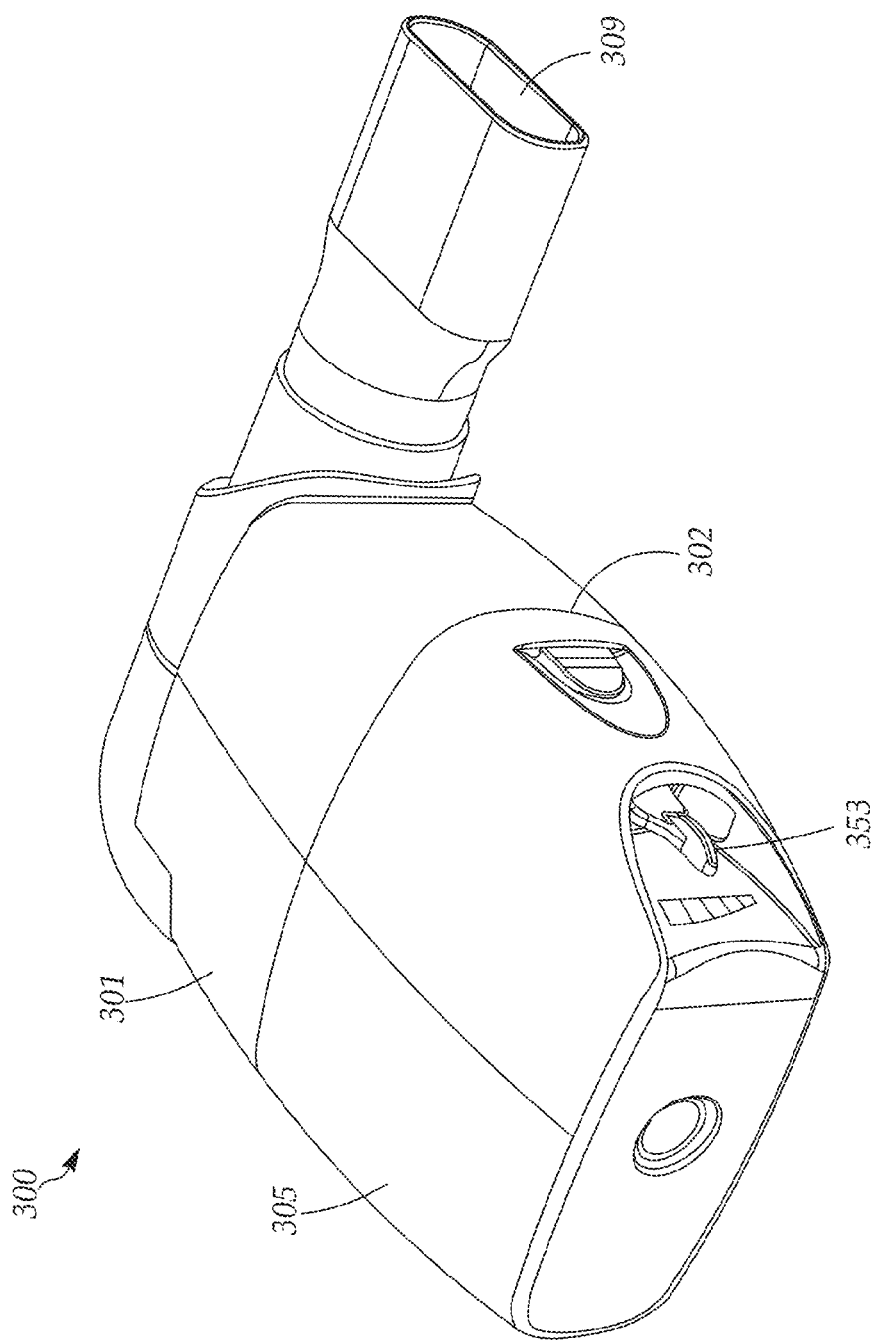
FIG. 37 is a perspective view of the bottom of the OPEP device of FIG. 35.

Turning to FIGS. 35-37, another embodiment of an OPEP device 300 is shown. The OPEP device 300 is similar to that of the OPEP device 200 in that is selectively adjustable. As best seen in FIGS. 35, 37, 40, and 49, the OPEP device 300, like the OPEP device 300, includes an adjustment mechanism 353 adapted to change the relative position of a chamber inlet 304 with respect to a housing 302 and a restrictor member 330, which in turn changes the range of rotation of a vane 332 operatively connected thereto. As previously explained with regards to the OPEP device 200, a user is therefore able to conveniently adjust both the frequency and the amplitude of the OPEP therapy administered by the OPEP device 300 without opening the housing 302 and disassembling the components of the OPEP device 300. The administration of OPEP therapy using the OPEP device 300 is otherwise the same as described above with regards to the OPEP device 100.

The OPEP device 300 comprises a housing 302 having a front section 301, a rear section 305, and an inner casing 303. As with the previously described OPEP devices, the front section 301, the rear section 305, and the inner casing 303 are separable so that the components contained therein can be periodically accessed, cleaned, replaced, or reconfigured, as required to maintain the ideal operating conditions. For example, as shown in FIGS. 35-37, the front section 301 and the rear section 305 of the housing 302 are removably connected via a snap fit engagement.

Figure 38:
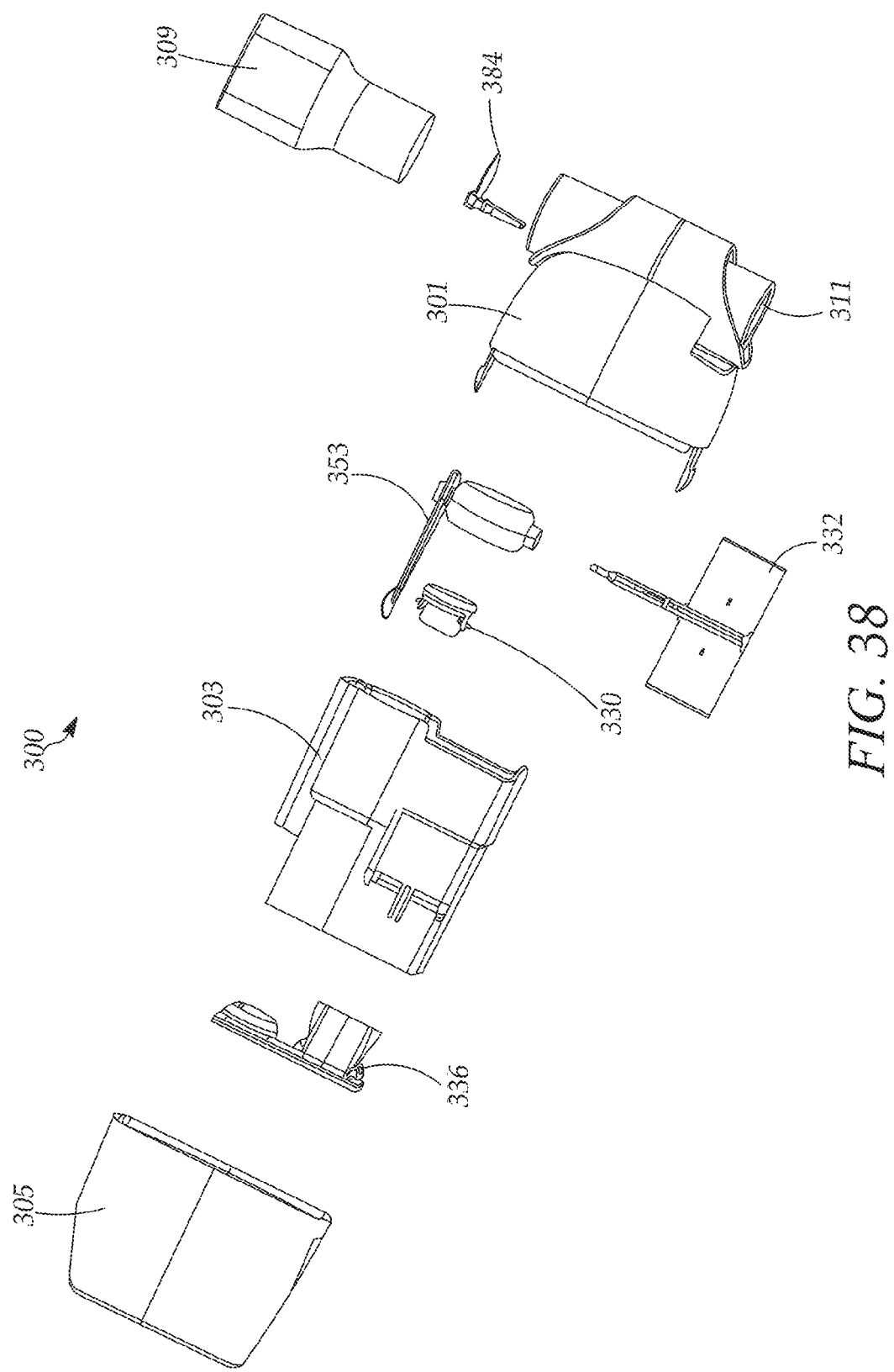
FIG. 38 is an exploded view of the OPEP device of FIG. 35.

The components of the OPEP device 300 are further illustrated in the exploded view of FIG. 38. In general, in addition to the front section 301, the rear section 305, and the inner casing 303, the OPEP device 300 further comprises a mouthpiece 309, an inhalation port 311, a one-way valve 384 disposed therebetween, an adjustment mechanism 353, a restrictor member 330, a vane 332, and a variable nozzle 336.

Figure 39:
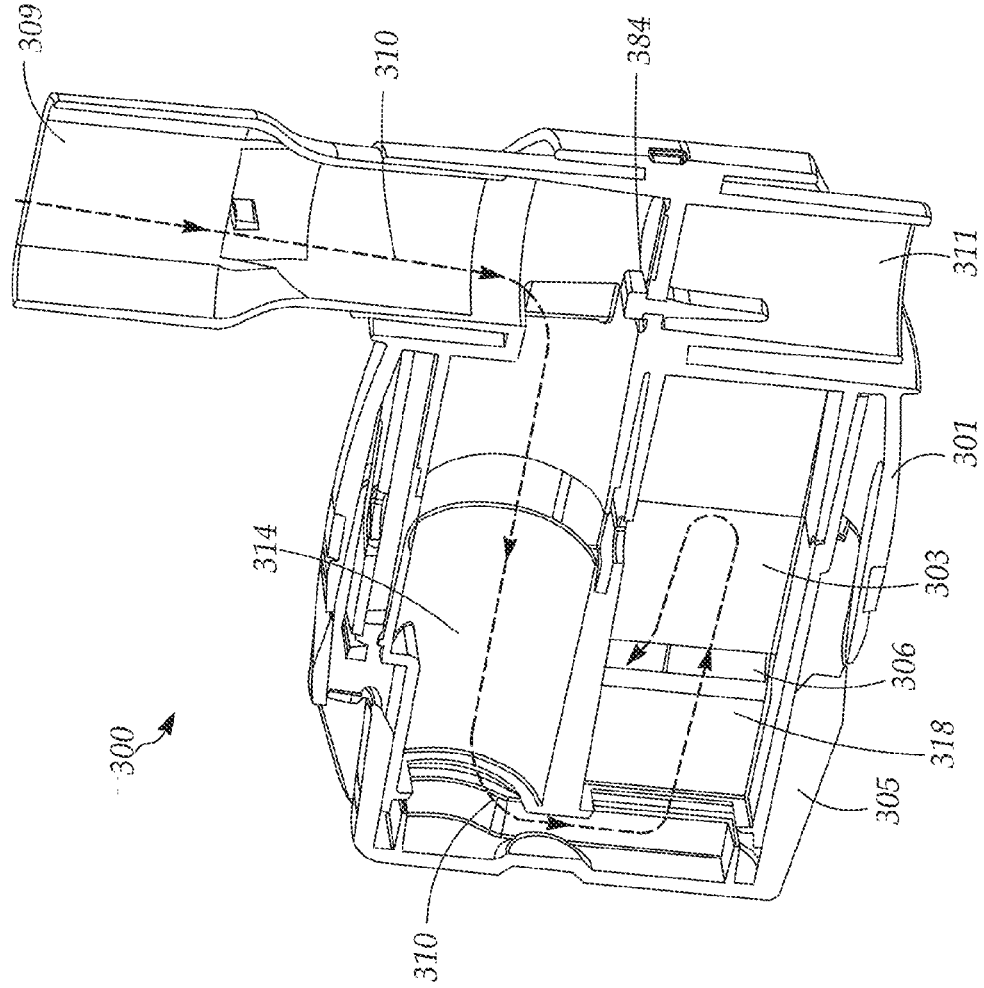
FIG. 39 is a cross-sectional view taken along line I in FIG. 35, shown without the internal components of the OPEP device.
Figure 40:
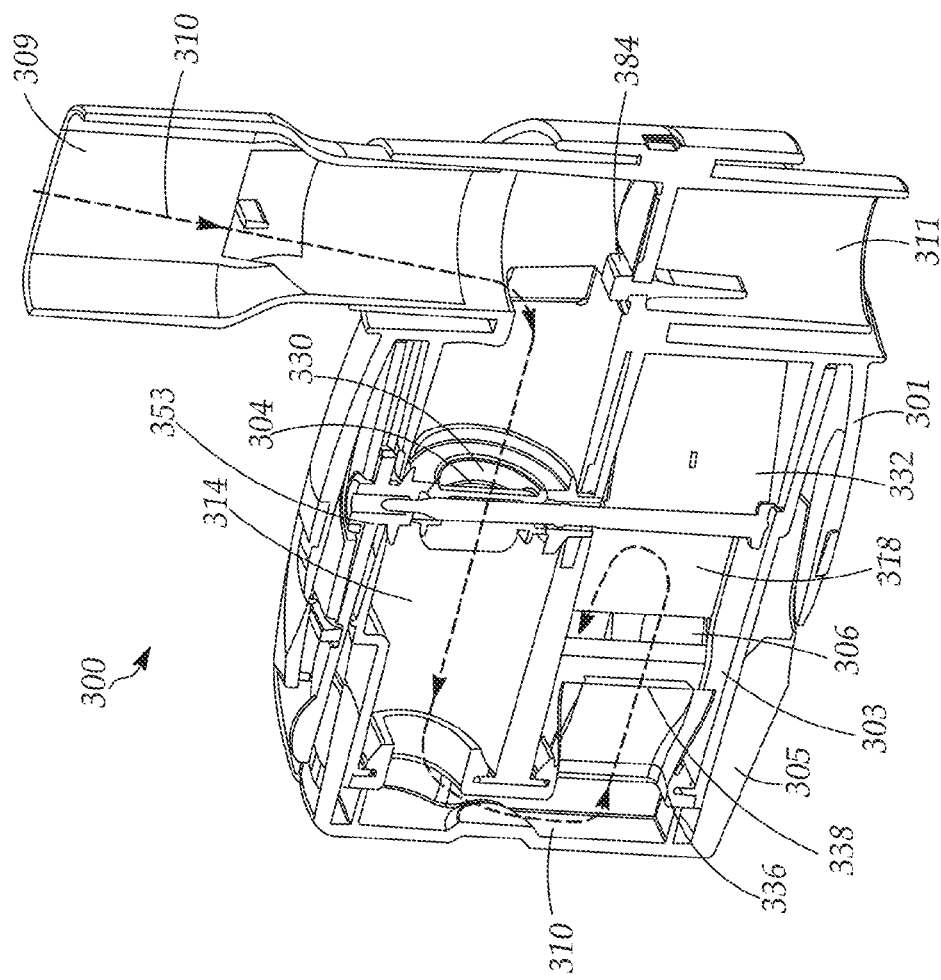
FIG. 40 is a cross-sectional view taken along line I in FIG. 35, shown with the internal components of the OPEP device.
Figure 41:
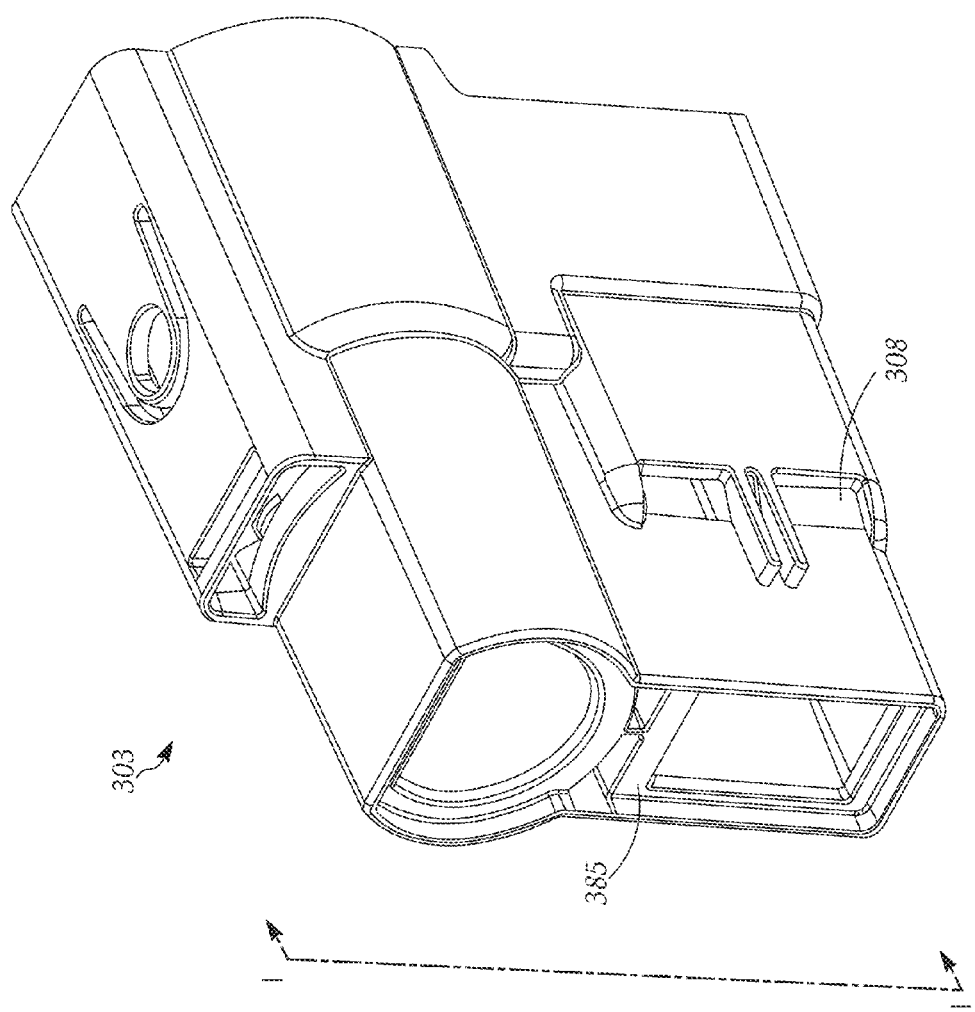
FIG. 41 is a front-perspective view of an inner casing of the OPEP device of FIG. 35.
Figure 42:
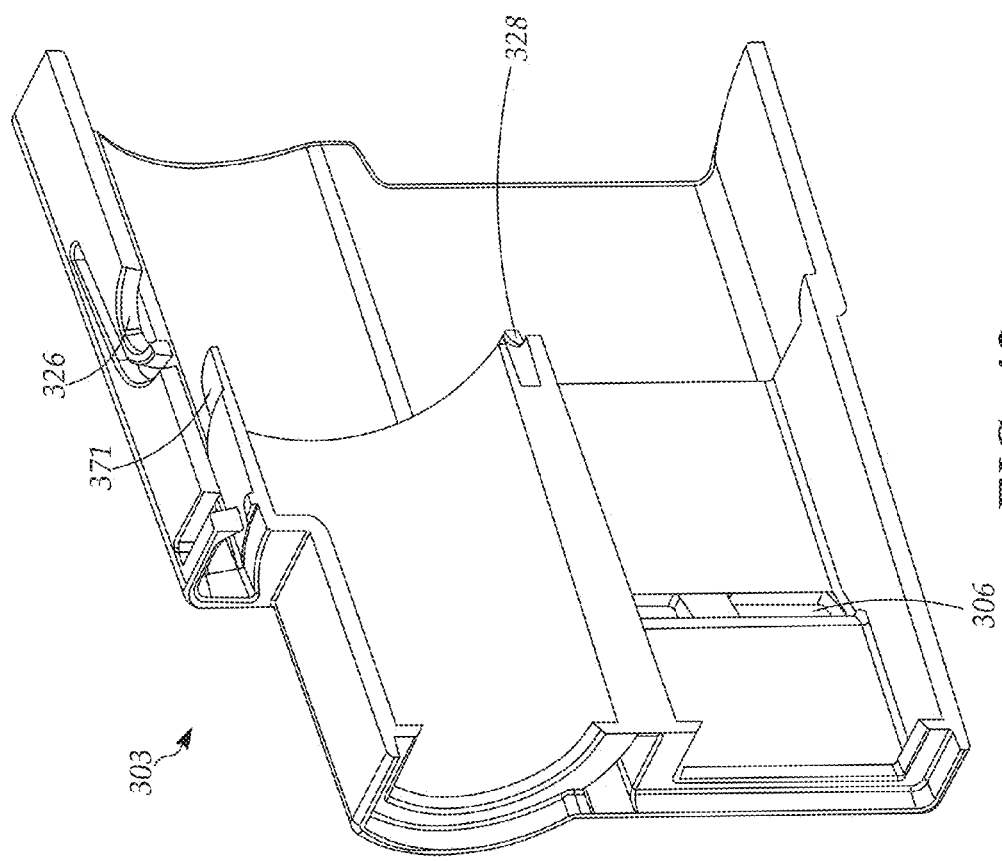
FIG. 42 is a cross-sectional view of the inner casing taken along line I of in FIG. 41.

As seen in FIGS. 39-40, the inner casing 303 is configured to fit within the housing 302 between the front section 301 and the rear section 305, and partially defines a first chamber 314 and a second chamber 318. The inner casing 303 is shown in further detail in the perspective and cross sectional views shown in FIGS. 41-42. A first chamber outlet 306 and a second chamber outlet 308 are formed within the inner casing 303. One end 385 of the inner casing 303 is adapted to receive the variable nozzle 336 and maintain the variable nozzle 336 between the rear section 305 and the inner casing 303. An upper bearing 326 and a lower bearing 328 for supporting the adjustment mechanism 353 is formed, at least in part, within the inner casing 303. Like the flexible cylinder 271 and sealing edge 270 described above with regards to the OPEP device 200, the inner casing 303 also includes a flexible cylinder 371 with a sealing edge 370 for engagement about a frame 356 of the adjustment mechanism 353.

Figure 43:
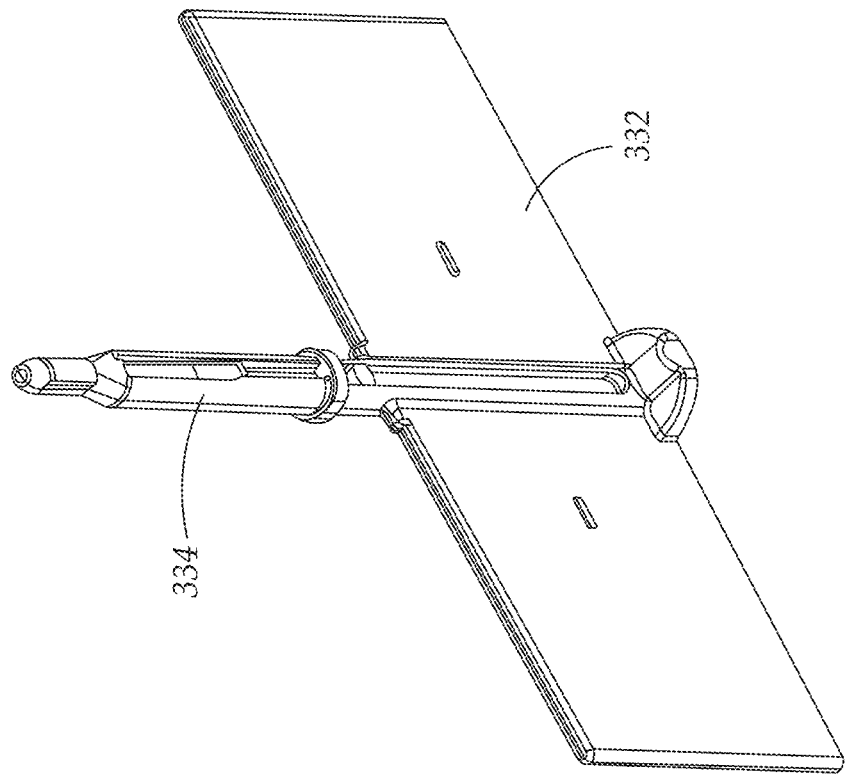
FIG. 43 is a perspective view of a vane of the OPEP device of FIG. 35.

The vane 332 is shown in further detail in the perspective view shown in FIG. 43. A shaft 334 extends from the vane 332 and is keyed to engage a corresponding keyed portion within a bore 365 of the restrictor member 330. In this way, the shaft 334 operatively connects the vane 332 with the restrictor member 330 such that the vane 332 and the restrictor member 330 rotate in unison.

Figure 44:
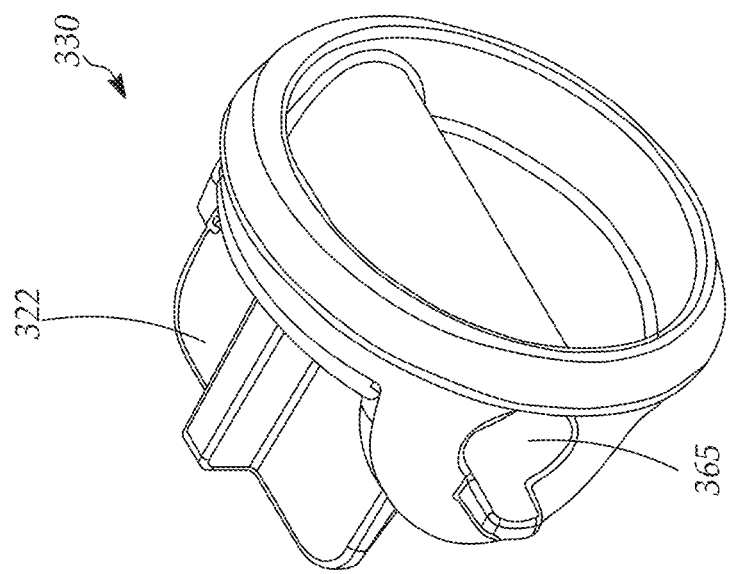
FIG. 44 is a front perspective view of a restrictor member of the OPEP device of FIG. 35.
Figure 46:
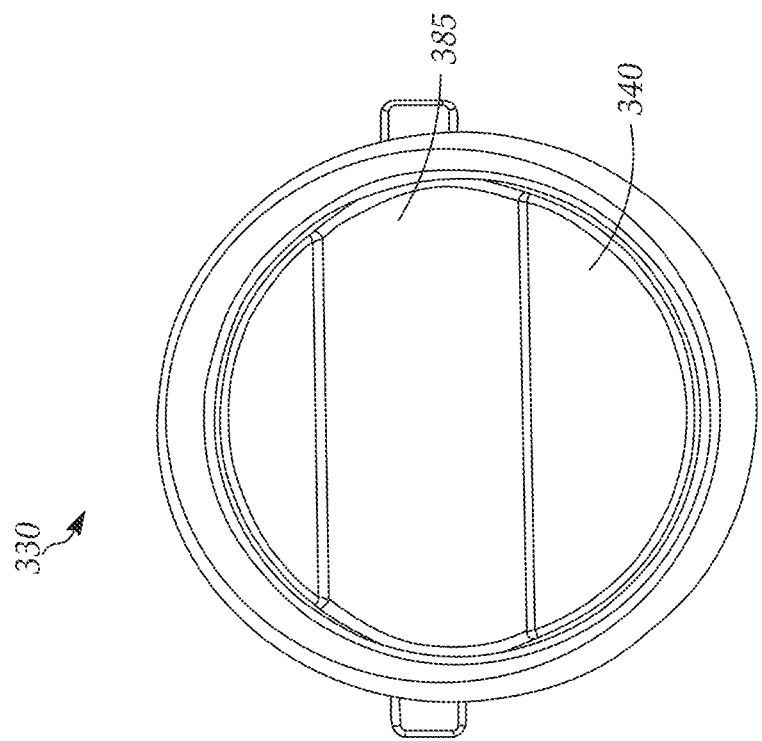
FIG. 46 is a front view of the restrictor member of FIG. 44.
Figure 45:
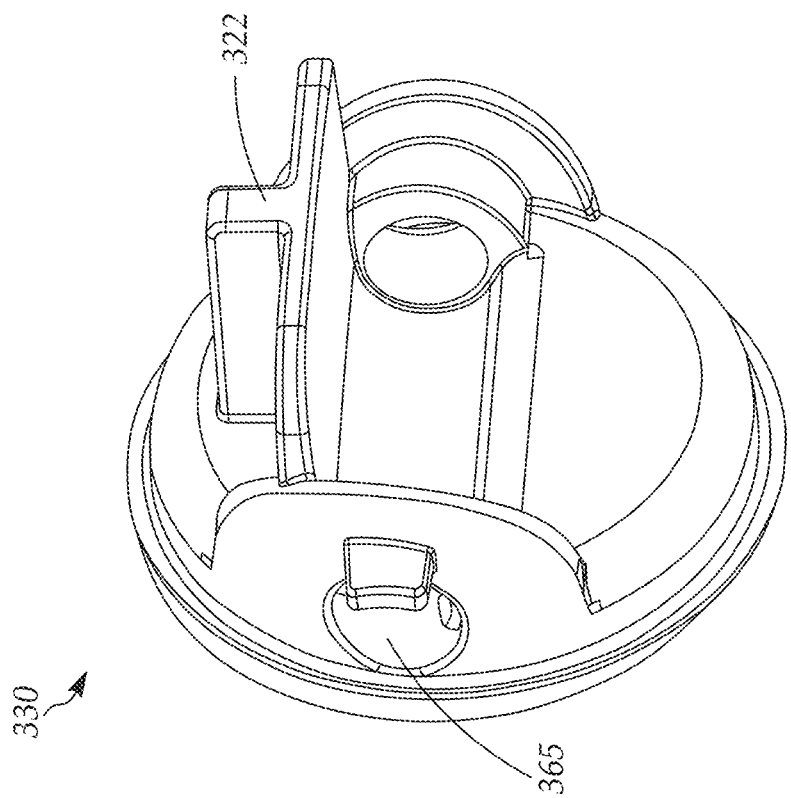
FIG. 45 is a rear perspective view of the restrictor member of the FIG. 44.

The restrictor member 330 is shown in further detail in the perspective views shown in FIGS. 44-45. The restrictor member 330 includes a keyed bore 365 for receiving the shaft 334 extending from the vane 332, and further includes a stop 322 that limits permissible rotation of the restrictor member 330 relative to a seat 324 of the adjustment member 353. As shown in the front view of FIG. 46, like the restrictor member 330, the restrictor member 330 further comprises an offset designed to facilitate movement of the restrictor member 330 between a closed position and an open position. More specifically, a greater surface area of the face 340 of the restrictor member 330 is positioned on one side of the bore 365 for receiving the shaft 334 than on the other side of the bore 365. As described above with regards to the restrictor member 130, this offset produces an opening torque about the shaft 334 during periods of exhalation.

Figure 48:
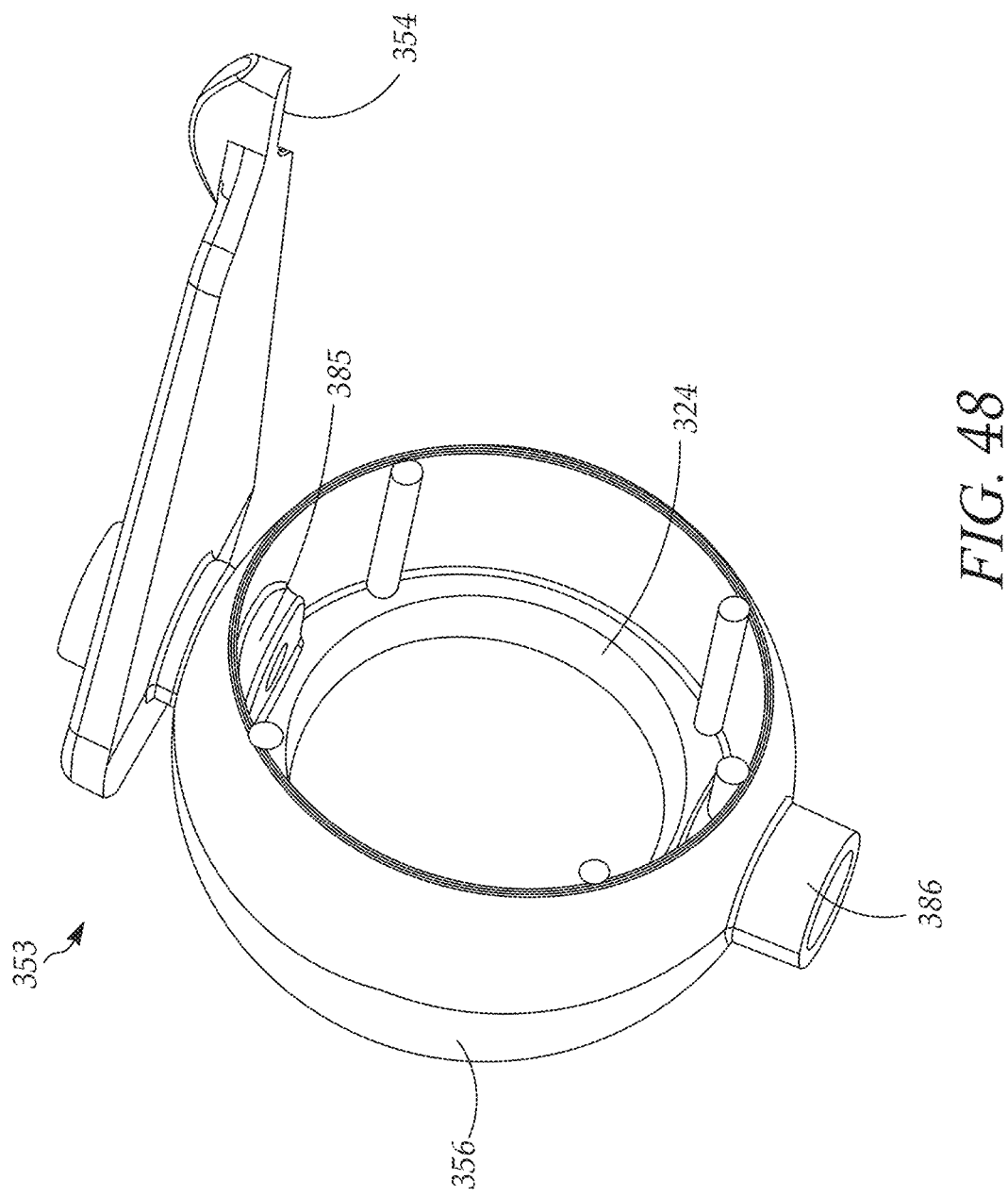
FIG. 48 is a rear perspective view of the adjustment mechanism of FIG. 47.

The adjustment mechanism 353 is shown in further detail in the front and rear perspective views of FIGS. 47 and 48. In general, the adjustment mechanism includes a frame 356 adapted to engage the sealing edge 370 of the flexible cylinder 371 formed on the inner casing 303. A circular opening in the frame 356 forms a seat 324 shaped to accommodate the restrictor member 330. In this embodiment, the seat 324 also defines the chamber inlet 304. The adjustment mechanism 353 further includes an arm 354 configured to extend from the frame 356 to a position beyond the housing 302 in order to permit a user to selectively adjust the orientation of the adjustment mechanism 353, and therefore the chamber inlet 304, when the OPEP device 300 is fully assembled. The adjustment mechanism 353 also includes an upper bearing 385 and a lower bearing 386 for receiving the shaft 334.

Figure 49:
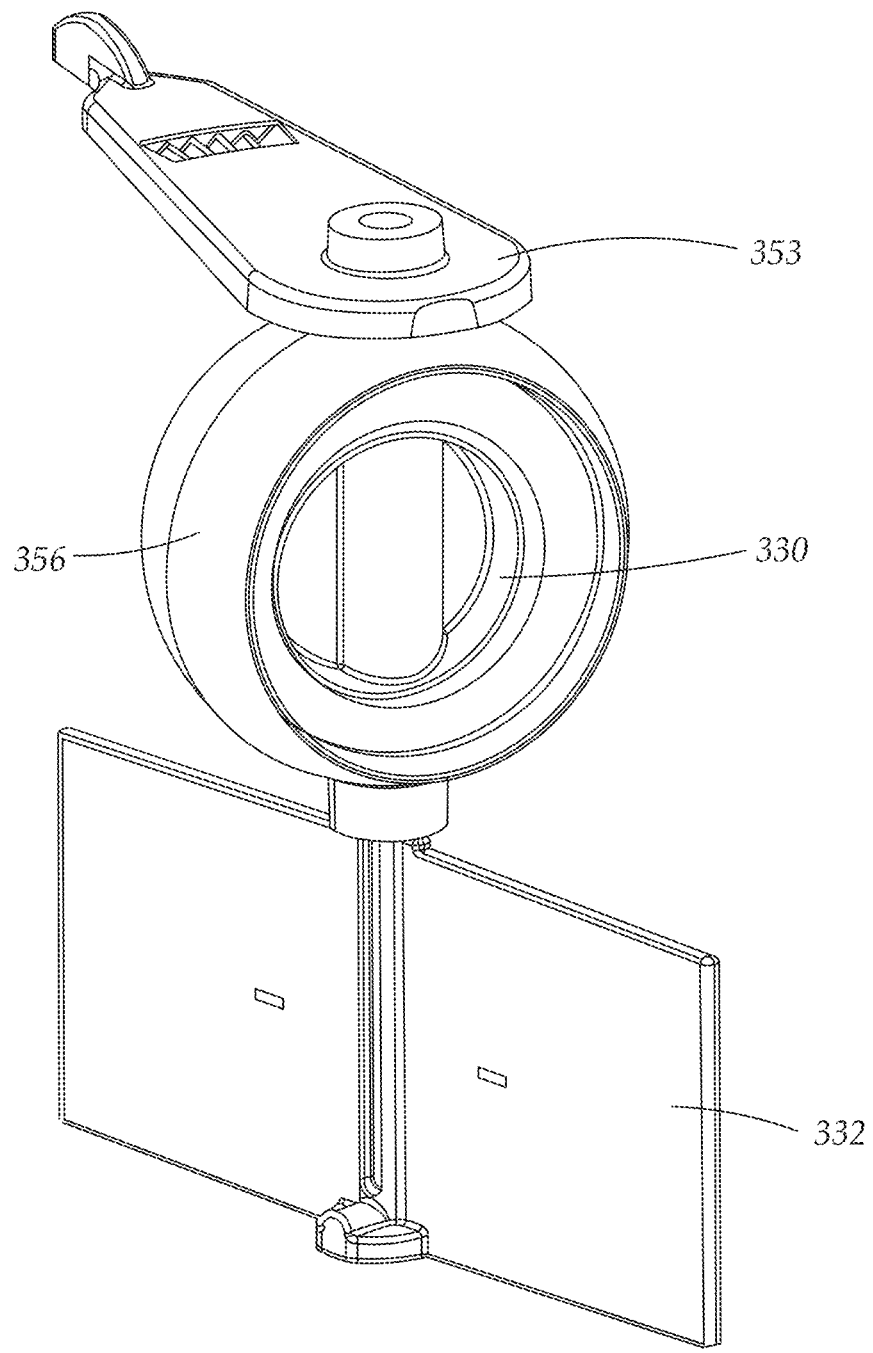
FIG. 49 is a front perspective view of the adjustment mechanism of FIGS. 47-48 assembled with the restrictor member of FIGS. 44-46 and the vane of FIG. 43.

An assembly of the vane 332, the adjustment mechanism 353, and the restrictor member 330 is shown in the perspective view of FIG. 49. As previously explained, the vane 332 and the restrictor member 330 are operatively connected by the shaft 334 such that rotation of the vane 332 results in rotation of the restrictor member 330, and vice versa. In contrast, the adjustment mechanism 353, and therefore the seat 324 defining the chamber inlet 304, is configured to rotate relative to the vane 332 and the restrictor member 330 about the shaft 334. In this way, a user is able to rotate the arm 354 to selectively adjust the orientation of the chamber inlet 304 relative to the restrictor member 330 and the housing 302. For example, a user may increase the frequency and amplitude of the OPEP therapy administered by the OPEP device 800 by rotating the arm 354, and therefore the frame 356, in a clockwise direction. Alternatively, a user may decrease the frequency and amplitude of the OPEP therapy administered by the OPEP device 300 by rotating the adjustment arm 354, and therefore the frame 356, in a counter-clockwise direction. Furthermore, as shown for example in FIGS. 35 and 37, indicia may be provided on the housing 302 to aid the user in the setting of the appropriate configuration of the OPEP device 300.

The variable nozzle 336 is shown in further detail in the front and rear perspective views of FIGS. 50 and 51. The variable nozzle 336 in the OPEP device 300 is similar to the variable nozzle 236 described above with regards to the OPEP device 200, except that the variable nozzle 336 also includes a base plate 387 configured to fit within one end 385 (see FIGS. 41-42) of the inner casing 303 and maintain the variable nozzle 336 between the rear section 305 and the inner casing 303. Like the variable nozzle 236, the variable nozzle 336 and base plate 387 may be made of silicone.

The one-way valve 384 is shown in further detail in the front perspective view of FIG. 52. In general, the one-way valve 384 comprises a post 388 adapted for mounting in the front section 301 of the housing 302, and a flap 389 adapted to bend or pivot relative to the post 388 in response to a force or a pressure on the flap 389. Those skilled in the art will appreciate that other one-way valves may be used in this and other embodiments described herein without departing from the teachings of the present disclosure. As seen in FIGS. 39-40, the one-way valve 384 may be positioned in the housing 302 between the mouthpiece 309 and the inhalation port 311.

As discussed above in relation to the OPEP device 100, the OPEP device 300 may be adapted for use with other or additional interfaces, such as an aerosol delivery device. In this regard, the OPEP device 300 is equipped with an inhalation port 311 (best seen in FIGS. 35-36 and 38-40) in fluid communication with the mouthpiece 309. As noted above, the inhalation port may include a separate one-way valve 384 (best seen in FIGS. 39-40 and 52) configured to permit a user of the OPEP device 300 both to inhale the surrounding air through the one-way valve 384 and to exhale through the chamber inlet 304, without withdrawing the mouthpiece 309 of the OPEP device 300 between periods of inhalation and exhalation. In addition, the aforementioned commercially available aerosol delivery devices may be connected to the inhalation port 311 for the simultaneous administration of aerosol therapy (upon inhalation) and OPEP therapy (upon exhalation).

The OPEP device 300 and the components described above are further illustrated in the cross-sectional views shown in FIGS. 39-40. For purposes of illustration, the cross-sectional view of FIG. 39 is shown without all the internal components of the OPEP device 300.

The front section 301, the rear section 305, and the inner casing 303 are assembled to form a first chamber 314 and a second chamber 318. As with the OPEP device 100, an exhalation flow path 310, identified by a dashed line, is defined between the mouthpiece 309 and at least one of the first chamber outlet 306 (best seen in FIGS. 39-40 and 42) and the second chamber outlet 308 (best seen in FIG. 41), both of which are formed within the inner casing 303. As a result of the inhalation port 311 and the one-way valve 348, the exhalation flow path 310 begins at the mouthpiece 309 and is directed toward the chamber inlet 304, which in operation may or may not be blocked by the restrictor member 330. After passing through the chamber inlet 304, the exhalation flow path 310 enters the first chamber 314 and makes a 180° turn toward the variable nozzle 336. After passing through an orifice 338 of the variable nozzle 336, the exhalation flow path 310 enters the second chamber 318. In the second chamber 318, the exhalation flow path 310 may exit the second chamber 318, and ultimately the housing 302, through at least one of the first chamber outlet 306 or the second chamber outlet 308. Those skilled in the art will appreciate that the exhalation flow path 310 identified by the dashed line is exemplary, and that air exhaled into the OPEP device 300 may flow in any number of directions or paths as it traverses from the mouthpiece 309 or chamber inlet 304 to the first chamber outlet 306 or the second chamber outlet 308. As previously noted, the administration of OPEP therapy using the OPEP device 300 is otherwise the same as described above with regards to the OPEP device 100.

Solely by way of example, the follow operating conditions, or performance characteristics, may be achieved by an OPEP device according to the OPEP device 300, with the adjustment dial 354 set for increased frequency and amplitude:

| Flow Rate (lpm) | 10 | 30 |
|---|---|---|
| Frequency (Hz) | 7 | 20 |
| Upper Pressure (cm H2O) | 13 | 30 |
| Lower Pressure (cm H2O) | 1.5 | 9 |
| Amplitude (cm H2O) | 11.5 | 21 |

The frequency and amplitude may decrease, for example, by approximately 20% with the adjustment dial 354 set for decreased frequency and amplitude. Other frequency and amplitude targets may be achieved by varying the particular configuration or sizing of elements, for example, increasing the length of the vane 332 results in a slower frequency, whereas, decreasing the size of the orifice 338 results in a higher frequency. The above example is merely one possible set of operating conditions for an OPEP device according to the embodiment described above.

Fourth Embodiment

Turning to FIGS. 53-56, another embodiment of a respiratory treatment device 400 is shown. Unlike the previously described OPEP devices, the respiratory treatment device 400 is configured to administer oscillating pressure therapy upon both exhalation and inhalation. Those skilled in the art will appreciate that the concepts described below with regards to the respiratory treatment device 400 may be applied to any of the previously described OPEP devices, such that oscillating pressure therapy may be administered upon both exhalation and inhalation. Likewise, the respiratory treatment device 400 may incorporate any of the concepts above regarding the previously described OPEP devices, including for example, a variable nozzle, an inhalation port adapted for use with an aerosol delivery device for the administration of aerosol therapy, an adjustment mechanism, etc.

Figure 53:
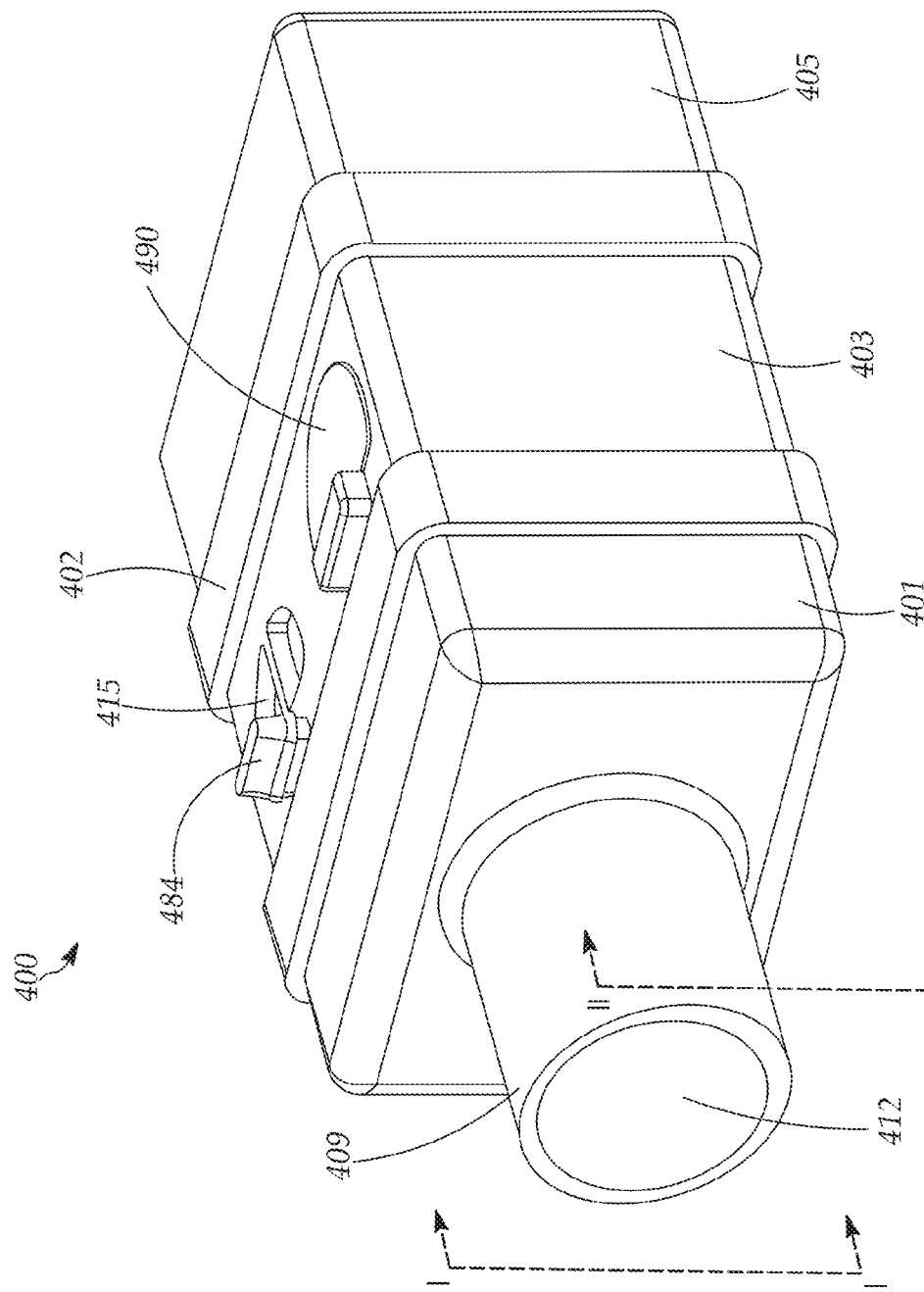
FIG. 53 is a perspective view of another embodiment of a respiratory treatment device.
Figure 54:
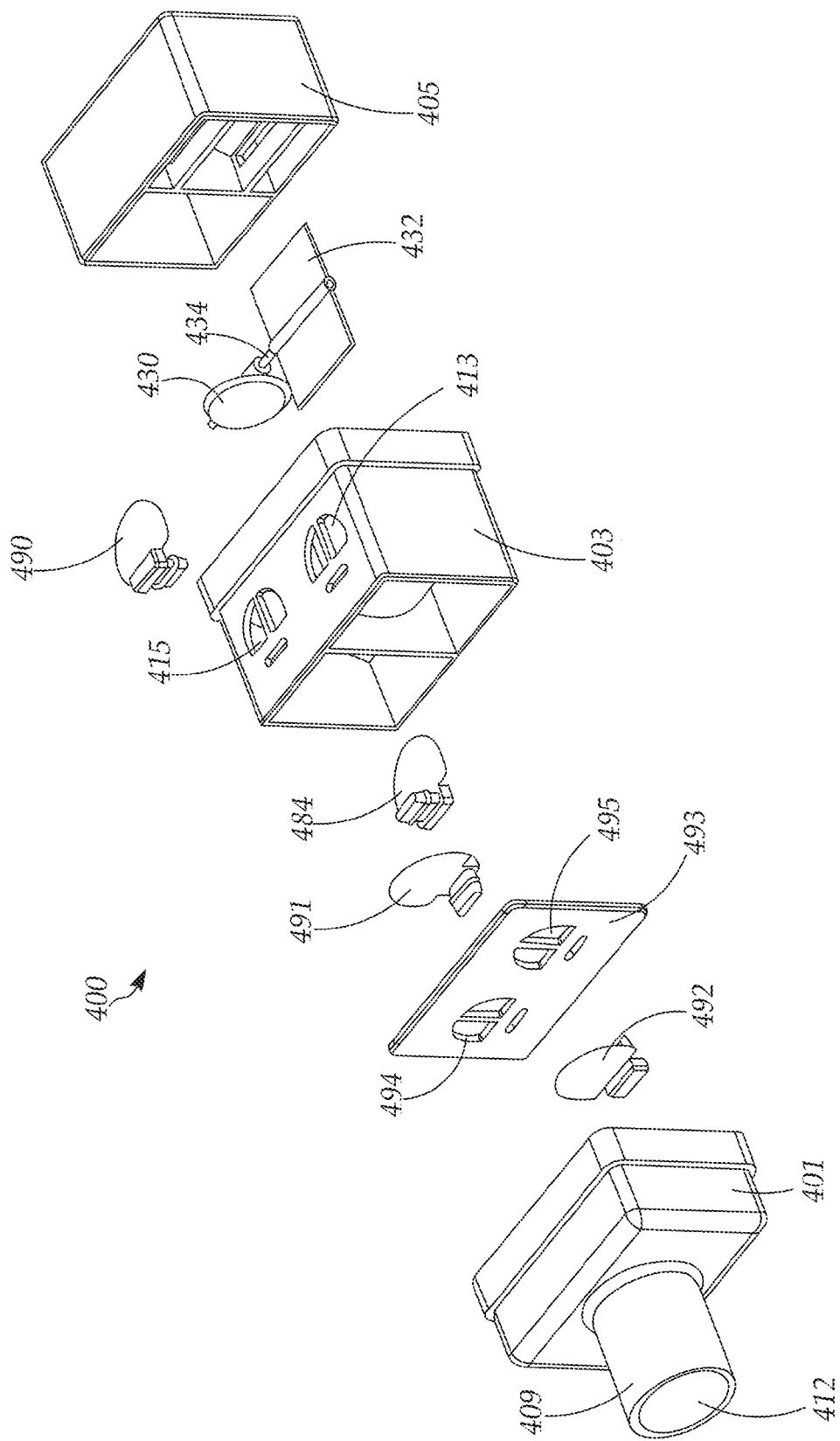
FIG. 54 is an exploded view of the respiratory treatment device of FIG. 53.

As shown in FIGS. 53 and 54, the respiratory treatment device 400 includes a housing 402 having a front section 401, a middle section 403, and a rear section 405. As with the OPEP devices described above, the housing 402 is openable so that the contents of the housing 402 may be accessed for cleaning and/or selective replacement or adjustment of the components contained therein to maintain ideal operating conditions. The housing 402 further includes a first opening 412, a second opening 413, and a third opening 415.

Although the first opening 412 is shown in FIGS. 53 and 54 in association with a mouthpiece 409, the first opening 412 may alternatively be associated with other user interfaces, for example, a gas mask or a breathing tube. The second opening 413 includes a one-way exhalation valve 490 configured to permit air exhaled into the housing 402 to exit the housing 402 upon exhalation at the first opening 412. The third opening 415 includes a one-way inhalation valve 484 configured to permit air outside the housing 402 to enter the housing 402 upon inhalation at the first opening 412. As shown in greater detail in FIG. 54, the respiratory treatment device 400 further includes a manifold plate 493 having an exhalation passage 494 and an inhalation passage 495. A one-way valve 491 is adapted to mount to within the manifold plate 493 adjacent to the exhalation passage 494 such that the one-way valve 491 opens in response to air exhaled into the first opening 412, and closes in response to air inhaled through the first opening 412. A separate one-way valve 492 is adapted to mount within the manifold pate 493 adjacent to the inhalation passage 495 such that the one-way valve 492 closes in response to air exhaled into the first opening 412, and opens in response to air inhaled through the first opening 412. The respiratory treatment device 400 also includes a restrictor member 430 and a vane 432 operatively connected by a shaft 434, the assembly of which may operate in the same manner as described above with regards to the disclosed OPEP devices.

Figure 55:
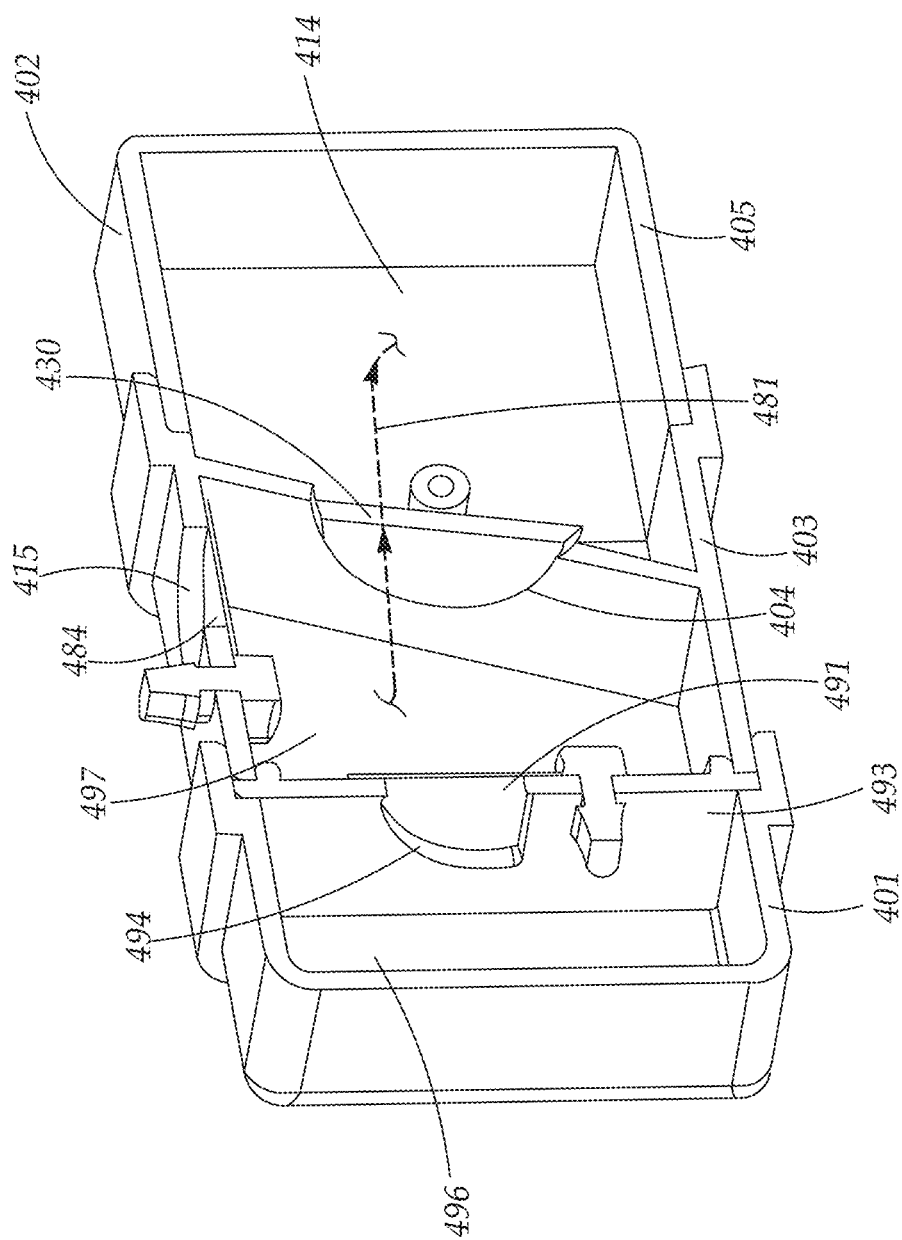
FIG. 55 is a cross-sectional perspective view taken along line I in FIG. 53 of the respiratory treatment device shown with the internal components of the device.
Figure 56:
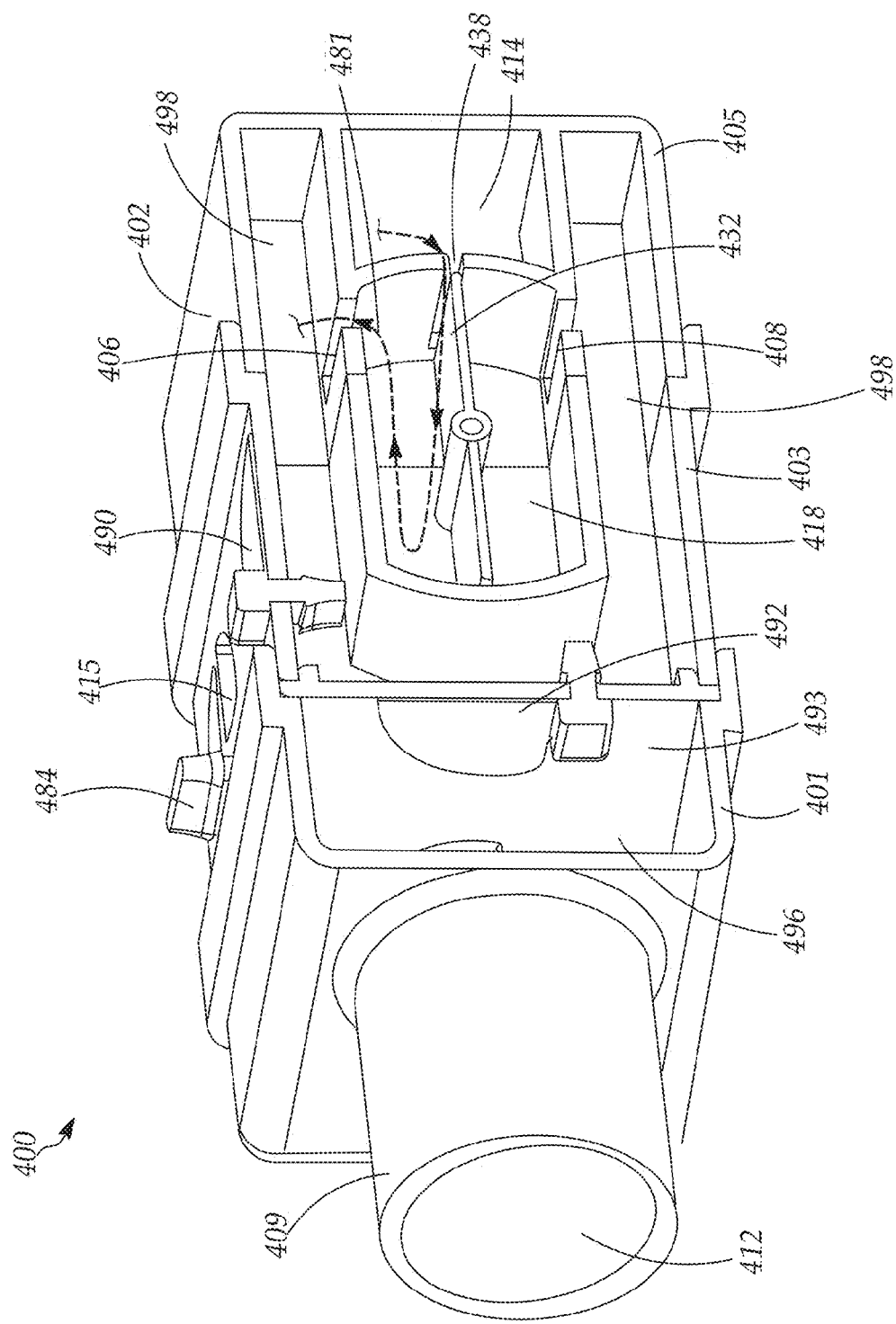
FIG. 56 is a cross-sectional perspective view taken along line II in FIG. 53 of the respiratory treatment device shown with the internal components of the device.

Referring now to FIGS. 55 and 56, cross-sectional perspective views are shown taken along lines I and II, respectively, in FIG. 53. The respiratory treatment device 400 administers oscillating pressure therapy upon both inhalation and exhalation in a manner similar to that shown and described above with regards to the OPEP devices. As described in further detail below, the OPEP device 400 includes a plurality of chambers (i.e., more than one). Air transmitted through the first opening 412 of the housing 402, whether inhaled or exhaled, traverses a flow path that passes, at least in part, past a restrictor member 430 housed in a first chamber 414, and through a second chamber 418 which houses a vane 432 operatively connected to the restrictor member 430. In this regard, at least a portion of the flow path for both air exhaled into or inhaled from the first opening 412 is overlapping, and occurs in the same direction.

For example, an exemplary flow path 481 is identified in FIGS. 55 and 56 by a dashed line. Similar to the previously described OPEP devices, the restrictor member 430 is positioned in the first chamber 414 and is movable relative to a chamber inlet 404 between a closed position, where the flow of air through the chamber inlet 404 is restricted, and an open position, where the flow of air through the chamber 404 inlet is less restricted. After passing through the chamber inlet 404 and entering the first chamber 414, the exemplary flow path 481 makes a 180-degree turn, or reverses longitudinal directions (i.e., the flow path 481 is folded upon itself), whereupon the exemplary flow path 481 passes through an orifice 438 and enters the second chamber 418. As with the previously described OPEP devices, the vane 432 is positioned in the second chamber 418, and is configured to reciprocate between a first position and a second position in response to an increased pressure adjacent the vane, which in turn causes the operatively connected restrictor member 430 to repeatedly move between the closed position and the open position. Depending on the position of the vane 432, air flowing along the exemplary flow path 481 is directed to one of either a first chamber outlet 406 or a second chamber outlet 408. Consequently, as inhaled or exhaled air traverses the exemplary flow path 481, pressure at the chamber inlet 404 oscillates.

The oscillating pressure at the chamber inlet 404 is effectively transmitted back to a user of the respiratory treatment device 400, i.e., at the first opening 412, via a series of chambers. As seen in FIGS. 55 and 56, the respiratory treatment device includes a first additional chamber 496, a second additional chamber 497, and a third additional chamber 498, which are described in further detail below.

The mouthpiece 409 and the first additional chamber 496 are in communication via the first opening 412 in the housing 402. The first additional chamber 496 and the second additional chamber 497 are separated by the manifold plate 493, and are in communication via the exhalation passage 494. The one-way valve 491 mounted adjacent to the exhalation passage 494 is configured to open in response to air exhaled into the first opening 412, and close in response to air inhaled through the first opening 412.

The first additional chamber 496 and the third additional chamber 498 are also separated by the manifold plate 493, and are in communication via the inhalation passage 495. The one-way valve 492 mounted adjacent to the inhalation passage 495 is configured to close in response to air exhaled into the first opening 412, and open in response to air inhaled through the first opening 412.

Air surrounding the respiratory treatment device 400 and the second additional chamber 497 are in communication via the third opening 415 in the housing 402. The one-way valve 484 is configured to close in response to air exhaled in to the first opening 412, and open in response to air inhaled through the first opening 412.

Air surrounding the respiratory treatment device 400 and the third additional chamber 498 are in communication via the second opening 413 in the housing 402. The one way-valve 490 mounted adjacent the second opening 413 is configured to open in response to air exhaled into the first opening 412, and close in response to air inhaled through the first opening 412. The third additional chamber 498 is also in communication with the second chamber 418 via the first chamber outlet 406 and the second chamber outlet 408.

Figure 57:
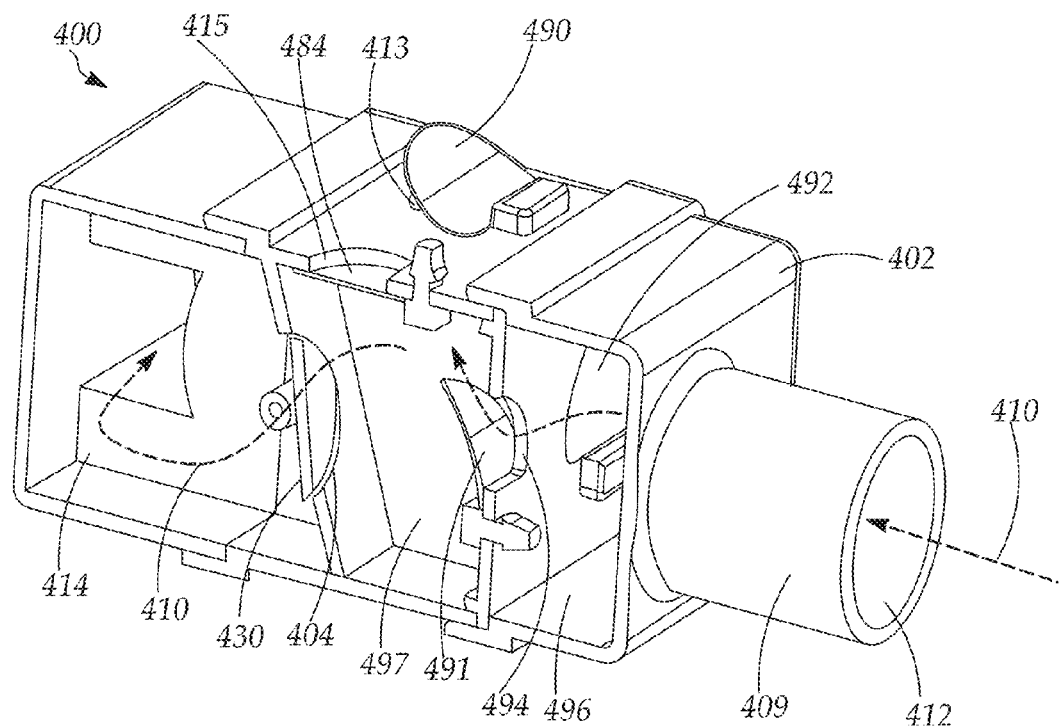
FIG. 57 is a different cross-sectional perspective view taken along line I in FIG. 53 of the respiratory treatment device, showing a portion of an exemplary exhalation flow path.
Figure 58:
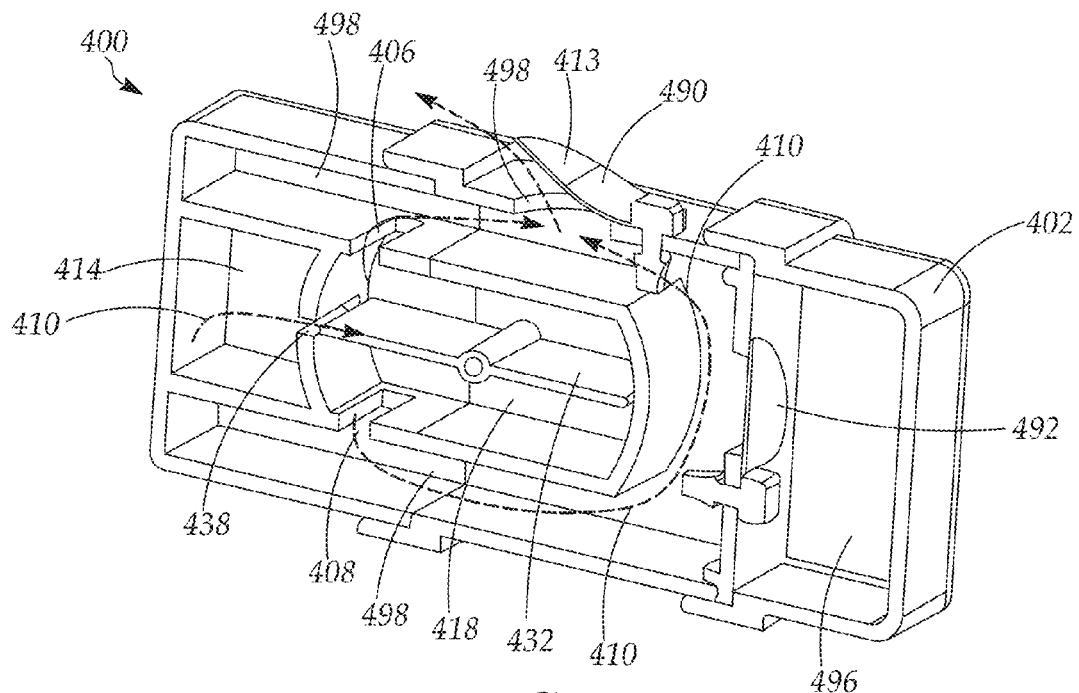
FIG. 58 is a different cross-sectional perspective view taken along line II in FIG. 53, showing a portion of an exemplary exhalation flow path.

Referring now to FIGS. 57-58, cross-sectional perspective views taken along lines I and II, respectively, of FIG. 53, illustrate an exemplary exhalation flow path 410 formed between the first opening 412, or the mouthpiece 409, and the second opening 413. In general, upon exhalation by a user into the first opening 412 of the housing 402, pressure builds in the first additional chamber 496, causing the one-way valve 491 to open, and the one-way valve 492 to close. Exhaled air then enters the second additional chamber 497 through the exhalation passage 494 and pressure builds in the second additional chamber 497, causing the one-way valve 484 to close and the restrictor member 430 to open. The exhaled air then enters the first chamber 414 through the chamber inlet 404, reverses longitudinal directions, and accelerates through the orifice 438 separating the first chamber 414 and the second chamber 418. Depending on the orientation of the vane 432, the exhaled air then exits the second chamber 418 through one of either the first chamber outlet 406 or the second chamber outlet 408, whereupon it enters the third additional chamber 498. As pressure builds in the third additional chamber 498, the one-way valve 490 opens, permitting exhaled air to exit the housing 402 through the second opening 413. Once the flow of exhaled air along the exhalation flow path 410 is established, the vane 432 reciprocates between a first position and a second position, which in turn causes the restrictor member 430 to move between the closed position and the open position, as described above with regards to the OPEP devices. In this way, the respiratory treatment device 400 provides oscillating therapy upon exhalation.

Figure 59:
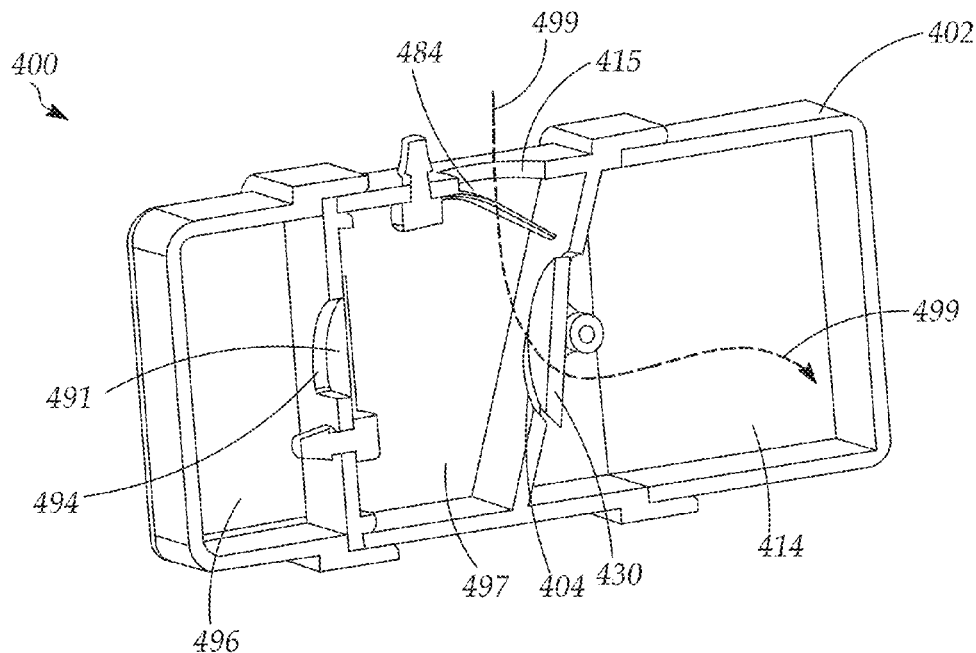
FIG. 59 is another cross-sectional perspective view taken along line I in FIG. 53, showing a portion of an exemplary inhalation flow path.
Figure 60:
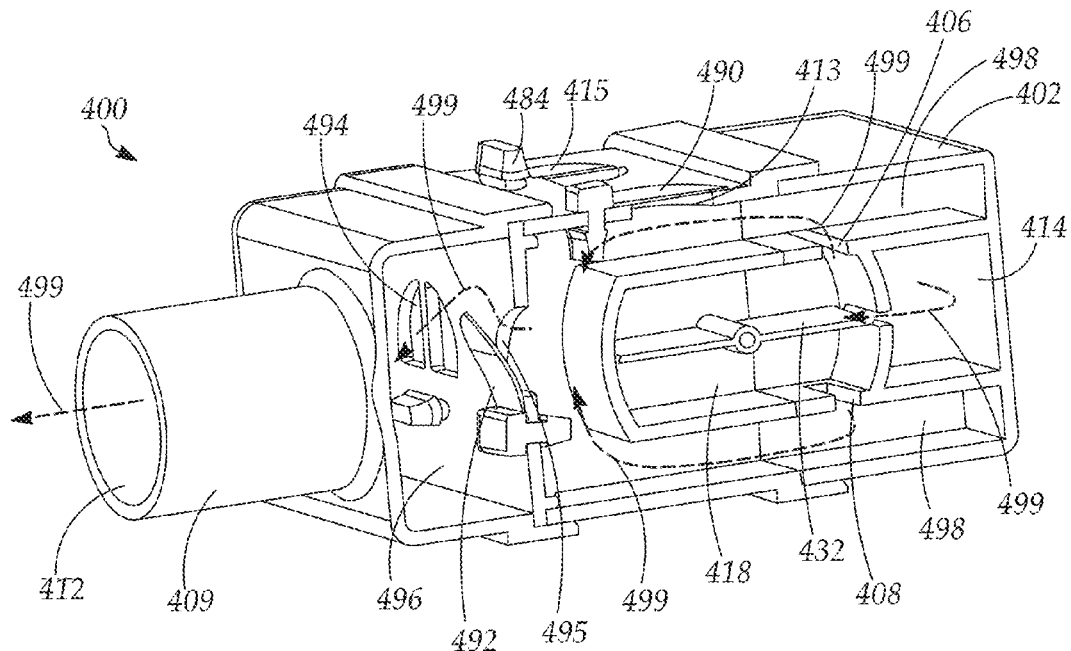
FIG. 60 is another cross-sectional perspective view taken along line II in FIG. 53, showing a portion of an exemplary inhalation flow path.

Referring now to FIGS. 59-60, different cross-sectional perspective views taken along lines I and II, respectively, of FIG. 53, illustrate an exemplary inhalation flow path 499 formed between the third opening 415 and the first opening 412, or the mouthpiece 409. In general, upon inhalation by a user through the first opening 412, pressure drops in the first additional chamber 496, causing the one-way valve 491 to close, and the one-way valve 492 to open. As air is inhaled from the third additional chamber 498 into the first additional chamber 496 through the inhalation passage 495, pressure in the third additional chamber 498 begins to drop, causing the one-way valve 490 to close. As pressure continues to drop in the third additional chamber 498, air is drawn from the second chamber 418 through the first chamber outlet 406 and the second chamber outlet 408. As air is drawn from the second chamber 918, air is also drawn from the first chamber 414 through the orifice 438 connecting the second chamber 418 and the first chamber 414. As air is drawn from the first chamber 414, air is also drawn from the second additional chamber 497 through the chamber inlet 404, causing the pressure in the second additional chamber 497 to drop and the one-way valve 484 to open, thereby permitting air to enter the housing 402 through third opening 415. Due to the pressure differential between the first additional chamber 496 and the second additional chamber 497, the one-way valve 491 remains closed. Once the flow of inhaled air along the inhalation flow path 499 is established, the vane 432 reciprocates between a first position and a second position, which in turn causes the restrictor member 430 to move between the closed position and the open position, as described above with regards to the OPEP devices. In this way, the respiratory treatment device 400 provides oscillating therapy upon inhalation.

Fifth Embodiment

Turning to FIGS. 61-66, another embodiment of a respiratory treatment device 500 is shown. Like the respiratory treatment device 400, the respiratory treatment device 500 is configured to provide OPEP therapy upon both exhalation and inhalation. Except as described below, the components and configuration of the OPEP device 400 are the same as or similar to that of the respiratory treatment device 400.

The respiratory treatment device 500 differs from the respiratory treatment device 400 in that it is configured to selectively provide OPEP therapy upon exhalation only, inhalation only, or both exhalation and inhalation. As explained in greater detail below, a user may select administration of OPEP therapy upon exhalation only, inhalation only, or both exhalation and inhalation, by operation of a switch 504. Those skilled in the art will appreciate that the concepts described below with regards to the respiratory treatment device 500 may be applied to any of the previously described embodiments.

Figure 61:
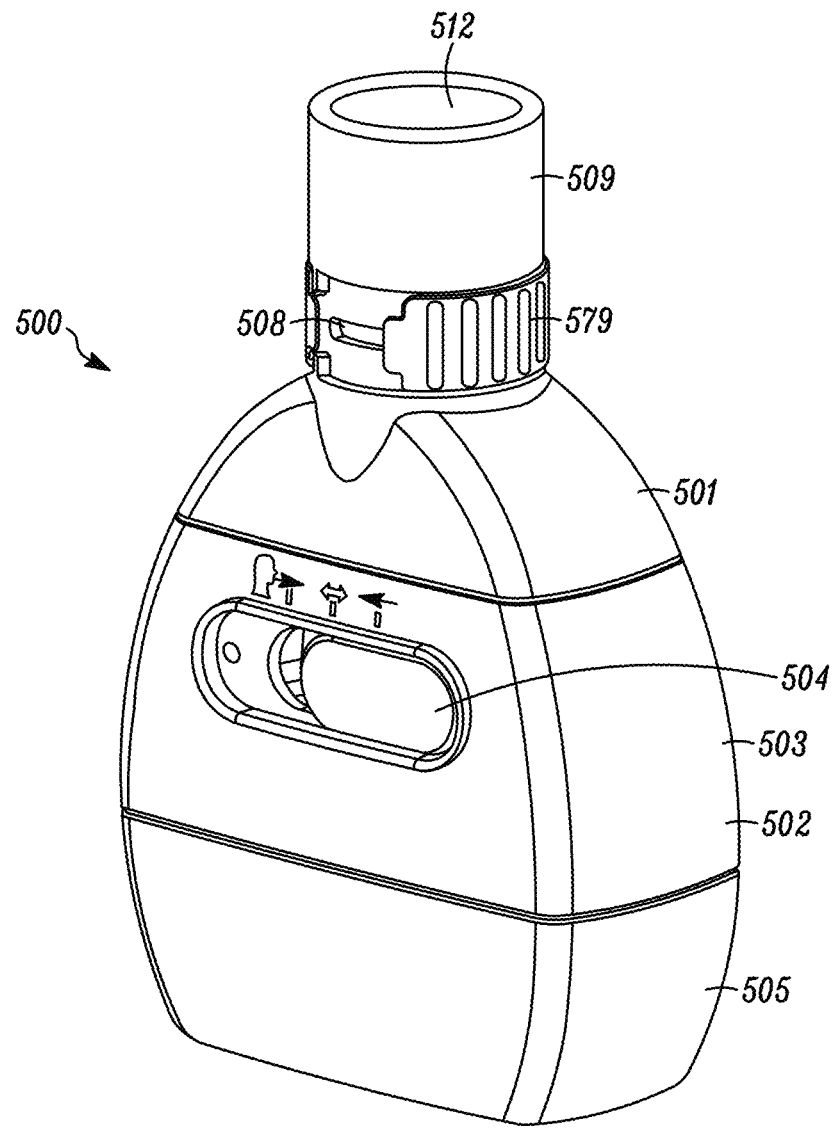
FIG. 61 is a front perspective view of another embodiment of a respiratory treatment device.
Figure 62:
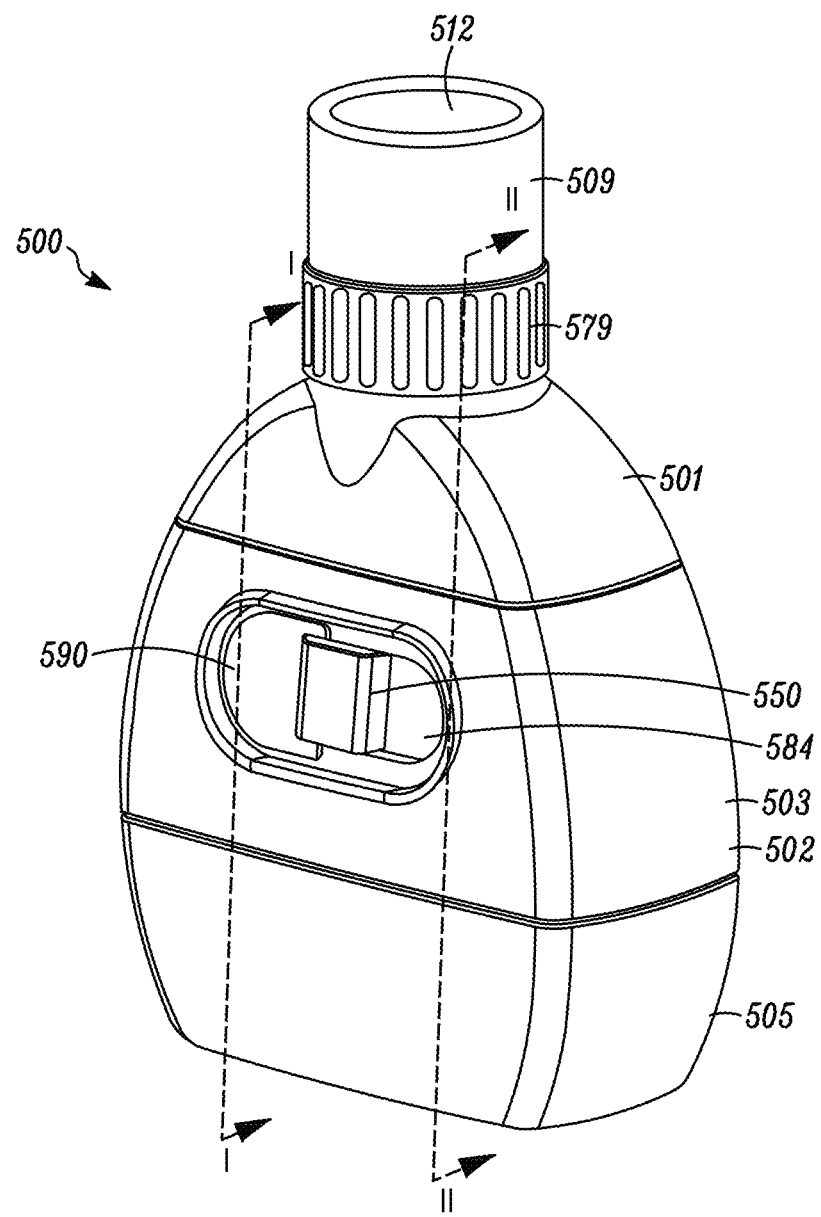
FIG. 62 is a rear perspective view of the respiratory treatment device of FIG. 61.
Figure 63A:
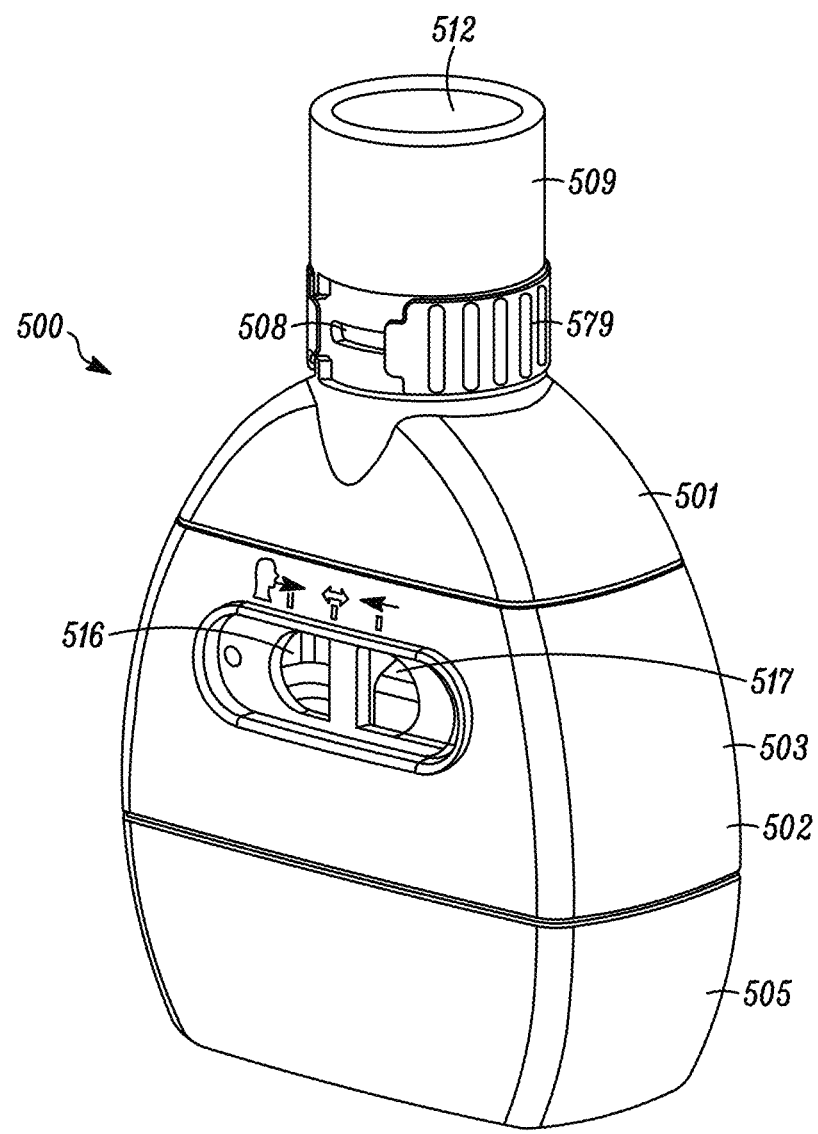
FIG. 63A-B are front and rear perspective views of the respiratory treatment device of FIG. 61, showing openings formed in the device's housing.
Figure 63B:
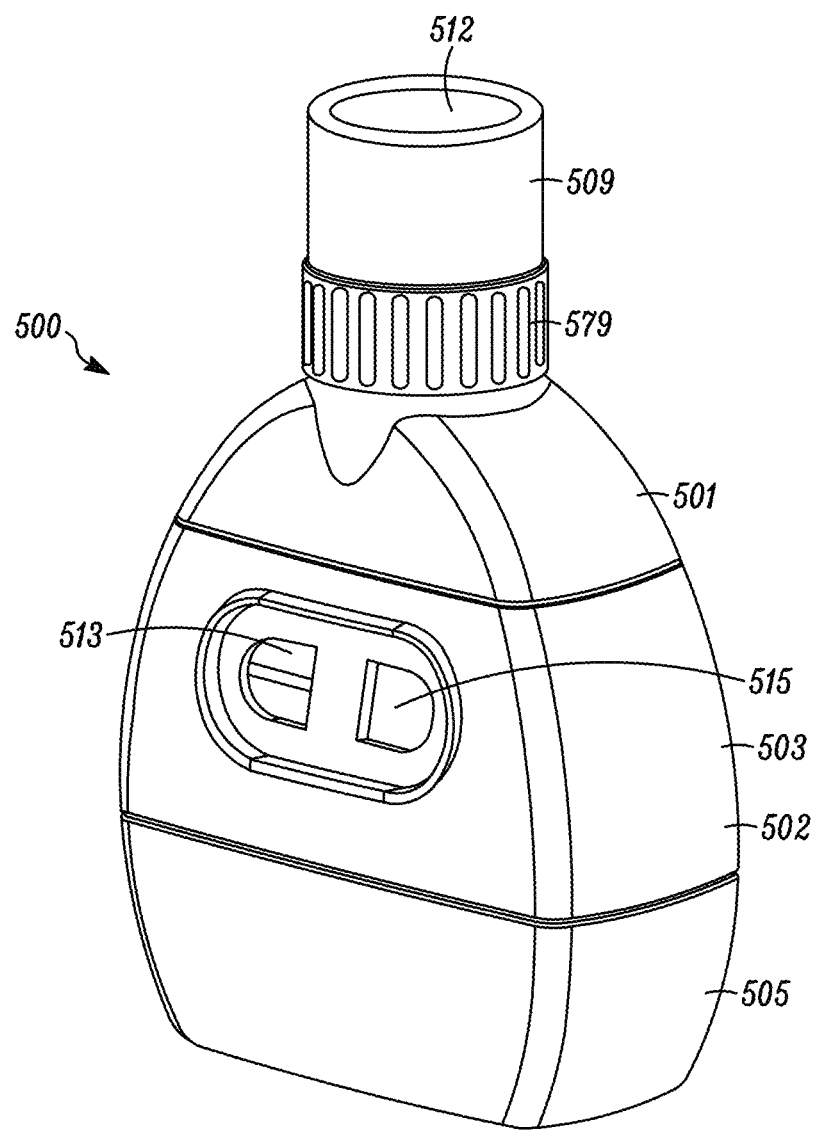
Figure 65:
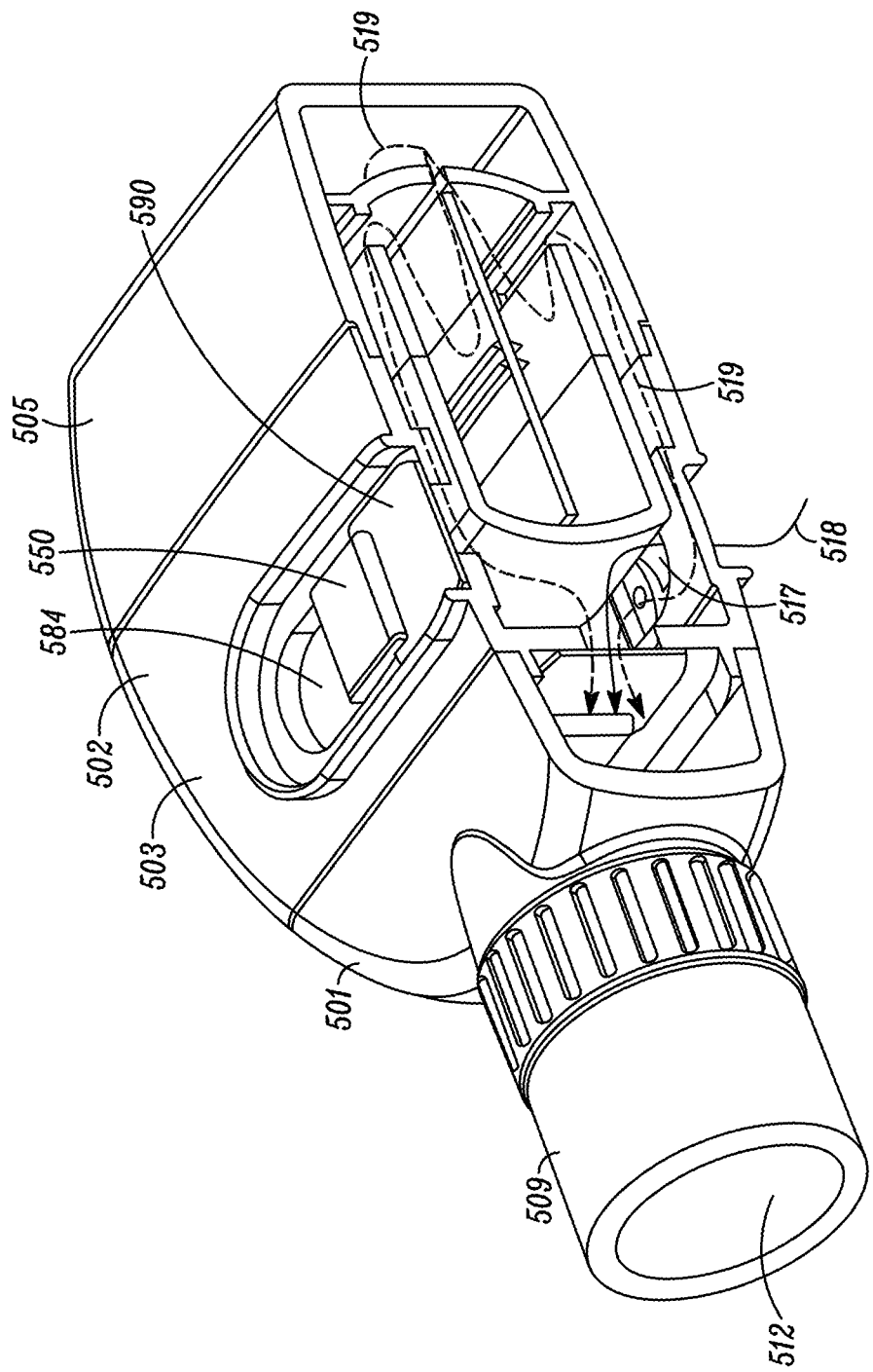
FIG. 65 is a cross-sectional view taken along line I of the respiratory treatment device of FIG. 62.
Figure 66:
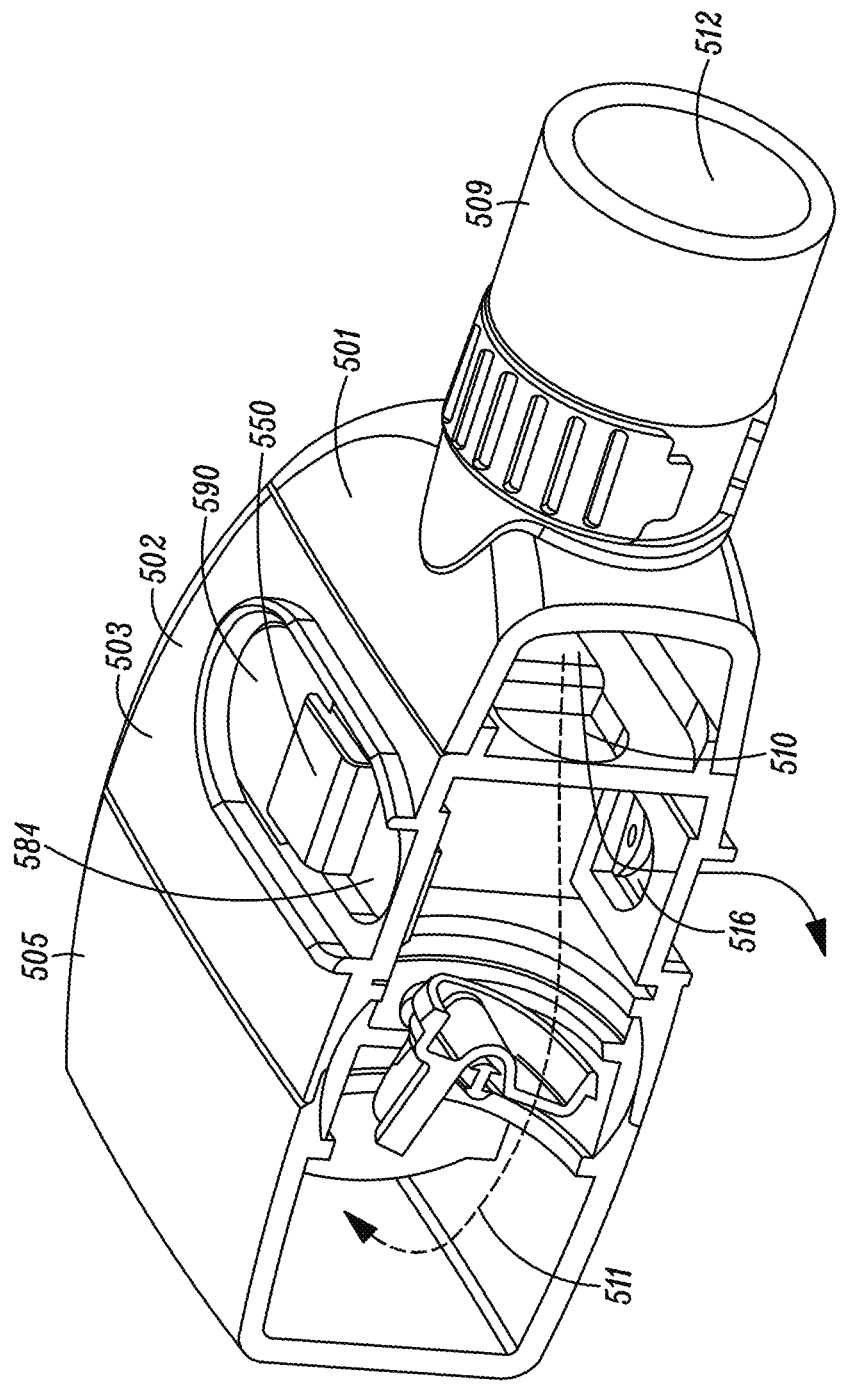
FIG. 66 is a cross-sectional view taken along line II of the respiratory treatment device of FIG. 62.
Figures 67, 68:
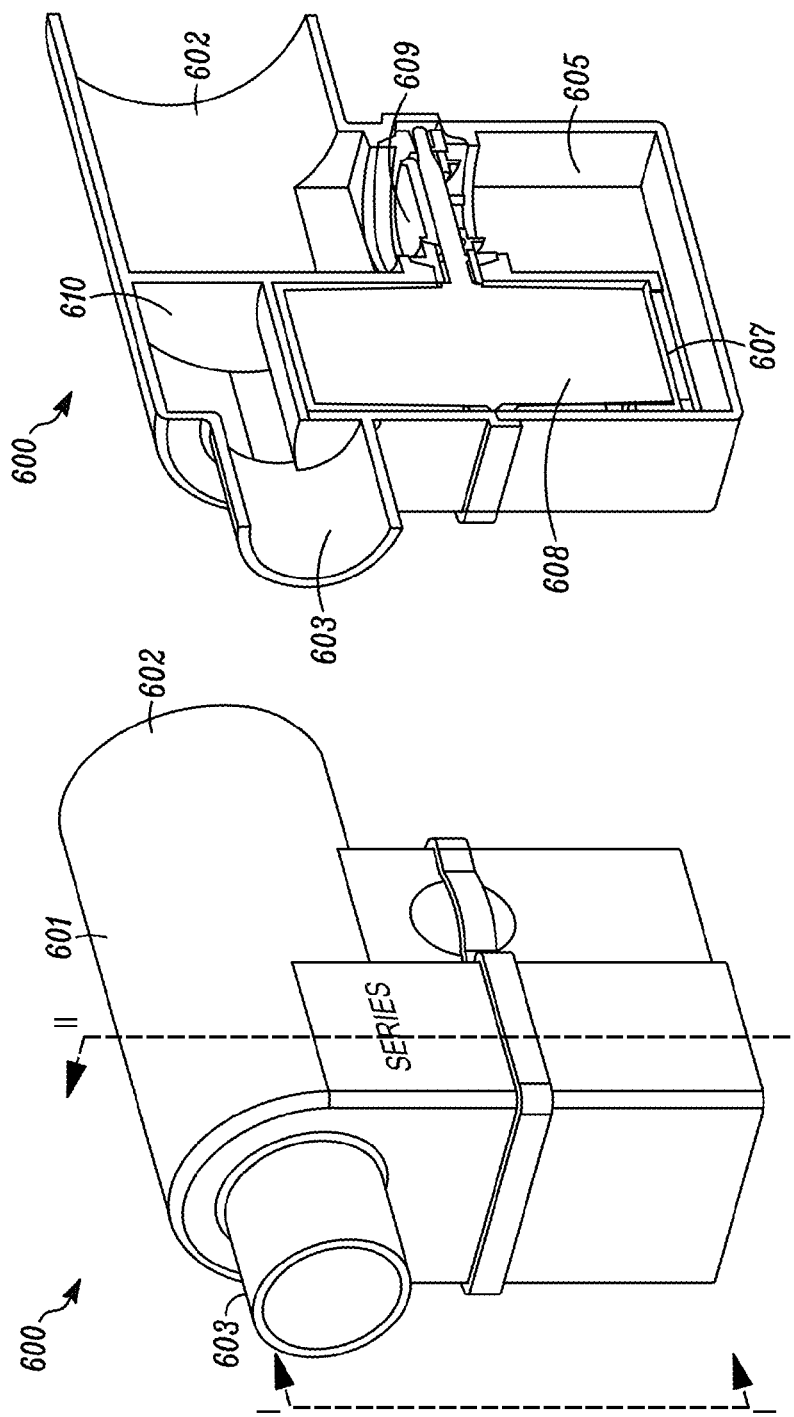
FIG. 67 is a front perspective view of another embodiment of an respiratory treatment device, configured for delivery of pressure threshold therapy in series with OPEP therapy.
FIG. 68 is a cross-sectional view taken along line I of the respiratory treatment device of FIG. 67.
Figure 70:
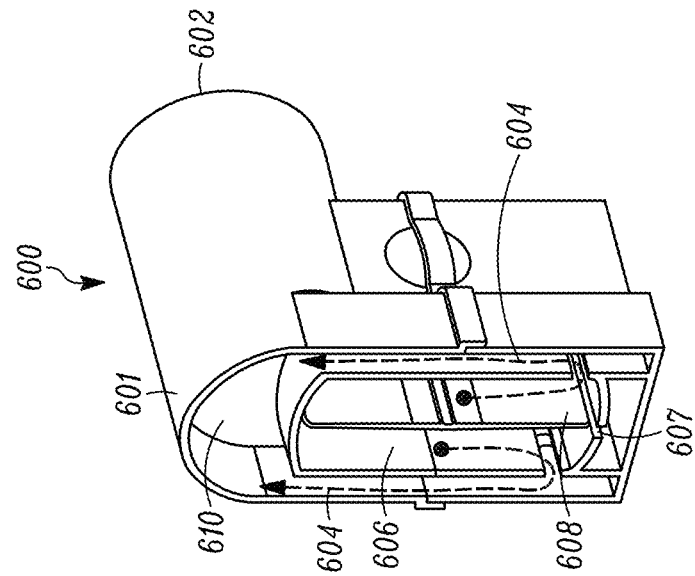
FIG. 70 is a cross-sectional view taken along line II of the respiratory treatment device of FIG. 67.
Figure 69:
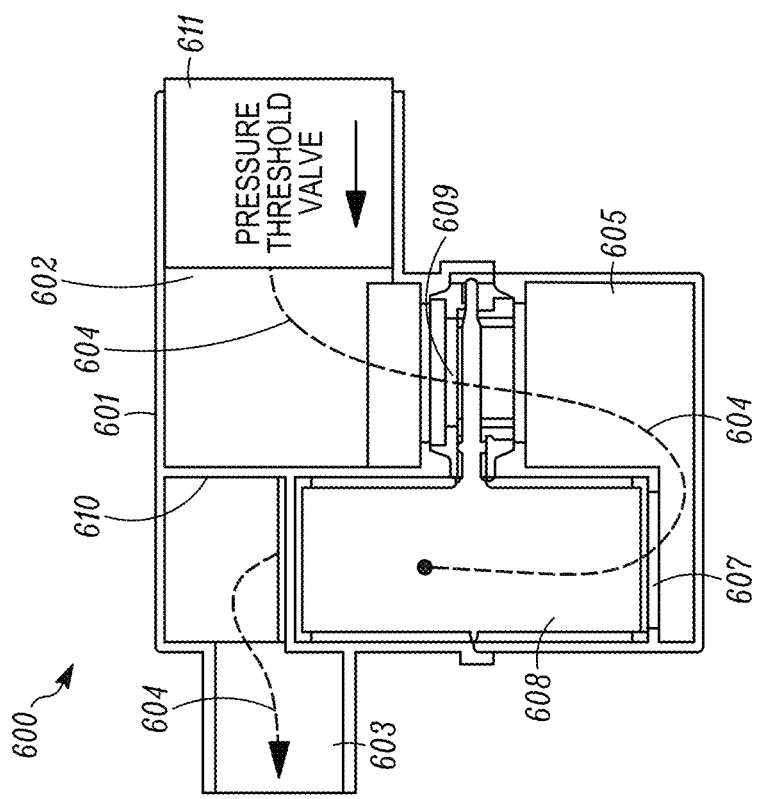
FIG. 69 is a another cross-sectional view taken on along line I of the respiratory treatment device of FIG. 67.
Figure 72:
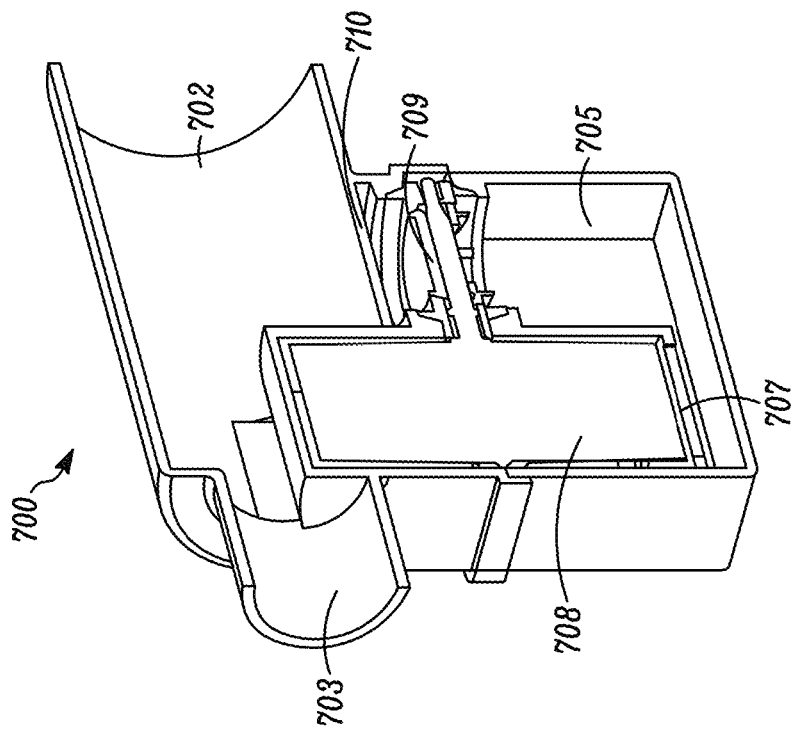
FIG. 72 is a cross-sectional view taken along line I of the respiratory treatment device of FIG. 71.
Figure 71:
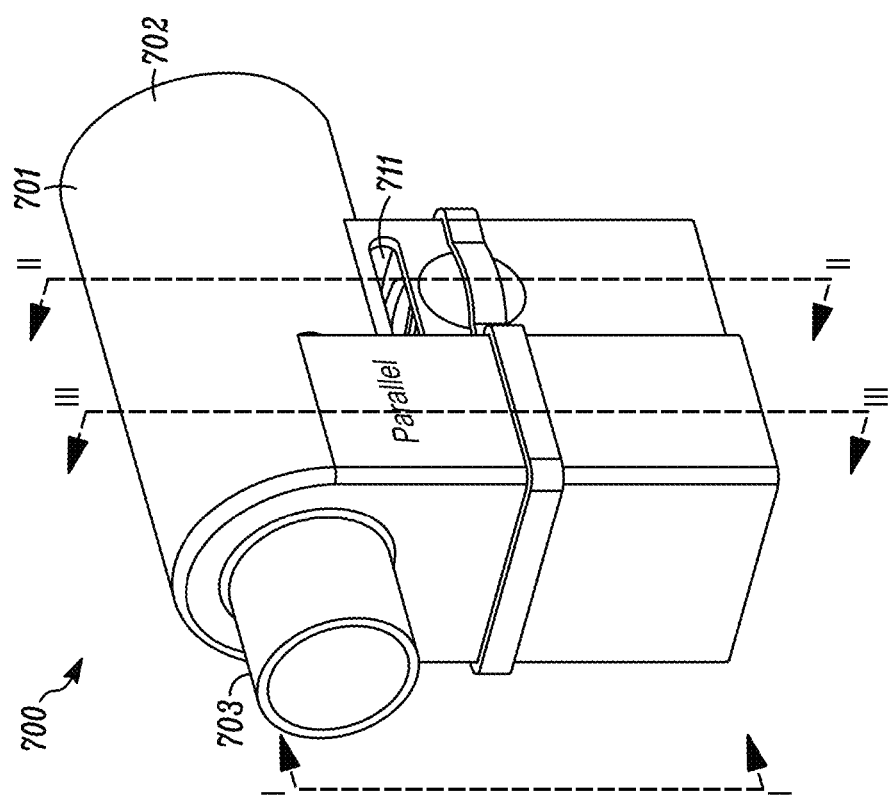
FIG. 71 is a front perspective view of another embodiment of an respiratory treatment device, configured for delivery of pressure threshold therapy in parallel with OPEP therapy.
Figure 74:
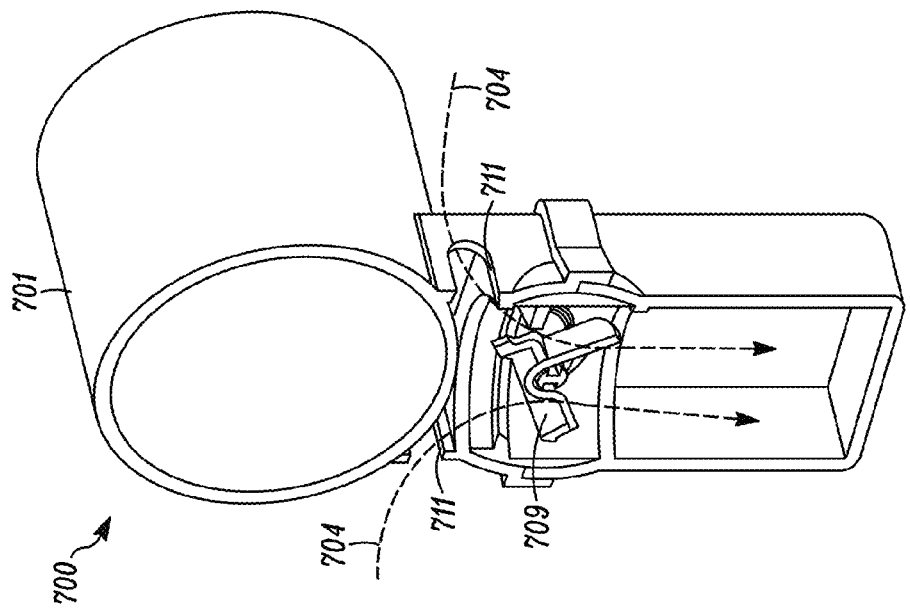
FIG. 74 is a cross-sectional view taken along line II of the respiratory treatment device of FIG. 71.
Figure 73:
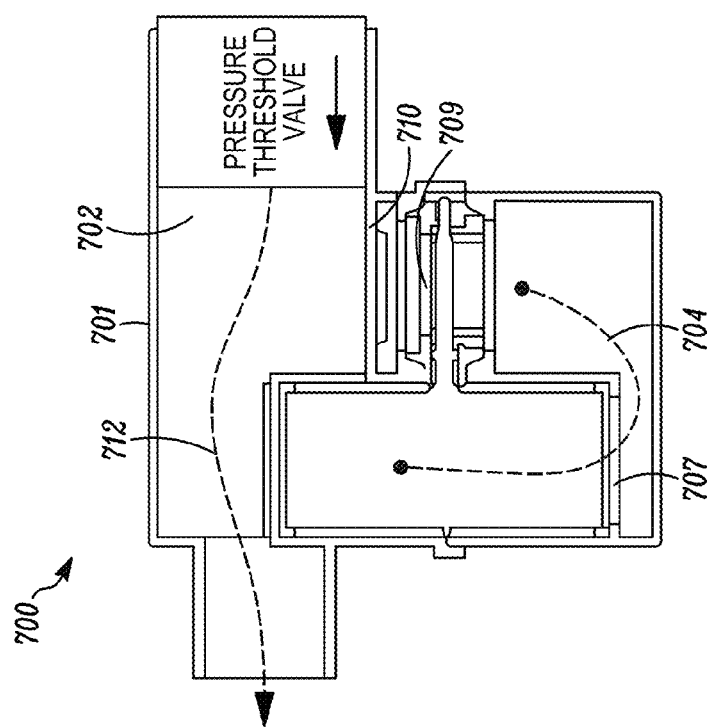
FIG. 73 is another cross-sectional view taken along line I of the respiratory treatment device of FIG. 71.
Figure 75:
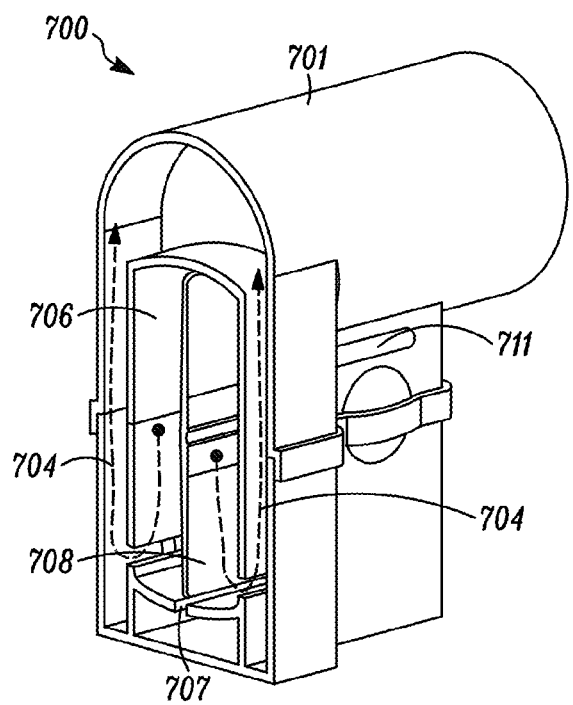
FIG. 75 is a cross-sectional view taken along line III of the respiratory treatment device of FIG. 71.

FIGS. 61 and 62 are front and rear perspective views of the respiratory treatment device 500. FIG. 63A is a front perspective view of the respiratory treatment device 500 shown without the switch 504, whereas FIG. 63B is a rear perspective view of the respiratory treatment device 500 shown without a valve mechanism 550, described below. In general, the respiratory treatment device 500 includes a housing 502 having a font section 501, a middle section 503, and a rear section 505. Like the respiratory treatment device 400, the housing 502 is openable so than the contents of the hosing 502 may be accessed for cleaning and/or selective replacement or adjustment of the components contained therein.

Like the respiratory treatment device 400, as seen in FIG. 63B, the housing 502 includes a first opening 512, a second opening 513, and a third opening 515. As seen in FIG. 63A, the housing 502 of the respiratory treatment device 500 further includes a fourth opening 516, and a fifth opening 517. The valve mechanism 550 is similar to the one-way exhalation valve 490 and the one-way inhalation valve 484 of the respiratory treatment device 400 in that the valve mechanism 550 comprises a one-way exhalation valve member 590 and a one-way inhalation valve member 584 formed together to respectively permit air to exit the housing 502 through the second opening 513 upon exhalation at the first opening 512, and permit air to enter the housing 502 through the third opening 515 upon inhalation at the first opening 512.

Although the first opening 512 is shown as being associated with a mouthpiece 509, the first opening 512 may be associated with other user interfaces. Additionally, as seen in FIGS. 61-62, the mouthpieces 509 may comprise a control port 580 equipped with a regulation member 579 configured to permit a user to selectively adjust the amount of exhaled or inhaled air allowed to pass through the control port 580. As shown in FIGS. 61-62, the regulation member 579 is formed as a ring configured to rotate relative to the mouthpiece 509 to either increase or decrease the cross-sectional area of the control port 579 through which air may flow. By selectively increasing the cross-sectional area of the control port 580 through which air may flow, a user may decrease the amplitude and frequency of the OPEP therapy administered by the respiratory treatment device 500, and vice-versa. In this way, a user may selectively adjust the respiratory treatment device 500 to maintain the ideal operating conditions.

Turning to FIG. 64A-C, front views of the respiratory treatment device 500 are shown, illustrating the positioning of the switch 504 relative to the fourth opening 516 and the fifth opening 517 to selectively control administration of OPEP therapy upon exhalation only, inhalation only, or both exhalation and inhalation. If the switch 504 is in a middle position, as shown in FIG. 64A, both the fourth opening 516 and the fifth opening 517 are blocked, such that the respiratory treatment device 500 will provide OPEP therapy upon both exhalation and inhalation. With the switch 504 in the middle position, the respiratory treatment device 500 operates as shown in FIGS. 57-60 and described above with regards to the respiratory treatment device 400.

With the switch 504 moved to a left position, as shown in FIG. 64B, the fourth opening 516 is closed while the fifth opening 517 remains open, such that the respiratory treatment device 500 will provide OPEP therapy upon exhalation in a manner similar to that of the respiratory treatment device 400 shown in FIGS. 57-58. Upon inhalation, air is drawn into the housing 502 through the fifth opening 517, as shown in the cross-sectional view of FIG. 65. The inhaled air then follows an inhalation flow path 518, as represented by a solid line, between the fifth opening 517 and the mouthpiece 509 associated with the first opening 512. In comparison, when the switch 504 is in the middle position, inhaled air is drawn into the housing 502 through the third opening 515, and follows an inhalation flow path 519 represented, in part, by a dashed line, similar to that of the inhalation flow path 499 of the respiratory treatment device 400 shown in FIGS. 59-60.

If the switch 504 is moved to a right position, as shown in FIG. 64C, the fourth opening 516 remains open, such that the respiratory treatment device 500 will provide OPEP therapy upon inhalation in a manner similar to that of the respiratory treatment device 400 shown in FIGS. 59-60. Upon exhalation, air exits the housing 502 through the fourth opening 516, as shown in the cross-sectional view of FIG. 66. The exhaled air follows an exhalation flow path 510, as represented by a solid line, between the mouthpiece 509 associated with the first opening 512 and the fourth opening 516. In comparison, when the switch 504 is in the middle position, exhaled air follows an exhalation flow path 511 represented, in part, by a dashed line, similar to that of the exhalation flow path 410 of the respiratory treatment device 400 shown in FIGS. 57-58.

Sixth Embodiment

Turning to FIGS. 67-70, another embodiment of a respiratory treatment device 600 is shown. As explained below, the respiratory treatment device 600 is configured to provide pressure threshold therapy in series with OPEP therapy. Although the respiratory treatment device 600 is shown an described as delivering pressure threshold therapy in series with OPEP therapy upon inhalation, it is envisioned that the respiratory treatment device 600 could also be configured for delivery of pressure threshold therapy in series with OPEP therapy upon exhalation.

In general, the respiratory treatment device 600 provides OPEP therapy in a manner similar to the other embodiments described herein. The respiratory treatment device includes a housing 601 enclosing an inhalation portal 602 and a mouthpiece 603. An inhalation flow path 604 is defined through the housing 601 between the inhalation portal 602 and the mouthpiece 603, as represented by a dashed line. The inhalation flow path 604 beings at the inhalation portal 602, passes into a first chamber 605, then into a second chamber 606, before exiting the housing 601 through the mouthpiece 603. Separating the inhalation portal 602 and the mouthpiece is a wall 610. Separating the inhalation portal 602 and the first chamber 605 is a restrictor member 609. Separating the first chamber 605 and the second chamber 606 is an orifice 607. The restrictor member 609 is operatively connected to a vane 608 disposed in the second chamber 606, such that rotation of the vane 608 results in rotation of the restrictor member 609. Similar to the administration of OPEP therapy described above with regards to the previous embodiments, as air flows along the inhalation flow path 604, the vane 608, and therefore the restrictor member 609, reciprocate between a first position, where the restrictor member 609 is closed, and a second position, where the restrictor member 609 is open, thereby creating an oscillating pressure at the mouthpiece 603.

In addition the respiratory treatment device 600 may include a pressure threshold valve 611 disposed in the respiratory portal 602. The pressure threshold valve 611 may be any type of suitable valve configured to remain closed until a given negative pressure is obtained in the inhalation portal 602. In this way, the respiratory treatment device 600 also provides pressure threshold therapy in series with OPEP therapy. For example, as a user inhales at the mouthpiece 603, pressure decreases in the mouthpiece 603, which causes pressure to decrease in the second chamber 606, which causes pressure to decrease in the first chamber 605, which causes pressure to drop in the inhalation port 602. Once the threshold pressure is reached in the inhalation portal 602, the pressure threshold valve 611 opens, allowing air to enter the housing 601 through the inhalation portal 602. As air enters the housing 601 through the inhalation portal 602, it is drawn along the inhalation flow path 604, resulting in the administration of OPEP therapy.

Seventh Embodiment

Turning to FIGS. 71-75, another embodiment of a respiratory treatment 700 device is shown. As explained below, the respiratory treatment device 700 is configured to provide pressure threshold therapy in parallel with OPEP therapy. Although the respiratory treatment device 700 is shown an described as delivering pressure threshold therapy in parallel with OPEP therapy upon inhalation, it is envisioned that the respiratory treatment device 700 could also be configured for delivery of pressure threshold therapy in parallel with OPEP therapy upon exhalation.

In general, the respiratory treatment device 700 provides OPEP therapy in a manner similar to the other embodiments described herein. The respiratory treatment device includes a housing 701 enclosing an inhalation portal 702 and a mouthpiece 703. The housing 701 also comprises one or more inhalation openings 711. An inhalation flow path 704 is defined through the housing 701 between the inhalation openings 711 and the mouthpiece 703, as represented by a dotted line. The inhalation flow path 704 beings at the inhalation openings 711, passes into a first chamber 705, then into a second chamber 706, before exiting the housing 701 through the mouthpiece 703. Separating the inhalation portal 602 and the inhalation openings 711 is a wall 710. Separating the inhalation openings 711 and the first chamber 705 is a restrictor member 709. Separating the first chamber 705 and the second chamber 706 is an orifice 707. The restrictor member 709 is operatively connected to a vane 708 disposed in the second chamber 706, such that rotation of the vane 708 results in rotation of the restrictor member 709. Similar to the administration of OPEP therapy described above with regards to the previous embodiments, as air flows along the inhalation flow path 704, the vane 708, and therefore the restrictor member 709, reciprocate between a first position, where the restrictor member 709 is closed, and a second position, where the restrictor member 709 is open, thereby creating an oscillating pressure at the mouthpiece 703. In addition the respiratory treatment device 700 may include a pressure threshold valve 711 disposed in the respiratory portal 702. The pressure threshold valve 711 may be any type of suitable valve configured to remain closed until a given negative pressure is obtained in the inhalation portal 702. In this way, the respiratory treatment device 700 also provides pressure threshold therapy in parallel with OPEP therapy. For example, as a user inhales at the mouthpiece 703, pressure decreases in the mouthpiece 703 and in the inhalation portal 702, which causes pressure to decrease in the second chamber 706, which causes pressure to decrease in the first chamber 705, which causes air to be drawn into the housing 701 through the inhalation openings 711. As air enters the housing 701 through the inhalation openings 711, it is drawn along the inhalation flow path 704 for the administration of OPEP therapy. Additionally, if the threshold pressure is reached in the inhalation portal 702, the pressure threshold valve 711 opens, allowing air to enter the housing 701 through the inhalation portal 702. As air enters the housing 701 through the inhalation portal 702, it is drawn along a second inhalation flow path 712, as represented by a dashed line.

No Torque Scenarios

A "no torque scenario" in the operation of the embodiments described herein, along with means for reducing the probability of a no torque scenario, will now be described. Although the following descriptions of means for reducing the probability of a no torque scenario are provided with regards to the OPEP device 300 of FIG. 35, it should be appreciated that a no torque scenario may occur in any of the previously described embodiments, and that the means for reducing the probability of a no torque scenario described below may be utilized in any such devices. Likewise, it should be appreciated that the means described below for reducing the probability of a no torque scenario may be utilized in other respiratory treatment devices, such as those shown and described in U.S. patent application Ser. No. 13/489,984, filed on May 6, 2012, which is incorporated herein by reference.

A no torque scenario occurs in the previously described embodiments when the net torque being applied to the restrictor member and the vane, for example, at the start of exhalation, is zero. In such a scenario, the restrictor member and the vane do not rotate, and OPEP therapy is not administered. As used herein, torque is defined as the tendency of a force to rotate an object about an axis, fulcrum, or pivot and can be either positive or negative depending on the direction of rotation. For purposes of the following description, a positive torque is defined as one that opens the restrictor member 330 and a negative torque is one that closes the restrictor member 330. As previously explained, torques act on both the restrictor member 330 and the vane 332 and are created from the pressure and flow of exhaled air along the exhalation flow path 310. The torque that acts on the restrictor member 330 is always positive, whereas the torque that acts on the vane 332 is either positive or negative, depending on the position of the vane 332. As used herein, net torque is defined as the sum of all torques acting on the restrictor member 330 and the vane 332.

Figure 76:
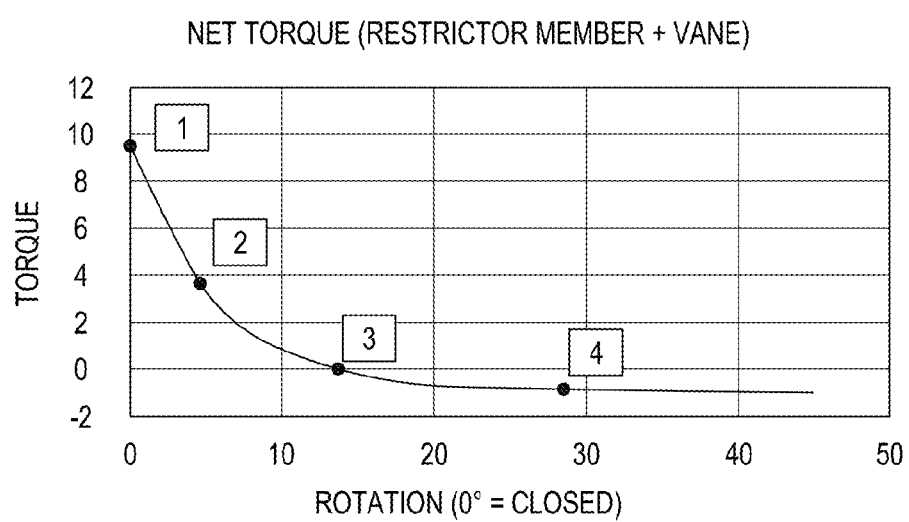
FIG. 76 is an exemplary illustration of the net torque about the restrictor member and the vane of the OPEP device of FIG. 35 as the restrictor member rotates from a closed position to an open position during a period of exhalation.

Turning to FIG. 76, an exemplary illustration is provided showing the net torque about the restrictor member 330 and the vane 330 of the OPEP device 300 as the restrictor member 330 rotates from a closed position to an open position during a period of exhalation. The net torques shown in FIG. 76 are provided solely by way of example, and represent only one possible set of operating characteristics for the OPEP device 300. Four points of interest during the rotation of the restrictor member 330 identified in FIG. 76 are discussed below.

Figure 77A:
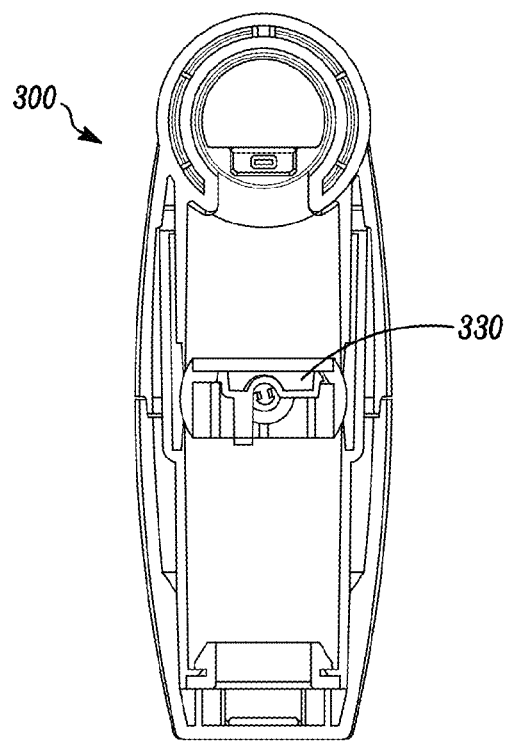
FIGS. 77A-D are cross-sectional views of the OPEP device of FIG. 35 illustrating the position of the restrictor member and the vane at various positions as the restrictor member rotates from a closed position to an open position during a period of exhalation.
Figure 77B:
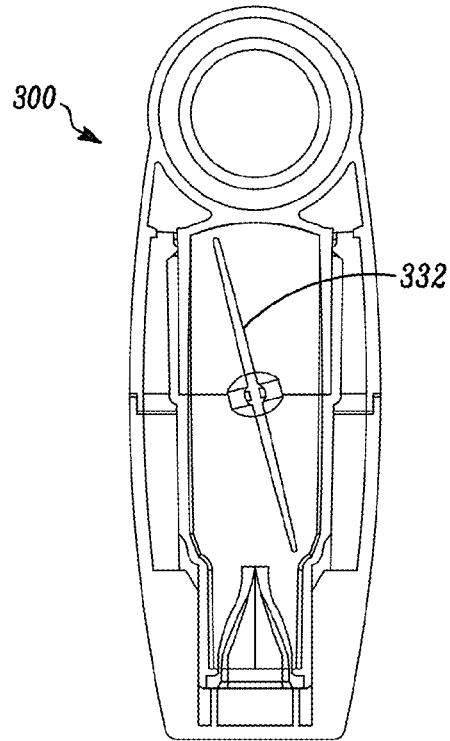

At the first point of interest, or 0° rotation, the restrictor member 330 is completely closed and no air is permitted to flow past the restrictor member 330 into the first chamber 314 during a period of exhalation. The relative positions of the restrictor member 330 and the vane 332, at that point, are shown in FIGS. 77A and 77B. In those positions, the torque on the vane 332 is zero and the torque on the restrictor member 330 is dependent on the pressure generated by the user.

At the second point of interest, the restrictor member 330 begins to open, for example, due to the pressure generated by a user exhaling into the OPEP device 300, and air is permitted to flow past the restrictor member 330 into the first chamber 314. As the restrictor member 330 opens, the torque acting on the restrictor member 330 begins to decrease, while the torque acting on the vane 332 beings to increase. At that point, since the torque on the restrictor member 330 remains dominant, the net torque acting on the restrictor member 330 and the vane 332 decreases.

Figure 77C:
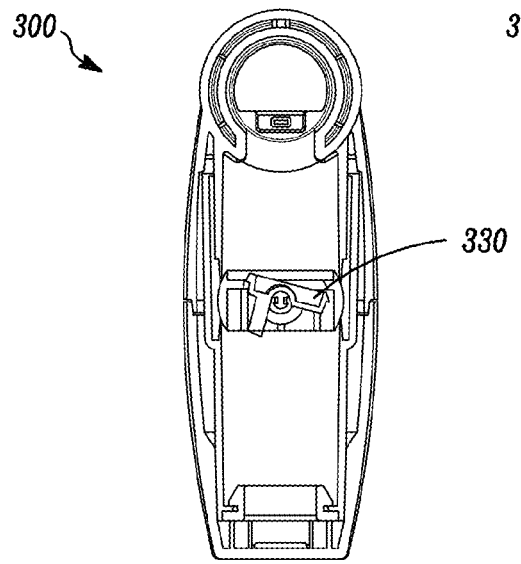
Figure 77D:
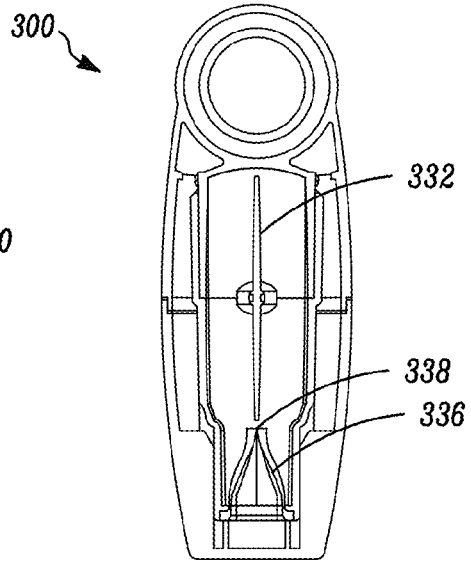

At the third point of interest, the restrictor member 330 and the vane 332 are in a position such that there is no net torque acting on the restrictor member 330 and the vane 332. The approximate positions of the restrictor member 330 and the vane 332, at that point, are respectively shown in FIGS. 77C and 77D. As shown in FIG. 77D, in this position, the vane 332 is nearly aligned with the orifice 338 of the variable nozzle 336. If the restrictor member 330 and the vane 332 are at rest in approximately those positions at the start of a period of exhalation, the resulting net torque may be zero. However, under normal operating conditions, the restrictor member 330 and the vane 332 are not at rest, and there is enough momentum to rotate the restrictor member 330 and the vane 332 past that position for the continued administration of OPEP therapy.

At the fourth point of interest, the restrictor member 330 has rotated past the "no torque position" described as the third point of interest, such that the net torque acting on the restrictor member 330 and the vane 332 is negative.

Figure 78A:
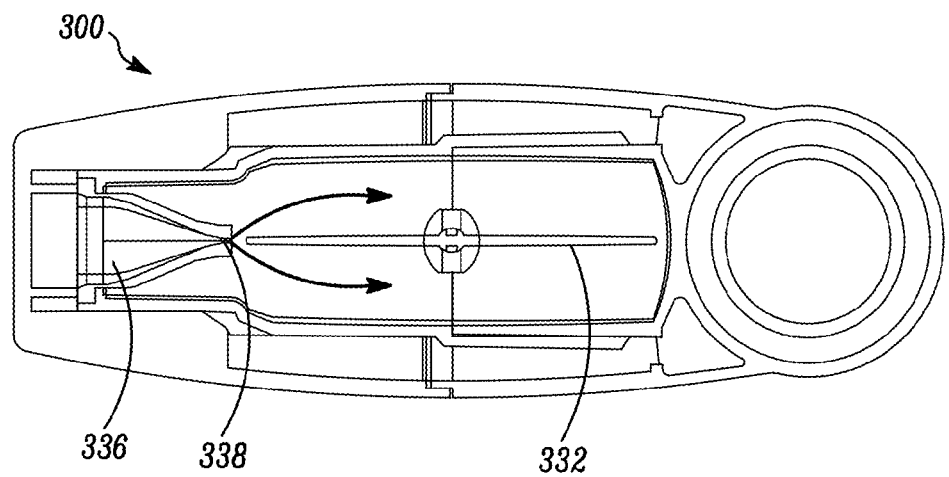
FIGS. 78A-H are various views illustrating the torques applied to the restrictor member and the vane of the OPEP device of FIG. 35 during a period of exhalation, and modifications thereto.

FIG. 78A is a cross-sectional view of the OPEP device 300 of FIG. 35 illustrating a potential no torque scenario. As stated above, no torque scenario may occur when the vane 332 comes to rest in a position almost aligned with the orifice 338 of the variable nozzle 336. In the case of such a scenario, a user could simply tap or shake the OPEP device 300 until the vane 332 rotates out of the position shown in FIG. 78A. Alternatively, a user could open the housing 302 and rotate the vane 332 out of the position shown in FIG. 78A.

Figures 78B, 78C:
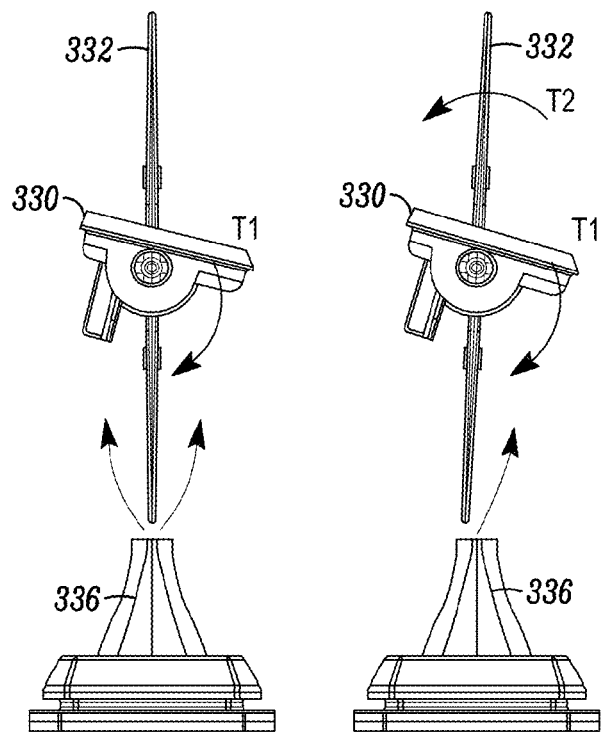

In the position shown in FIG. 78A, the vane 332 may not rotate in response to a flow of exhaled air along the exhalation flow path 310, as the air exiting the variable nozzle 336 through the orifice 338 is split relatively equally on both sides of the vane 332, as illustrated by the arrows shown in FIG. 78A, such that the net torque acting on the restrictor member 330 and the vane 332 is zero. In this position, the pressure on both sides of the vane 332 remains relatively equal, such that any torque about the vane 332 is offset by an opposing torque about the restrictor member 330. As further illustrated in FIG. 78B, when the vane 332 is aligned with the variable nozzle 336, a torque continues to act on the restrictor member 330. Therefore, when the vane 332 is in line with the variable nozzle 336, the only torque acting on the restrictor member 330 and the vane 332 is an opening torque, T1. As this torque begins to turn the restrictor member 330, and therefore the vane 332, the leading edge of the vane 332 directs the air exiting the variable nozzle 336 onto one side of the vane 332, as shown in FIG. 78C, thereby generating a negative torque, T2. When T1 equals T2, a no torque scenario may occur if the momentum of the restrictor member 330 and the vane 332 is not sufficient to continue rotating the restrictor member 330 and the vane 332 past the no torque position.

Figure 78D:
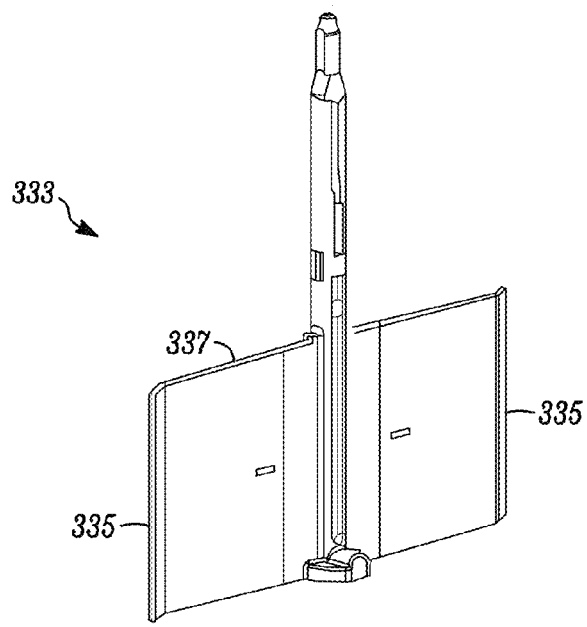
Figure 78E:
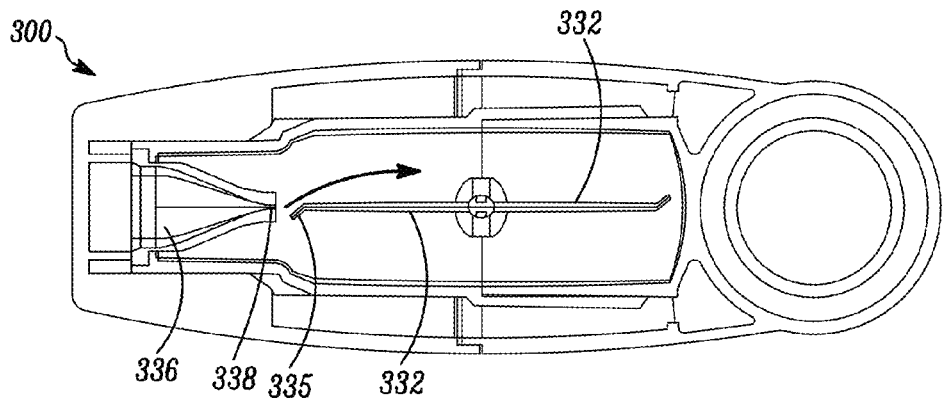

As described herein, various approaches to reducing the probability of a no torque scenario include preventing the vane 332 from stopping in the no torque position, and forcing the vane 332 to move out of the no torque position. In one embodiment, shown in FIG. 78D, a modified vane 333 is configured to reduce the probability of a no torque scenario. In particular, a peripheral portion 335 of the modified vane 333 is angled relative to a central portion 337 of the modified vane 333. Thus, as shown in FIG. 78E, if the modified vane 333 comes to rest in a position where the central portion 337 of the modified vane 333 is directly in-line with the orifice 338 of the variable nozzle 336, the angled peripheral portion 335 of the modified vane 333 directs air exiting the variable nozzle 336 through the orifice 338 onto one side of the vane 333. Consequently, a high pressure is created on one side of the vane 333, causing the vane 333 to rotate.

Figure 78F:
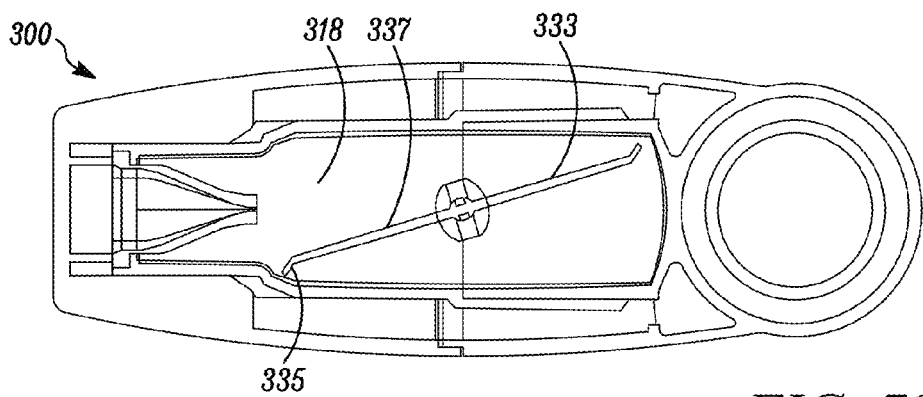

A further modification resulting from inclusion of the modified vane 333 in the OPEP device 300 is illustrated in FIG. 78F. As a result of the angled peripheral portion 335 of the modified vane 333, the total rotation of the modified vane 333, as compared to the unmodified vane 332, is reduced. In particular, the peripheral portion 335 of the modified vane 333 contacts the walls of the second chamber 318 in an orientation with less rotation than that of the unmodified vane 332. Consequently, the restrictor member 330 (see FIGS. 38-40) may not fully close, thereby affecting performance of the OPEP device 300. In order to ensure the restrictor member 330 fully closes, the angle of the central portion 337 of the modified vane 333 relative to the restrictor member 330 may be adjusted.

Figure 78G:
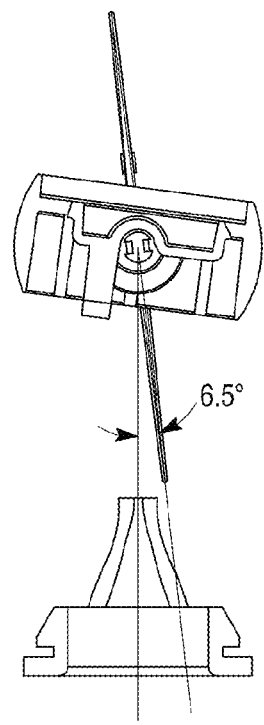
Figure 78H:
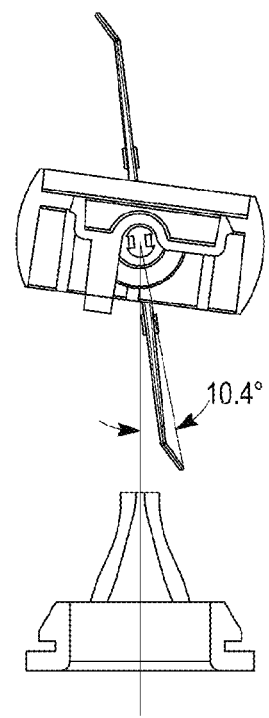

Likewise, the angled peripheral portions 335 also increase the amount of rotation the restrictor member 330 and the modified vane 333 have to build up momentum in order to continue rotating past the no torque position. For example, in one embodiment, illustrated in FIGS. 78G-H, where the OPEP device 300 is configured for the high setting, and with the restrictor member 330 completely closed, the vane 332 only provides 6.5° of rotation, while the modified vane 333 provides 10.4°.

Figure 79A:
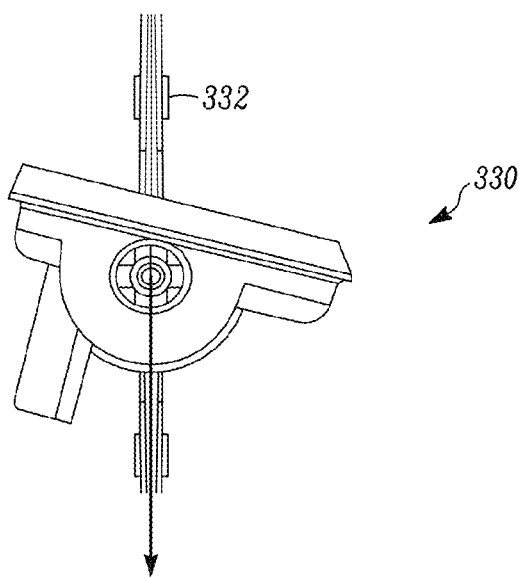
FIGS. 79A-B are top views illustrating the torque applied to the restrictor member of the OPEP device of FIG. 35, and modifications thereto.
Figure 79B:
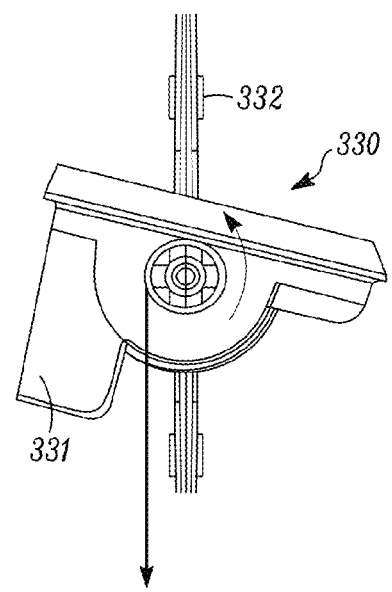

In another embodiment, as shown in FIGS. 79A-B, a weight 331 may be added to the restrictor member 330 such that gravity prevents the vane 332 from stopping in the no torque position. In the previously described design, shown in FIG. 79A, the restrictor member 330 is balanced such that the center of mass is aligned with the axis of rotation and no additional torque is created due to gravity. In the modified design, shown in FIG. 79B, the additional weight 331 moves the center of mass off of the axis of rotation. Thus, when the OPEP device 300 is held in the vertical position, for example, the additional gravitational torque acts to close the restrictor member 330 and move the vane 332 out of the no torque position. However, a consequence of the additional weight 331 is that the performance characteristics of the OPEP device 300 are impacted. Therefore, it is important to provide enough additional weight 331 to move the restrictor mechanism 330 and the vane 332 out of the no torque position, but not so much weight that the performance of the OPEP device 300 suffers. In one embodiment, the ideal amount of additional weight is 0.25 g.

In another embodiment, both of the previously described modifications are utilized, as illustrated in FIGS. 80A-B. In this embodiment, a weight 331 is added to the restrictor member 330, and a peripheral portion 335 of a modified vane 333 is angled relative to a central portion 337. In this way, the modified vane 333 leads to a positive torque, T2, acting on the modified vane 333, such that T1 and T2 work together, rather than cancelling each other out.

In another embodiment, as shown in FIG. 81, an additional weight 339 is added to the restrictor member 330 on the side opposite of the additional weight 331 of the restrictor member 330 shown in FIG. 79B. The additional weight 339 serves to create a positive torque that works to open the restrictor member 330. One benefit of the of this embodiment is that the amount of rotation the restrictor member 330 and the vane 332 have to build up momentum in order to rotate past the no torque position is greater from the fully open position. At low flow rates, however, the performance of the OPEP device 300 may be impacted.

Figure 82A:
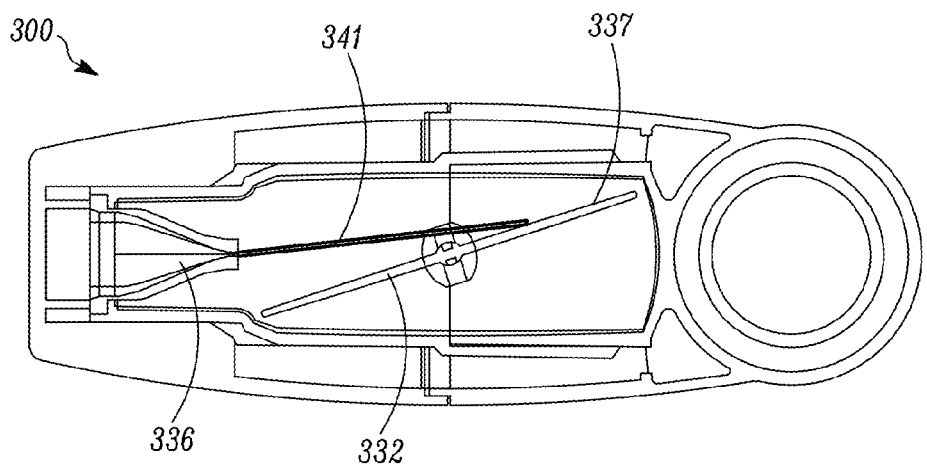
FIGS. 82A-C are cross-sectional views of the OPEP device of FIG. 35 showing a biasing member connected to the vane.
Figure 82B:
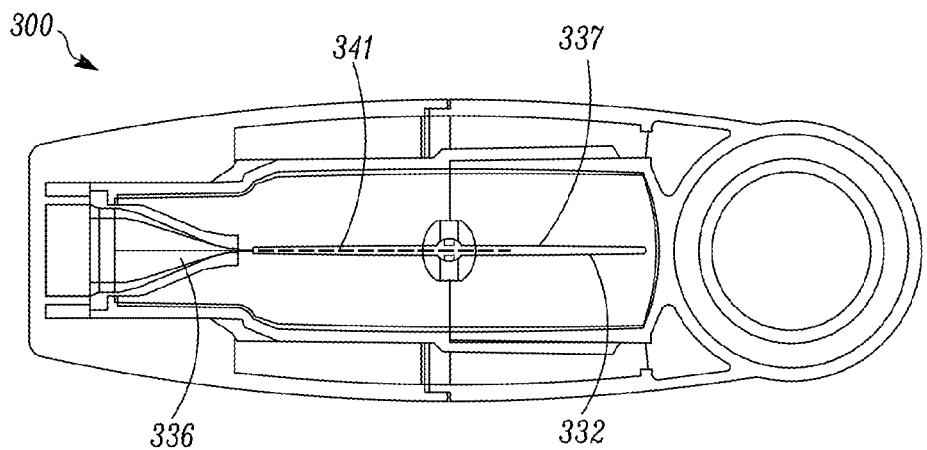
Figure 82C:
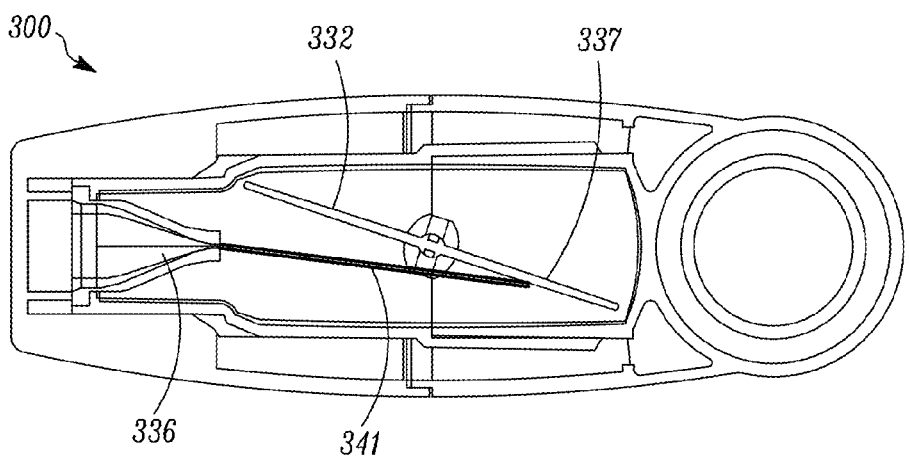

In an alternative embodiment, as shown in FIGS. 82A-C, an elastic band 341 is attached to the vane 332 on the central portion 337 of the vane 332 opposite of the variable nozzle 336. As seen in FIGS. 82A and 82C, when the vane 332 is rotated to the positions shown, the elastic band 341 is not under tension. As seen in FIG. 82B, when the vane rotates toward the position shown, the elastic band 341 is under tension and biases the vane 332 toward one of the positions shown in FIG. 82A or 82B.

Figure 83A:
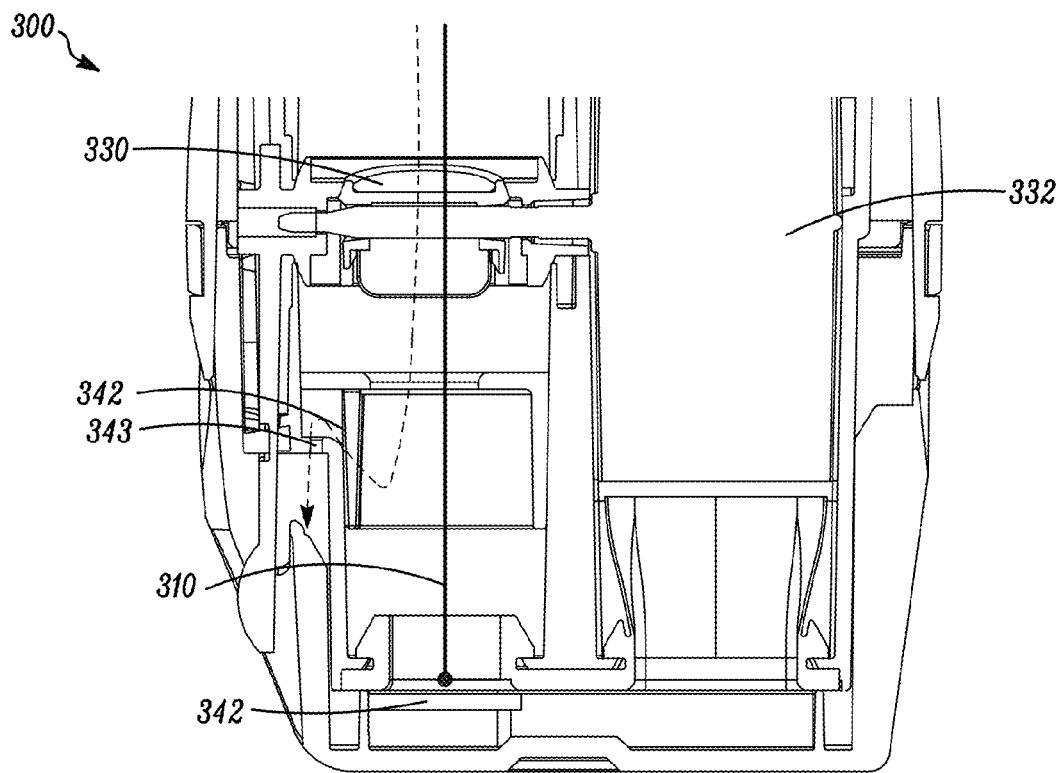
FIGS. 83A-B are partial cross-sectional views of the OPEP device of FIG. 35, modified to include a shuttle valve.
Figure 83B:
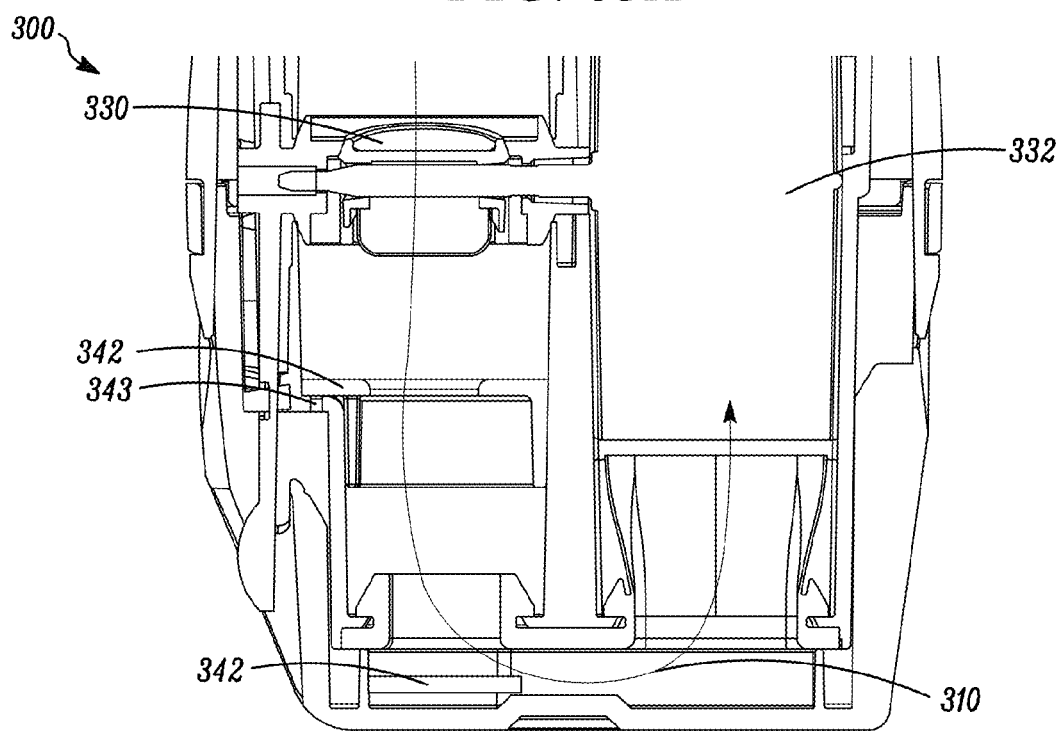

In yet another embodiment, shown in FIGS. 83A-83B, air flow is used to rotate the vane 332 out of the no torque position. At the start of exhalation, as illustrated in FIG. 83A, air flow passes by the restrictor member 330 into the first chamber 314. In the first chamber 314, a shuttle valve 342 obstructs the exhalation flow path 310. The shuttle valve 342 may be biased, for example, by a spring (not shown) tuned to open and close at desired pressures. With the shuttle valve in this position, the exhaled air is permitted to exit the first chamber 314 through an exit port 343. The flow of exhaled air past the restrictor member 330 and out the exit port 343 may therefore rotate the restrictor member 330 and the vane 332 out of a no torque position. Then, as illustrated in FIG. 83B, at a given pressure, the shuttle valve 342 opens and allows the flow of exhaled air to traverse the exhalation flow path 310 for the administration of OPEP therapy. As the shuttle valve 342 opens the flow of exhaled air along the exhalation flow path 310, the shuttle valve 342 also closes the exit port 343 to maintain the ideal operating characteristics.

Figure 84A:
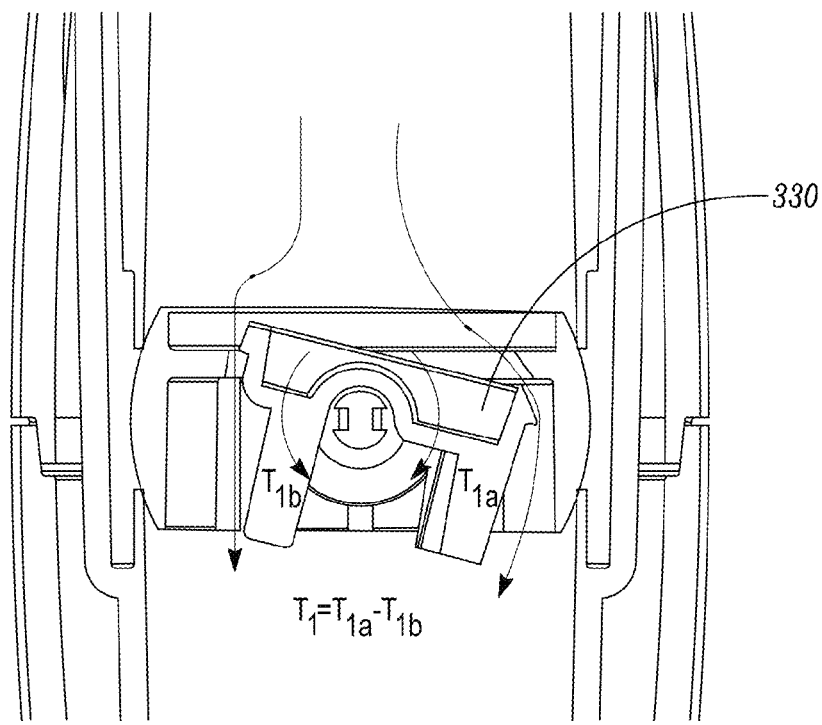
FIGS. 84A-84B are partial cross-sectional views of the OPEP device of FIG. 35, showing the net torques about the restrictor member with and without a diverter.
Figure 84B:
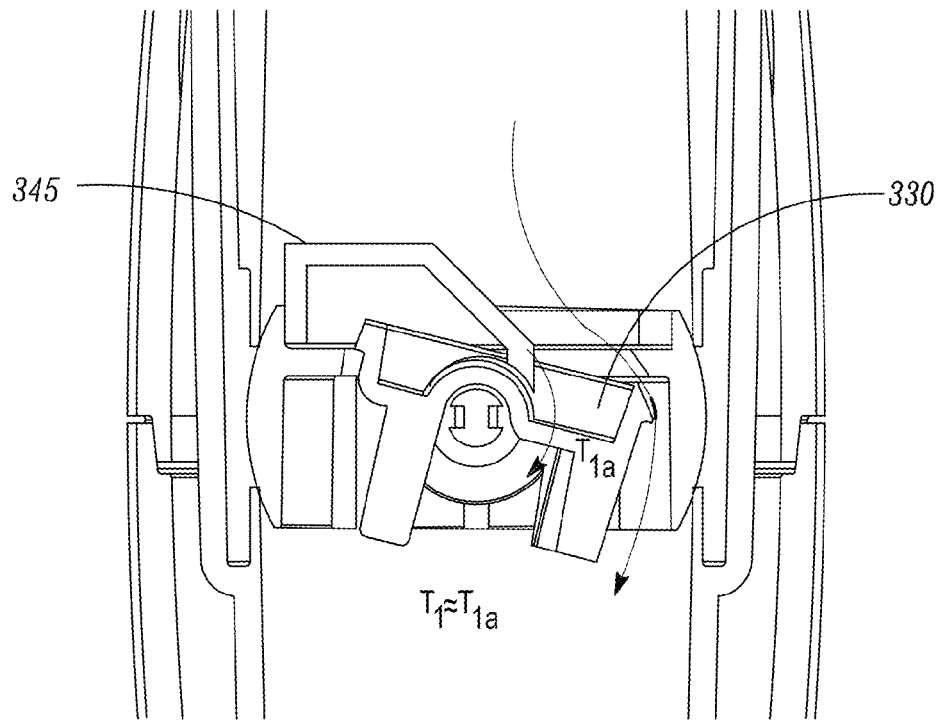

In another embodiment, shown in FIGS. 84A-B, airflow is used to move the restrictor member 330 and the vane 332 out of the no torque position. A top view of the restrictor member 330 is shown in FIG. 84A-B. As shown in FIG. 84A, in the no torque position, exhaled air can flow past the restrictor member 330 on both sides. The opening torque, T1 (referred to above), is the sum of all the torque acting on the restrictor member 330. As shown in FIG. 84B, a diverter may be added upstream of the restrictor member 330 to direct all flow of exhaled air onto one side of the restrictor member 330, thereby increasing the opening torque. A larger opening torque will provide more momentum at startup and therefore lower the chance of a no torque scenario.

In a different embodiment, shown in FIG. 85A-C, inhaled air is used to move the restrictor member 330 and the vane 332 out of a no torque position. As previously described, the OPEP device 300 includes an inhalation port 311 comprising a one-way valve 384 configured to open upon inhalation. In this embodiment, shown in FIGS. 85A-B, a second one-way valve 383 is added to the OPEP device 300 so that air can flow past the restrictor member 330 during inhalation. Normally, air cannot flow past the restrictor member 330 during inhalation because the variable nozzle 336 closes. In this embodiment, the flow of air past the restrictor member 330 upon inhalation creates a torque that moves the restrictor member 330 and the vane 332 out of the no torque position. Upon exhalation, shown in FIG. 85C, both inhalation valves 383 and 384 close and the OPEP device 300 functions as normal.

Figure 86A:
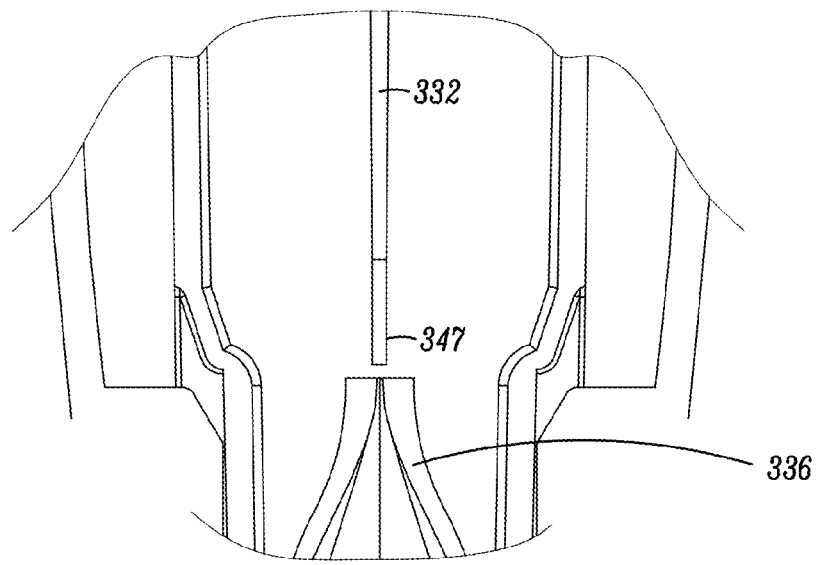
Figure 86B:
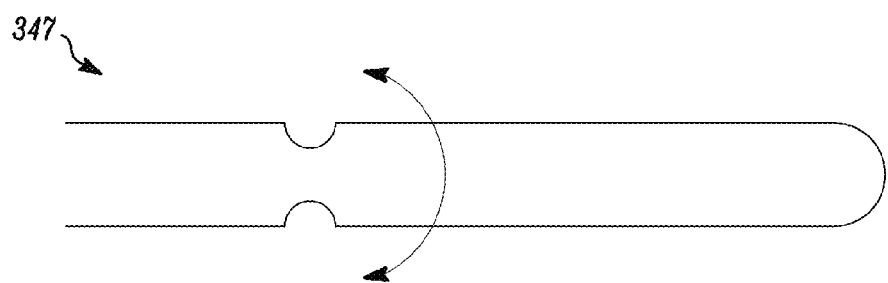
Figure 86C:
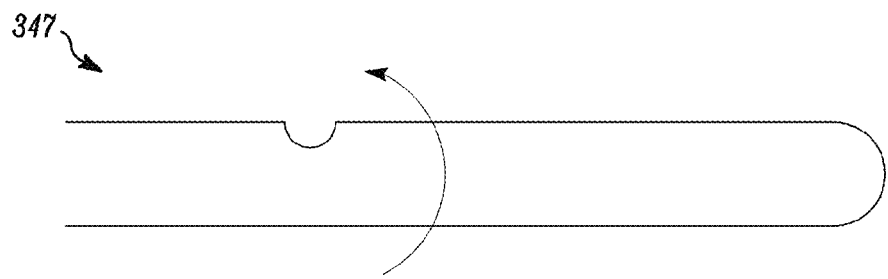

In yet another embodiment, shown in FIGS. 86A-C, air flow at the leading edge of the vane 332 is used to move the vane 332 and the restrictor member 330 out of the no torque position. As shown in FIG. 86A, a flexible tip 347 may added to the end of the vane 332 that, in the no torque position, flexes and/or vibrates as air exits the variable nozzle 336. The flexible tip 347 may be formed of any suitable elastic material. As the flexible tip 347 flexes and/or vibrates, the vane 332 is urged out of the no torque position. The flexible tip 347 may also comprise one or more hinge points 349. If the flexible tip 347 includes hinge points 349 on both sides of the flexible tip 347, as shown in FIG. 86B, the flexible tip will flex in both directions. If the flexible tip 347 includes a hinge point 349 on only one side of the flexible tip 347, as shown in FIG. 86C, the flexible tip will flex only in that direction, thus resulting in an angled peripheral portion of the vane 332, similar to the modified vane 333 described above.

Those skilled in the art will appreciated that the various concepts described above with regards to a particular embodiment of a respiratory treatment device may also be applied to any of the other embodiments described herein, even though not specifically shown or described with regards to the other embodiments. For example, any one of the embodiments described herein may include a variable nozzle, an inhalation port adapted for use with an aerosol delivery device for the administration of aerosol therapy, an adjustment mechanism for adjusting the relative position of the chamber inlet and/or the permissible range of movement by a restrictor member, means for reducing the probability of a no torque scenario, etc.

Although the foregoing description is provided in the context of OPEP devices, it will also be apparent to those skilled in the art will that any respiratory device may benefit from various teachings contained herein. The foregoing description has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

EXEMPLARY IMPLEMENTATIONS

In one implementation, a respiratory treatment device includes a plurality of chambers, a first opening in the housing configured to transmit air exhaled into and air inhaled form the housing, a second opening in the hosing configured to permit air exhaled into the first opening to exit the housing, and a third opening in the housing configured to permit air outside the housing to enter the housing upon inhalation at the first opening. An exhalation flow path is defined between the first opening and the second opening, and an inhalation flow path is defined between the third opening and the first opening. A restrictor member is positioned in the exhalation flow path and the inhalation flow path, such that the restrictor member is movable between a closed position, where a flow of air along the exhalation flow path or the inhalation flow path is restricted, and an open position, where the flow of exhaled air along the exhalation flow path or the inhalation flow path is less restricted. A vane is in fluid communication with the exhalation flow path and the inhalation flow path, the vane being operatively connected to the restrictor member and configured to repeatedly reciprocate between a first position and a second position in response to the flow of air along the exhalation flow path or the inhalation flow path. A fourth opening in the housing is configured to permit the flow of air along the exhalation flow path to exit the housing prior to the position of the restrictor member in the exhalation flow path. A fifth opening in the housing is configured to permit air outside the housing to enter the inhalation flow path upon inhalation at the first opening subsequent to the position of the restrictor member in the inhalation flow path. A switch is positioned relative to the fourth opening and the fifth opening such that one or both of the fourth opening and the fifth opening may be closed by the switch.

The respiratory treatment device may be configured to provide OPEP therapy upon both inhalation and exhalation when the switch is positioned relative to the fourth opening and the fifth opening such that both of the fourth opening and the fifth opening are closed by the switch. The respiratory treatment device may be configured to provide OPEP therapy upon exhalation when the switch is positioned relative to the fourth opening such that the fourth opening is closed by the switch. The respiratory treatment device may be configured to provide OPEP therapy upon inhalation when the switch is positioned relative to the fifth opening such that the fifth opening is closed by the switch.

The exhalation flow path and the inhalation flow path may form an overlapping portion. The flow of air along the exhalation flow path and the inhalation flow path along the overlapping portion may be in the same direction. The restrictor member may be positioned in the overlapping portion, while the vane may be in fluid communication with the overlapping portion. The restrictor member may be positioned in a first chamber of the plurality of chambers, while the vane may be positioned in a second chamber of the plurality of chambers. The flow of air through an inlet to the first chamber may be restricted when the restrictor member is in the closed position, while the flow of air through the inlet may be less restricted when the restrictor member is in the open position. The first chamber and the second chamber may be connected by an orifice. The vane may be positioned adjacent the orifice, the vane being configured to move the restrictor member between the closed position and the open position in response to an increased pressure adjacent the vane.

The second opening may include a one-way exhalation valve configured to permit air exhaled into the housing to exit the housing upon exhalation at the first opening. The third opening may include a one-way inhalation valve configured to permit air outside the housing to enter the housing upon inhalation at the first opening. A one-way valve may be positioned along the exhalation flow path between the first opening and the second opening, the one-way valve being configured to open in response to air exhaled into the first opening, and close in response to air inhaled through the first opening. A one-way valve may be positioned along the inhalation flow path between the third opening and the first opening, the one-way valve being configured to open in response to air inhaled through the first opening, and close in response to air exhaled into the first opening.

An inhalation port may be in fluid communication with a user interface, wherein the inhalation port is adapted to receive an aerosol medicament from an aerosol delivery device. The aerosol delivery device may be connected to the inhalation port.

In another implementation, a respiratory treatment device includes a housing enclosing at least one chamber, a chamber outlet configured to permit air in the housing to exit the housing, and a chamber inlet configured to permit air outside the housing to enter the housing. A flow path is defined between the chamber inlet and the chamber outlet. A restrictor member is positioned in the flow path, the restrictor member being moveable between a closed position, where a flow of air along the flow path is restricted, and an open position, where the flow of air along the flow path is less restricted. A vane is in fluid communication with the flow path, the vane being operatively connected to the restrictor member and configured to reciprocate between a first position and a second position in response to a flow of air along the flow path. A one-way valve is positioned in one of the chamber inlet or the chamber outlet and is configured to close the one of the chamber inlet or the chamber outlet until a threshold pressure is obtained. The respiratory treatment device may be configured to provide OPEP therapy in series with pressure-threshold therapy.

In another implementation, a respiratory treatment device includes a housing enclosing at least one chamber, a chamber outlet configured to permit air in the housing to exit the housing, and a chamber inlet configured to permit air outside the housing to enter the housing. A flow path is defined between the chamber inlet and the chamber outlet. A restrictor member is positioned in the flow path, the restrictor member being moveable between a closed position, where a flow of air along the flow path is restricted, and an open position, where the flow of air along the flow path is less restricted. A vane is in fluid communication with the flow path, the vane being operatively connected to the restrictor member and configured to reciprocate between a first position and a second position in response to a flow of air along the flow path. A one-way valve is positioned in an opening and is configured to close the opening until a threshold pressure is obtained. The respiratory treatment device may be configured to provide OPEP therapy in parallel with pressure-threshold therapy.

In another implementation, a respiratory treatment device includes a housing enclosing at least one chamber, a chamber inlet configured to receive exhaled air into the at least one chamber, and a chamber outlet configured to permit exhaled air to exit the at least one chamber. An exhalation flow path is defined between the chamber inlet and the chamber outlet. A restrictor member is positioned in the exhalation flow path, the restrictor member being moveable between a closed position, where a flow of air along the exhalation flow path is restricted, and an open position, where the flow of air along the exhalation flow path is less restricted. A vane is in fluid communication with the exhalation flow path, the vane being operatively connected to the restrictor member and configured to reciprocate between a first position and a second position in response to a flow of air along the exhalation flow path. A shuttle valve is positioned in the exhalation flow in a position between the restrictor member and the vane, the shuttle valve being configured to move in response to a threshold pressure obtained at the chamber inlet from a first position, where the flow of air along the exhalation flow path is diverted to an exit port, and a second position, where the flow of air along the exhalation flow path past the shuttle valve is permitted.

In another implementation, a respiratory treatment device includes a housing enclosing at least one chamber, a chamber inlet configured to receive exhaled air into the at least one chamber, and a chamber outlet configured to permit exhaled air to exit the at least one chamber. An exhalation flow path is defined between the chamber inlet and the chamber outlet. A restrictor member is positioned in the exhalation flow path, the restrictor member being moveable between a closed position, where a flow of air along the exhalation flow path is restricted, and an open position, where the flow of air along the exhalation flow path is less restricted. A vane is in fluid communication with the exhalation flow path, the vane being operatively connected to the restrictor member and configured to reciprocate between a first position and a second position in response to a flow of air along the exhalation flow path. A one-way inhalation valve is positioned along the exhalation flow path in a position between the restrictor member and the vane, and is configured to open once a threshold pressure is obtained upon inhalation at the chamber inlet.

What is claimed is:

1. A respiratory treatment device comprising:
   a housing enclosing at least one chamber;
   a chamber inlet configured to receive air into the at least one chamber;
   at least one chamber outlet configured to permit air to exit the at least one chamber;
   a flow path defined between the chamber inlet and the at least one chamber outlet;
   an orifice positioned in the at least one chamber along the flow path such that the flow path passes through the orifice, and,
   a vane positioned adjacent the orifice, the vane being configured to rotate in response to the flow of air through the orifice;
   wherein the vane is biased by an elastic band toward a position where a central portion of the vane is not aligned with the orifice.

2. The respiratory treatment device of claim 1, wherein the vane is substantially planar.

3. The respiratory tournament device of claim 1, where an end of the elastic band is attached to a side of the vane opposite the side of the vane adjacent the orifice.

4. The respiratory treatment device of claim 1, further comprising a restrictor member operatively connected to the vane, the restrictor member being configured to rotate between a closed position, where the flow of air along the flow path is restricted, and an open position, where the flow of air along the flow path is less restricted.

5. The respiratory treatment device of claim 4, wherein the restrictor member and the vane are operatively connected by a shaft.

6. The respiratory treatment device of claim 5, wherein the restrictor member has a center of mass offset from an axis of rotation of the shaft.

7. The respiratory treatment device of claim 6, wherein a force of gravity biases the restrictor member and the vane toward the position where the central portion of the vane is not aligned with the orifice.

8. The respiratory treatment device of claim 4, wherein the restrictor member is biased by the elastic band.

9. The respiratory treatment device of claim 5, wherein the restrictor member is biased by the elastic band.

10. A respiratory treatment device comprising:
    a housing enclosing at least one chamber;
    a chamber inlet configured to receive air into the at least one chamber;
    at least one chamber outlet configured to permit air to exit the at least one chamber;
    a flow path defined between the chamber inlet and the at least one chamber outlet;

a restrictor member movable between a closed position, where the flow of air along the flow path is restricted, and an open position, where the flow of air along the flow path is less restricted;

an orifice positioned in the at least one chamber along the flow path such that the flow path passes through the orifice, and, a vane positioned adjacent the orifice, the vane being operatively connected to the restrictor member and configured to rotate in response to the flow of air through the orifice;

wherein the restrictor member is biased by an elastic band toward a position where a central portion of the vane is not aligned with the orifice.

11. The respiratory treatment device of claim 10, wherein the restrictor member and the vane are operatively connected by a shaft.

12. The respiratory treatment device of claim 10, wherein the elastic band is attached to the vane.

13. The respiratory treatment device of claim 11, wherein the elastic band is attached to the vane.

14. A respiratory treatment device comprising:
a housing enclosing at least one chamber;
a chamber inlet configured to receive air into the at least one chamber;
at least one chamber outlet configured to permit air to exit the at least one chamber;
a flow path defined between the chamber inlet and the at least one chamber outlet;
a restrictor member movable between a closed position, where the flow of air along the flow path is restricted, and an open position, where the flow of air along the flow path is less restricted;
an orifice positioned in the at least one chamber along the flow path such that the flow path passes through the orifice, and,
a vane positioned adjacent the orifice, the vane being operatively connected to the restrictor member and configured to rotate in response to the flow of air through the orifice;
wherein the vane and restrictor member are biased by an elastic band toward a position where a central portion of the vane is not aligned with the orifice.

15. The respiratory treatment device of claim 14, wherein the restrictor member and the vane are operatively connected by a shaft.

16. The respiratory treatment device of claim 14, wherein the elastic band is attached to the vane.

17. The respiratory treatment device of claim 15, wherein the elastic band is attached to the vane.

* * * * *